US008541522B2

(12) United States Patent
Giesbrecht et al.

(10) Patent No.: US 8,541,522 B2
(45) Date of Patent: Sep. 24, 2013

(54) CATALYST COMPOUNDS AND USE THEREOF

(75) Inventors: Garth R. Giesbrecht, The Woodlands, TX (US); Timothy M. Boller, Houston, TX (US); Alexander Z. Voskoboynikov, Moscow (RU); Andrey F. Asachenko, Chelyabinsk (RU); Mikhail V. Nikulin, Moscow Region (RU); Alexey A. Tsarev, Tula (RU)

(73) Assignee: ExxonMobil Chemical Patents Inc., Houston, TX (US)

( * ) Notice: Subject to any disclaimer, the term of this patent is extended or adjusted under 35 U.S.C. 154(b) by 252 days.

(21) Appl. No.: 12/908,268

(22) Filed: Oct. 20, 2010

(65) Prior Publication Data

US 2011/0098429 A1     Apr. 28, 2011

Related U.S. Application Data

(60) Provisional application No. 61/255,725, filed on Oct. 28, 2009, provisional application No. 61/255,742, filed on Oct. 28, 2009, provisional application No. 61/255,750, filed on Oct. 28, 2009.

(30) Foreign Application Priority Data

Dec. 10, 2009   (EP) ..................... 09178615

(51) Int. Cl.
*C08F 4/76*   (2006.01)
*C08F 4/64*   (2006.01)
*C07F 7/00*   (2006.01)

(52) U.S. Cl.
USPC ........... 526/172; 526/161; 526/160; 526/170; 526/348; 526/352; 556/51

(58) Field of Classification Search
USPC .................... 556/51; 526/172, 161
See application file for complete search history.

(56) References Cited

U.S. PATENT DOCUMENTS

| | | | |
|---|---|---|---|
| 5,767,209 A | 6/1998 | McNally | |
| 6,333,292 B1 | 12/2001 | Gibson et al. | |
| 6,531,555 B2 | 3/2003 | Whiteker | |
| 6,534,664 B1 | 3/2003 | Guram et al. | |
| 6,593,266 B1 | 7/2003 | Matsui et al. | |
| 6,713,577 B2 | 3/2004 | Boussie et al. | |
| 6,825,296 B2 | 11/2004 | Chan et al. | |
| 6,939,969 B2 | 9/2005 | Peters et al. | |
| 6,974,878 B2 | 12/2005 | Guram et al. | |
| 6,998,363 B2 | 2/2006 | Chan et al. | |
| 7,009,014 B2 | 3/2006 | Suzuki et al. | |
| 7,105,672 B2 | 9/2006 | Chan et al. | |
| 7,253,133 B2 * | 8/2007 | Sun et al. ..................... | 502/167 |
| 7,317,057 B2 | 1/2008 | Solan et al. | |
| 7,423,101 B2 | 9/2008 | Solan et al. | |
| 7,767,773 B2 | 8/2010 | Giesbrecht et al. | |
| 7,847,099 B2 | 12/2010 | Agapie et al. | |
| 7,858,718 B1 | 12/2010 | Nagy et al. | |
| 2002/0049288 A1 | 4/2002 | Goh et al. | |
| 2004/0092682 A1 | 5/2004 | Queisser et al. | |
| 2006/0135713 A1 | 6/2006 | Leclerc et al. | |
| 2007/0100145 A1 | 5/2007 | Boussie et al. | |
| 2008/0182952 A1 | 7/2008 | Giesbrecht et al. | |
| 2008/0319147 A1 | 12/2008 | Solan et al. | |
| 2010/0152398 A1 | 6/2010 | Aliyev et al. | |
| 2011/0098425 A1 | 4/2011 | Giesbrecht et al. | |
| 2011/0098427 A1 | 4/2011 | Giesbrecht et al. | |
| 2011/0098430 A1 | 4/2011 | Giesbrecht et al. | |
| 2011/0098431 A1 | 4/2011 | Giesbrecht et al. | |

FOREIGN PATENT DOCUMENTS

| | | |
|---|---|---|
| EP | 0 950 667 | 10/1999 |
| JP | 2000 063639 | 2/2000 |
| JP | 2000/109462 | 4/2000 |
| JP | 2004 346268 | 12/2004 |
| WO | WO 00/20427 | 4/2000 |
| WO | WO 01/10875 | 2/2001 |
| WO | 01/74910 | 10/2001 |
| WO | WO 01/74910 | 10/2001 |
| WO | WO 02/079207 | 10/2002 |
| WO | WO 03/054038 | 7/2003 |
| WO | WO 2004/016627 | 2/2004 |
| WO | WO 2004/081020 | 9/2004 |
| WO | WO 2007/090412 | 8/2007 |
| WO | WO 2008/036882 | 3/2008 |
| WO | WO 2008/036882 | 8/2008 |
| WO | WO 2009/082556 | 7/2009 |

OTHER PUBLICATIONS

U.S. Appl. No. 61/255,725, filed Oct. 28, 2009, Giesbrecht et al.
U.S. Appl. No. 61/255,742, filed Oct. 28, 2009, Giesbrecht et al.
U.S. Appl. No. 61/255,750, filed Oct. 28, 2009, Giesbrecht et al.
U.S. Appl. No. 61/255,758, filed Oct. 28, 2009, Giesbrecht et al.
Fernandes et al., "Rapid Report: Polymerisation of Ethylene Catalysed by Momo-imine-2, 6-Diacetylpridine Iron/Methylaluminoxane (MAO) Catalyst System: Effect of the Ligand on Polymer Microstructure", Society of Chemical Industry, Polymer International, 2002, vol. 51, No. 21, pp. 1301-1303.
Keypour et al., "Isolation of Ternary Complex Precursors and Partially Condensed Intermediates to Macrocyclic Complexes of Nickel(II) and copper(II)", Transition Metal Chemistry (London), 1998, vol. 23, No. 5, pp. 609-613.
van der Linden et al, "Polymerization of A-Olefins and Butadine and Catalytic Cyclotrimerization of 1-Alkynes by a New Class of Group IV Catalysts. Control of Molecular Weight and Polymer Microstructure Via Ligand Tuning in Sterically Hindered Chelating Phenoxide Titanium and Zirconium Species", Journal of the American Chemical Society, 1995, vol. 117, No. 1, pp. 3008-3021.

(Continued)

*Primary Examiner* — Rip A. Lee
(74) *Attorney, Agent, or Firm* — Catherine L. Bell

(57) ABSTRACT

This invention relates to Group 4 catalyst compounds containing di-anionic tridentate nitrogen/oxygen based ligands. The catalyst compounds are useful, with or without activators, to polymerize olefins, particularly α-olefins, or other unsaturated monomers. Systems and processes to oligomerize and/or polymerize one or more unsaturated monomers using the catalyst compound, as well as the oligomers and/or polymers produced therefrom are also provided.

40 Claims, No Drawings

(56) References Cited

OTHER PUBLICATIONS

Luks et al., "*The Template Synthesis and Characterization of New Mono- and Dinuclear Podand Schiff Base Complexes of Scandium Group Elements*", Collection of Czechoslovak Chemical Communications, 1988, vol. 63, No. 3, pp. 371-377.

Paolucci et al, "*Tridentate [N, N, O] Schiff:base group 4 metal complexes: Synthesis, structural characterization and reactivity in olefin polymerization*", Journal of Molecular Catalysis. A, Chamical, Elsevier, 2006, vol. 258, No. 1-2, pp. 275-283.

Inoue et al., "Ethylene Polymerization Behavior of New Titanium Complexes Having Two Phenoxy-Pyridine Chelate Ligands," Chemical Letters, 2001, vol. 30, No. 10, pp. 1060-1061.

Ihori et al., "Chiral Zirconium Catalysts Using Multidentate BINOL Derivatives for Catalytic Enantioselective Mannich-Type Reactions; Ligand Optimization and Approaches to Elucidation of the Catalyst Structure," Journal of the American Chemical Society, vol. 127, No. 44, 2005, pp. 15528-15535.

Oakes et al., "The surprisingly beneficial effect of soft donors on the performance of early transition metal olefin polymerization catalysts," Chem. Commun , 2004, pp. 2174-2175.

Takeuchi et al., "Bulky Titanium Bis(phenolate) Complexes as Novel Initiators for Living Anionic Polymerization of $\epsilon$—Caprolactone," Macromolecules, vol. 33, No. 3, 2000, pp. 725-729.

Tang et al., "Helical Polyguanidines Prepared by Helix-Sense-Selective Polymerizations of Achiral Carbodiimides Using Enantiopure Binaphthol-Based Titanium Catalysts," Macromolecules, vol. 40, No. 10, 2007, pp. 3575-3580.

Rath, et al., "Transfer Hydrogenation of Acetophenone Promoted by (Arene)Ruthenium(II) Reduced Schiff Base Complexes: an X-ray Structure of [($\eta^6$-$p$-cymene)RuCl(OC$_6$H$_4$-2-CH$_2$NHC$_6$H$_4$-$p$-Me)]", Polyhedron, 2001, 20, pp. 2735-2739.

Wong, et al., "New Chloro, $\mu$-Oxo, and Alkyl Derivatives of Dioxomolybdenum(VI) and—Tungsten(VI) Complexes Chelated with N$_2$O Tridentate Ligands: Synthesis and Catalytic Activities Toward Olefin Epoxidation", Inorganic Chemistry, 2002, 41, 5276-5285.

\* cited by examiner

CATALYST COMPOUNDS AND USE THEREOF

PRIORITY CLAIM

This application claims priority to and the benefit of U.S. Ser. No. 61/255,725, filed Oct. 28, 2009 and EP 09178615.2, filed Dec. 10, 2009.

CROSS REFERENCE TO RELATED APPLICATIONS

This application is related to U.S. Ser. No. 61/255,742, filed Oct. 28, 2009; U.S. Ser. No. 61/255,725, filed Oct. 28, 2009; U.S. Ser. No. 61/255,706, filed Oct. 28, 2009; and U.S. Ser. No. 61/255,750, filed Oct. 28, 2009. This application is also related to:

1) U.S. Ser. No. 12/908,522, filed Oct. 20, 2010 claiming priority to U.S. Ser. No. 61/255,750, filed Oct. 28, 2009;
2) U.S. Ser. No. 12/908,257, filed Oct. 20, 2010 claiming priority to U.S. Ser. No. 61/255,742, filed Oct. 28, 2009;
3) U.S. Ser. No. 12/908,550, filed Oct. 20, 2010 claiming priority to U.S. Ser. No. 61/255,725, filed Oct. 28, 2009; and
4) U.S. Ser. No. 12/908,615, filed Oct. 20, 2010 claiming priority to U.S. Ser. No. 61/255,758, filed Oct. 28, 2009.

FIELD OF THE INVENTION

This invention relates to catalyst compounds useful for polymerization and or oligomerization of unsaturated monomers, such as olefins.

BACKGROUND OF THE INVENTION

Various processes and catalysts exist for the homopolymerization or copolymerization of olefins. New polymerization catalysts are of interest in the industry because they offer many new opportunities for providing new processes and products to the markets in a cheaper and more efficient manner.

References of general interest related to the instant invention include: WO 2000/020427, WO 2001/010875, WO 2003/054038, US Patent Publication 20080182952, Polymer International, (2002) 51 (12), 1301-1303, Collection of Czechoslovak Chemical Communications (1988), 63(3), 371-377, and Transition Metal Chemistry (London) (1988) 23 (5), 609-613.

There is a need, therefore, for new polymerization technology, catalysts and products produced therefrom that are based on new transition metal catalyst compounds.

SUMMARY OF THE INVENTION

Group 4 catalyst compounds containing di-anionic tridentate nitrogen/oxygen based ligands are provided. The catalyst compounds are useful, with or without activators, to polymerize olefins, particularly α-olefins, or other unsaturated monomers. Systems and processes to oligomerize and/or polymerize one or more unsaturated monomers using the catalyst compound, as well as the oligomers and/or polymers produced therefrom are also provided. For the purposes of this disclosure, "α-olefins" includes ethylene.

The catalyst compounds can be represented by the following structures:

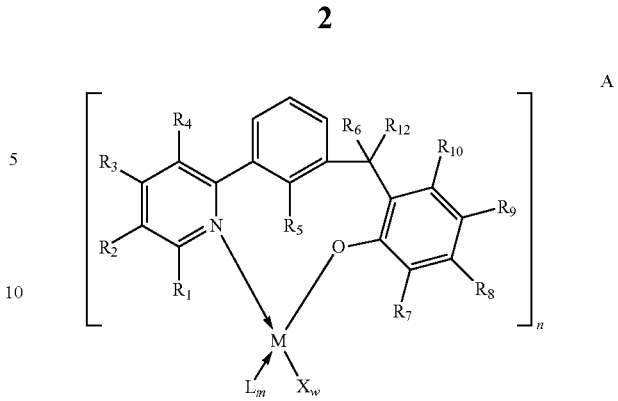

A

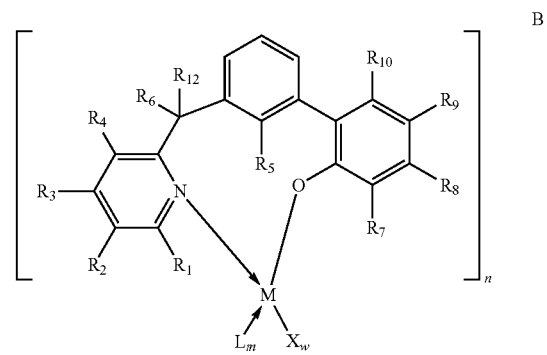

B

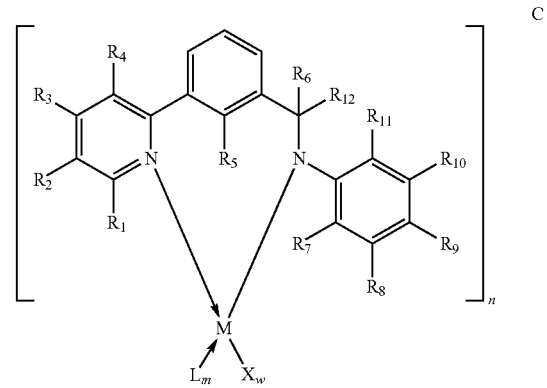

C

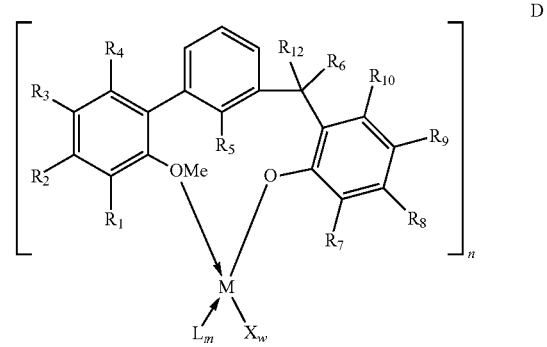

D

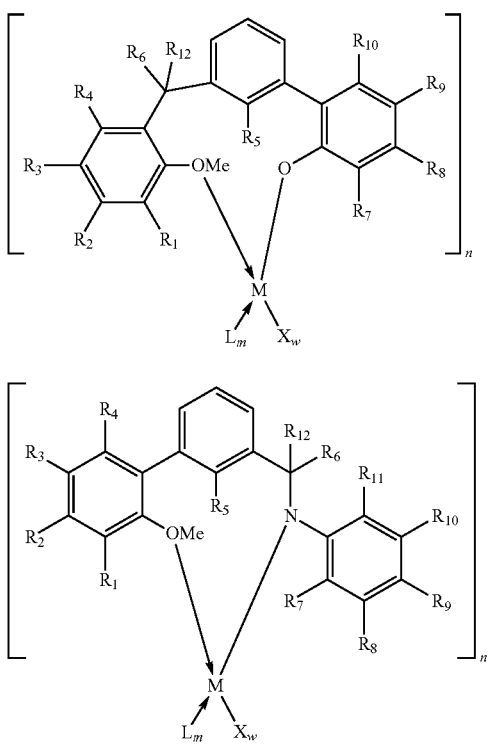

wherein
each X is, independently, a hydride, a halogen, a hydrocarbyl, a substituted hydrocarbyl, a halocarbyl, or a substituted halocarbyl;

w is 0, 1, 2 or 3;

each $R^1, R^2, R^3, R^4, R^5, R^6, R^7, R^8, R^9, R^{10}, R^{12}$ and $R^{11}$ if present, is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl, a halogen, an alkoxide, a sulfide, an amide, a phosphide, a silyl or another anionic heteroatom-containing group; or independently, may join together to form a $C_4$ to $C_{62}$ cyclic or polycyclic ring structure;

L is a neutral ligand bonded to M that may include molecules such as but not limited to pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, styrene, and the like;

M is a group 4 metal, preferably Hf, Zr or Ti;

m is 0, 1 or 2 and indicates the absence or presence of L; and n is 1 or 2.

In one particular embodiment, n is 1 and w is 2 or 3.

In another embodiment, it is possible that where $R^5$ is a hydrogen atom in the ligand, the carbon bonded to $R^5$ may or may not react with M such that an anionic ligand X is eliminated in the form of HX to form a bond between the carbon atom at the $R^5$ site and M such that w=2, 1 or 0 which is dependent on "n".

In still another embodiment, the present invention provides catalyst compositions which include one or more of the above-described catalyst compounds and one or more activators.

Definitions

In the structures depicted throughout this specification and the claims, a solid line indicates a bond, and an arrow indicates that the bond may be dative.

As used herein, the new notation for the Periodic Table Groups is used as described in CHEMICAL AND ENGINEERING NEWS, 63(5), 27 (1985).

Neutral ligands are defined as ligands that are neutral, with respect to charge, when formally removed from the metal in their closed shell electronic state. Neutral ligands contain at least one lone pair of electrons, pi-bond or sigma bond that are capable of binding to the transition metal. Neutral ligands may also be polydentate when more than one neutral ligand is connected via a bond or a hydrocarbyl, substituted hydrocarbyl or a functional group tether. A neutral ligand may be a substituent of another metal complex, either the same or different, such that multiple complexes are bound together.

Anionic ligands are defined as ligands that are anionic, with respect to charge, when formally removed from the metal in their closed shell electronic state. Anionic ligands include hydride, halide, hydrocarbyl, substituted hydrocarbyl or functional group. Non-limiting examples of anionic ligands include hydride, fluoride, chloride, bromide, iodide, alkyl, aryl, alkenyl, alkynyl, allyl, benzyl, acyl, trimethylsilyl. Anionic ligands may also be polydentate when more than one anionic ligand is connected via a bond or a hydrocarbyl, substituted hydrocarbyl or a functional group tether. An anionic ligand may be a substituent of another metal complex, either the same or different, such that multiple complexes are bound together. A mono-anionic ligand is defined to be an anionic ligand that has a −1 charge. A di-anionic ligand is defined to be an anionic ligand that has a −2 charge.

The terms "hydrocarbyl radical," "hydrocarbyl" and hydrocarbyl group" are used interchangeably throughout this document. Likewise the terms "group" and "substituent" are also used interchangeably in this document. For purposes of this disclosure, "hydrocarbyl radical" is defined to be $C_1$-$C_{100}$ radicals, that may be linear, branched, or cyclic (aromatic or non-aromatic); and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as O, S, Se, Te, $NR^*$, $PR^*$, $AsR^*$, $SbR^*$, $BR^*$, $SiR^*_2$, $GeR^*_2$, $SnR^*_2$, $PbR^*_2$ and the like, where $R^*$ is independently a hydrocarbyl or halocarbyl radical.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as O, S, Se, Te, $NR^*$, $PR^*$, $AsR^*$, $SbR^*$, $BR^*$, $SiR^*_2$, $GeR^*_2$, $SnR^*_2$, $PbR^*_2$ and the like where $R^*$ is independently a hydrocarbyl or halocarbyl radical provided that at least one halogen atom remains on the original halocarbyl radical.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where $R^*$ is independently a hydrocarbyl or halocarbyl radical as defined above and two or more $R^*$ may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^5_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where $R^*$ is independently a hydrocarbyl or halocarbyl radical as defined above and two or more $R^*$ may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where $R^*$ is independently a hydrocarbyl, substituted hydrocarbyl, halocarbyl or substituted halocarbyl radical as defined above and two $R^*$ may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tent-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-l-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

In the context of this document, "homopolymerization" would produce a polymer made from one monomer. For example, homopolymerization of propylene would produce homopolypropylene. Homopolymerization of ethylene would produce homopolyethylene. It should be noted, however, that some of the catalysts of this invention homopolymerize ethylene or propylene to non-traditional "polyethylene" and "polypropylene" structures, respectively. Likewise, "copolymerization" would produce polymers with more than one monomer type. For example, ethylene copolymers include polymers of ethylene with α-olefins, cyclic olefins and diolefins, vinylaromatic olefins, α-olefinic diolefins, substituted α-olefins, and/or acetylenically unsaturated monomers. Non-limiting examples of α-olefins include propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3 -divinylcyclohexane, 1,4-divinylcyclohexane, 1,5 -divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of α-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene. Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and -silicon atoms such as for example B, O, S, Se, Te, N, P, Ge, Sn, Pb, As, F, Cl, Br, or I, are contemplated, where such non-carbon or -silicon moieties are sufficiently far removed from the double bond so as not to interfere with the coordination polymerization reaction with the catalyst and so to retain the generally hydrocarbyl characteristic. By being sufficiently far removed from the double bond we intend that the number of carbon atoms, or the number of carbon and silicon atoms, separating the double bond and the non-carbon or -silicon moiety may be 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or -silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. All documents cited herein are incorporated by reference for purposes of all jurisdictions where such practice is allowed. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the monomer(s) used in the oligomerization or polymerization reaction. For example, the mer of polyethylene would be ethylene.

The terms "catalyst" and "catalyst compound" are defined to mean a compound capable of initiating catalysis. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. The term "catalyst system" is defined to mean: 1) a catalyst precursor/activator pair, and or 2) a catalyst compound capable of initiating catalysis without an activator. When "catalyst system" is used to describe such a pair before activation, it means the unactivated catalyst (pre-catalyst) together with an activator and, optionally, a co-activator. When it is used to describe such a pair after activation, it means the activated catalyst and the activator or other charge-balancing moiety.

The catalyst compound may be neutral as in a pre-catalyst or a catalyst system not requiring an activator, or may be a charged species with a counter ion as in an activated catalyst system.

The terms "activator" and "cocatalyst" are used interchangeably herein. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the catalyst compound to form an alkylated catalyst compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

DETAILED DESCRIPTION OF THE INVENTION

This invention relates to Group 4 dialkyl compounds supported by a pyridyl-aryl-phenoxy ("PAP"), a pyridyl-aryl-amido ("PAA"), an anisole-aryl-phenoxy ("AAP") or an anisole-aryl-amido ("AAA) tridentate ligand. Such compounds can polymerize ethylene to produce polyethylene. The catalyst compounds can be represented by the following structures:

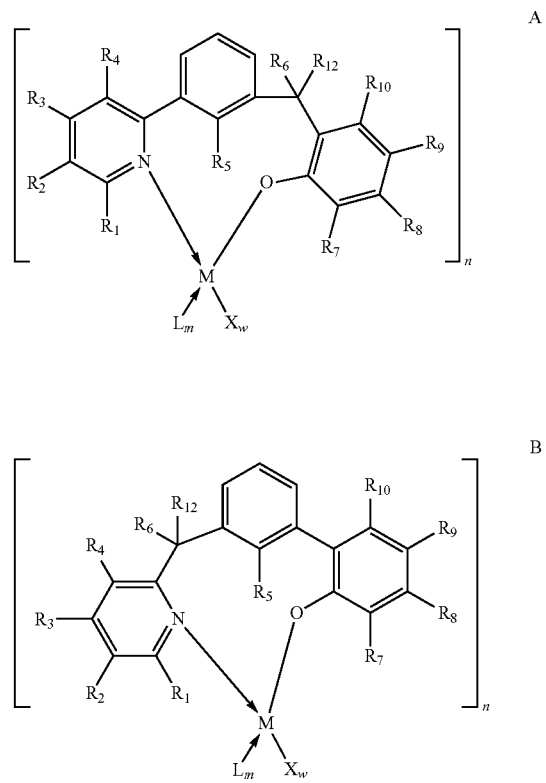

-continued

C
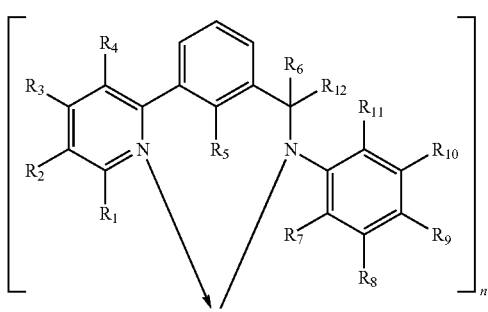

D
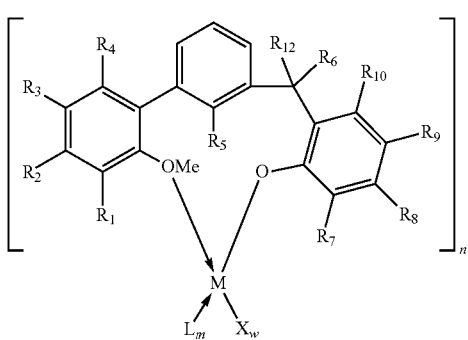

E
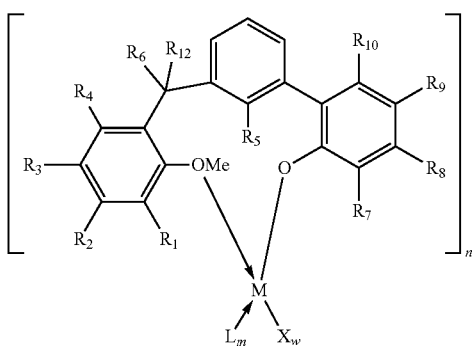
or

F
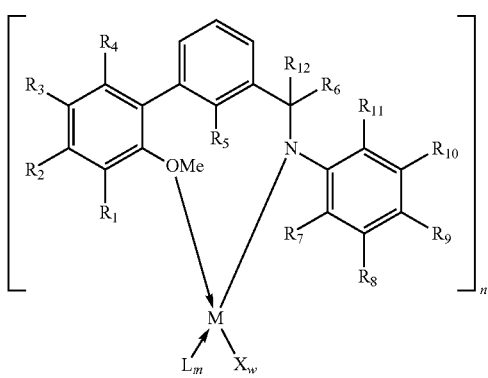

wherein
each X is, independently, a hydride, a halogen, a hydrocarbyl, a substituted hydrocarbyl, a halocarbyl, or a substituted halocarbyl;
w is 0, 1, 2 or 3;
each $R^1$, $R^2$, $R^3$, $R^4$, $R^5$, $R^6$, $R^7$, $R^8$, $R^9$, $R^{10}$, $R^{12}$ and $R^{11}$ if present, is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl, a halogen, an alkoxide, a sulfide, an amide, a phosphide, a silyl or another anionic heteroatom-containing group; or independently, may join together to form a $C_4$ to $C_{62}$ cyclic or polycyclic ring structure;

L is a neutral ligand bonded to M that may include molecules such as but not limited to pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, styrene, and the like;

M is a group 4 metal, preferably Hf, Zr or Ti;

m is 0, 1 or 2 and indicates the absence or presence of L; and n is 1 or 2.

In one particular embodiment, X, $R^1$, $R^2$, $R^3$, $R^4$, $R^5$, $R^6$, $R^7$, $R^8$, $R^9$, $R^{10}$, $R^{11}$, $R^{12}$, L M, and m are as defined above and n is 1 and w is 2 or 3. Such catalyst compounds can be represented by the structures:

$A^1$
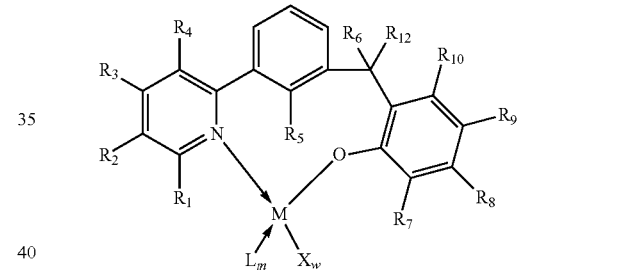

$B^1$
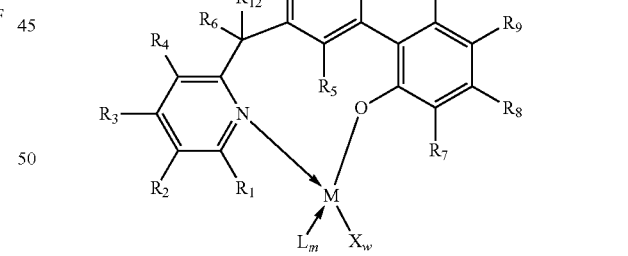

$C^1$
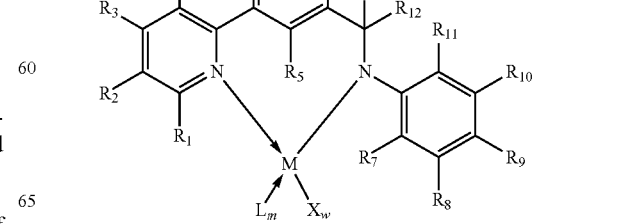

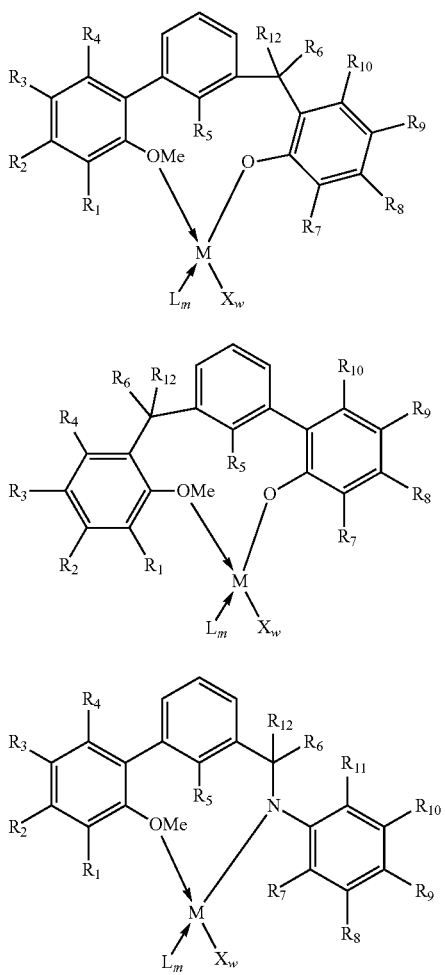

In another embodiment, it is possible that where $R^5$ is a hydrogen atom in the ligand, the carbon bonded to $R^5$ may or may not react with M such that an anionic ligand X is eliminated in the form of HX to form a bond between the carbon atom at the $R^5$ site and M such that w=2, 1 or 0 which is dependent on "n".

In one aspect, each $R^1$, $R^2$, $R^3$, $R^4$, $R^5$, $R^6$, $R^7$, $R^8$, $R^9$, $R^{10}$, $R^{12}$ and $R^{11}$ if present, is, independently, a hydrogen, a $C_1$ to $C_{30}$ hydrocarbyl, a $C_1$ to $C_{30}$ substituted hydrocarbyl, a $C_1$ to $C_{30}$ halocarbyl, a $C_1$ to $C_{30}$ substituted halocarbyl, a halogen, an alkoxide, a sulfide, an amide, a phosphide, a silyl or another anionic heteroatom-containing group; or independently, may join together to form a $C_4$ to $C_{62}$ cyclic or polycyclic ring structure.

In another aspect, each $R^1$, $R^2$, $R^3$, $R^4$, $R^5$, $R^6$, $R^7$, $R^8$, $R^9$, $R^{10}$, $R^{12}$ and $R^{11}$ if present, independently, a hydrogen, a $C_1$ to $C_{10}$ hydrocarbyl, a $C_1$ to $C_{10}$ substituted hydrocarbyl, a $C_1$ to $C_{10}$ halocarbyl, a $C_1$ to $C_{10}$ substituted halocarbyl, a halogen, an alkoxide, a sulfide, an amide, a phosphide, a silyl or another anionic heteroatom-containing group; or independently, may join together to form a $C_4$ to $C_{62}$ cyclic or polycyclic ring structure.

In still another aspect, each $R^1$, $R^2$, $R^3$, $R^4$, $R^5$, $R^6$, $R^7$, $R^8$, $R^9$, $R^{10}$, $R^{12}$ and $R^{11}$ if present, is, independently, a hydrogen, a $C_1$ to $C_{30}$ hydrocarbyl, a $C_1$ to $C_{30}$ substituted hydrocarbyl, a $C_1$ to $C_{30}$ halocarbyl, a $C_1$ to $C_{30}$ substituted halocarbyl, a halogen, an alkoxide, a sulfide, an amide, a phosphide, a silyl or another anionic heteroatom-containing group; or independently, may join together to form a $C_4$ to $C_{62}$ cyclic or polycyclic ring structure and $R^6$ is a hydrogen, a $C_3$ to $C_{50}$ hydrocarbyl or a $C^3$ to $C_{50}$ halocarbyl.

In one aspect, at least one of $R^6$ or $R^{12}$ is not a hydrogen atom.

In one embodiment, X can be selected from fluoride, chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl, trimethylsilylmethyl, bis(trimethylsilyl)methyl, methoxy, ethoxy, propoxy, butoxy, dimethylamido, diethylamido, methylethylamido, phenoxy, benzoxy, or allyl.

In another embodiment, L can be selected from pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, or styrene.

In specific embodiments of the catalyst compound, $R^6$ can be phenyl, p-tolyl or methyl and $R^7$ can be phenyl or t-butyl and various combinations thereof.

Activators and Catalyst Activation

The catalyst compound can be combined with one or more co-catalysts or activators. Activators that can be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; ionic activators include dimethylanilinium tetrakis perfluorophenyl borate, triphenyl carbonium tetrakis perfluorophenyl borate, dimethylanilinium tetrakis perfluorophenyl aluminate, and the like.

The alumoxane component useful as an activator typically is an oligomeric aluminum compound represented by the general formula $(R^x-Al-O)_n$, which is a cyclic compound, or $R^x(R^x-Al-O)_nAlR^x_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators (at times used in combination with a co-activator) may be used in the practice of this invention. Preferably, discrete ionic activators such as [Me$_2$PhNH][B(C$_6$F$_5$)$_4$], [Ph$_3$C][B(C$_6$F$_5$)$_4$], [Me$_2$PhNH][B((C$_6$H$_3$-3,5-(CF$_3$)$_2$))$_4$], [Ph$_3$C][C((C$_6$H$_3$-3,5-(CF$_3$)$_2$))$_4$], [NH$_4$][B(C$_6$H$_5$)$_4$] or Lewis acidic activators such as B(C$_6$F$_5$)$_3$ or B(C$_6$H$_5$)$_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

An ionizing or stoichiometric activator, neutral or ionic, such as tri(n-butyl) ammonium tetrakis(pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof can also be used. Examples of neutral stoichiometric activators include tri-substituted boron, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299, and 5,502,124, and U.S. Ser. No. 08/285,380, filed Aug. 3, 1994, all of which are herein fully incorporated by reference.

Ionic catalysts can be prepared by reacting a catalyst compound with an activator, such as B(C$_6$F$_6$)$_3$, which upon reaction with the hydrolyzable ligand (X') of the catalyst compound forms an anion, such as ([B(C$_6$F$_5$)$_3$(X')]$^-$), which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems include a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic, diolefinic and acetylenically unsaturated substrates or other neutral Lewis bases such as ethers, nitriles and the like. Two classes of compatible non-coordinating anions have been disclosed in EP 0 277,003 and EP 0 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

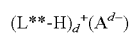

wherein L** is an neutral Lewis base;
H is hydrogen;
(L**-H)$^+$ is a Bronsted acid;
A$^{d-}$ is a non-coordinating anion having the charge d–; and
d is an integer from 1 to 3.

The cation component, (L**-H)$_d^+$ may include Bronsted acids such as protons or protonated Lewis bases or reducible Lewis acids capable of protonating or abstracting a moiety, such as an alkyl or aryl, from the pre-catalyst after alkylation.

The activating cation (L-H)$_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation (L-H)$_d^+$ may also be a moiety such as silver, tropylium, carbeniums, ferroceniums and mixtures, preferably carboniums and ferroceniums; most preferably triphenyl carbonium.

The anion component A$^{d-}$ include those having the formula [M$^{k+}$Q$_n$]$^{d-}$ wherein k is an integer from 1 to 3; n is an integer from 2-6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl) ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, trimethylammonium tetrakis-(2, 3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl (tert-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3, 4,6-tetrafluorophenyl)borate, N,N-dimethyl-(2,4,6- trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis (3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium) tetrakis(3,5-bis(trifluoromethyl)phenyl)borate.

Most preferably, the ionic stoichiometric activator ($L^{**}-H)_d^+ (A^{d-}$) is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Invention catalyst precursors can also be activated with cocatalysts or activators that comprise non-coordinating anions containing metalloid-free cyclopentadienide ions. These are described in US Patent Publication 2002/0058765 A1, published on 16 May 2002, and for the instant invention, require the addition of a co-activator to the catalyst pre-cursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral catalyst compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

Cocatalyst compounds or activator compounds that are initially neutral Lewis acids but form a cationic metal complex and a noncoordinating anion, or a zwitterionic complex upon reaction with the alkylated catalyst compounds can also be used. The alkylated invention compound is formed from the reaction of the catalyst pre-cursor and the co-activator. For example, tris(pentafluorophenyl) boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878, 5,486,632, and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.,* 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl) boron, and mixtures of trimethyl aluminum with dimethylanilinium tetrakis(pentafluorophenyl)borate or tris(pentafluorophenyl)boron.

In some embodiments, scavenging compounds are used with stoichiometric activators. Typical aluminum or boron alkyl components useful as scavengers are represented by the general formula $R^xJZ_2$ where J is aluminum or boron, $R^x$ is a hydrocarbyl group (such as a C1 to C20 alkyl), and each Z is independently $R^x$ or a different univalent anionic ligand such as halogen (Cl, Br, I), alkoxide ($OR^x$) and the like. Most preferred aluminum alkyls include triethylaluminum, diethylaluminum chloride, tri-iso-butylaluminum, tri-n-octylaluminum. tri-n-hexylaluminum, trimethylaluminum and the like. Preferred boron alkyls include triethylboron. Scavenging compounds may also be alumoxanes and modified alumoxanes including methylalumoxane and modified methylalumoxane.

Supported Catalysts

The catalyst compound(s) can be supported or non-supported. To prepare uniform supported catalysts, the catalyst or catalyst precursor preferably dissolves in the chosen solvent. The term "uniform supported catalyst" means that the catalyst, or the catalyst precursor and the activator, and or the activated catalyst approach uniform distribution upon the support's accessible surface area, including the interior pore surfaces of porous supports. Some embodiments of supported catalysts prefer uniform supported catalysts; other embodiments show no such preference.

Invention supported catalyst systems may be prepared by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100% to 200% of the pore volume). The mixture is optionally heated from 30° C.-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100% to 200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a polymerization process's liquid phase. For example, a solution of catalyst precursor may be mixed with a support material for a period of about 1 minute to 10 hours. The resulting pre-catalyst mixture may be filtered from the solution and dried under vacuum, or evaporation alone removes the solvent. The total catalyst-precursor-solution volume may be greater than the support's pore volume, but some embodiments limit the total solution volume below that needed to form a gel or slurry (about 90% to 400%, preferably about 100% to 200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Invention catalyst carriers may have a surface area of from 10-700 m²/g, a pore volume of 0.1-4.0 cc/g and an average particle size of 10-500 µm. Some embodiments select a surface area of 50-500 m²/g, a pore volume of 0.5-3.5 cc/g, or an average particle size of 20-200 µm. Other embodiments select a surface area of 100-400 m²/g, a pore volume of 0.8-3.0 cc/g, and an average particle size of 30-100 µm. Invention carriers typically have a pore size of 10-1000 Angstroms, alternatively 50-500 Angstroms, or 75-350 Angstroms.

Invention catalysts are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Invention catalysts can be supported for gas-phase, bulk, or slurry polymerization, or otherwise as needed. Numerous support methods are known for catalysts in the olefin polymerization art, particularly alumoxane-activated catalysts; all are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582, and 5,466,649, and international publications WO 93/11172 and WO 94/07928.

Monomers

The catalyst compounds can be used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methylpentene-1, 3-methylpentene-1, 3,5,5-trimethylhexene-1, and 5-ethylnonene-1.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, cyclopentadiene, cyclopentene, 4-methylcyclopentene, cyclohexene, 4-methylcyclohexene, cyclobutene, vinyladamantane, norbornene, 5-methylnorbornene, 5-ethylnorbornene, 5-propylnorbornene, 5-butylylnorbornene, 5-pentylnorbornene, 5-hexylnorbornene, 5-heptylnorbornene, 5-octylnorbornene, 5-nonylnorbornene, 5-decylnorbornene, 5-phenylnorbornene, vinylnorbornene, ethylidene norbornene, 5,6-dimethylnorbornene, 5,6-dibutylnorbornene and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha-omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

Non-limiting examples of preferred polar unsaturated monomers useful in this invention, particularly with group 4 and 6 metal compounds, include nitro substituted monomers including 6-nitro-1-hexene; amine substituted monomers including N-methylallylamine, N-allylcyclopentylamine, and N-allyl-hexylamine; ketone substituted monomers including methyl vinyl ketone, ethyl vinyl ketone, and 5-hexen-2-one; aldehyde substituted monomers including acrolein, 2,2-dimethyl-4-pentenal, undecylenic aldehyde, and 2,4-dimethyl-2,6-heptadienal; alcohol substituted monomers including allyl alcohol, 7-octen-1-ol, 7-octene-1,2-diol, 10-undecen-1-ol, 10-undecene-1,2-diol, 2-methyl-3-buten-1-ol; acetal, epoxide and or ether substituted monomers including 4-hex-5-enyl-2,2-dimethyl-[1,3]dioxolane, 2,2-dimethyl-4-non-8-enyl-[1,3]dioxolane, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, 11-methoxyundec-1-ene, and 8-methoxyoct-1-ene; sulfur containing monomers including allyl disulfide; acid and ester substituted monomers including acrylic acid, vinylacetic acid, 4-pentenoic acid, 2,2-dimethyl-4-pentenoic acid, 6-heptenoic acid, trans-2,4-pentadienoic acid, 2,6-heptadienoic acid, methyl acrylate, ethyl acrylate, tert-butyl acrylate, n-butyl acrylate, methacrylic acid, methyl methacrylate, ethyl methacrylate, tert-butyl methacrylate, n-butyl methacrylate, hydroxypropyl acrylate, acetic acid oct-7-enyl ester, non-8-enoic acid methyl ester, acetic acid undec-10-enyl ester, dodec-11-enoic acid methyl ester, propionic acid undec-10-enyl ester, dodec-11-enoic acid ethyl ester, and nonylphenoxypolyetheroxy acrylate; siloxy containing monomers including trimethyloct-7-enyloxy silane, and trimethylundec-10-enyloxy silane, polar functionalized norbornene monomers including 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.1$^{3,9}$.1$^{5,15}$.1$^{7,13}$]octasiloxane, 2-benzoyl-5-norbornene, 2-acetyl-5-norbornene, 7-synmethoxymethyl-5-norbornen-2-one, 5-norbornen-2-ol, and 5-norbornen-2-yloxy-trimethylsilane, and partially fluorinated monomers including nonafluoro-1-hexene, allyl-1,1,2,2,-tetrafluoroethyl ether, 2,2,3,3-tetrafluoronon-8-enoic acid ethyl ester, 1,1,2,2-tetrafluoro-2-(1,1,2,2-tetrafluoro-oct-7-enyloxy)-ethanesulfonyl fluoride, acrylic acid 2,2,3,3,4,4,5,5,6,6,7,7,8,8-pentadecafluoro-octyl ester, and 1,1,2,2-tetrafluoro-2-(1,1,2,2,3,3,4,4-octafluorodec-9-enyloxy)-ethanesulfonyl fluoride.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha-omega-dienes are used alone or in combination with mono-alpha olefins.

In a preferred embodiment the process described herein may be used to produce homopolymers or copolymers. For the purposes of this invention and the claims thereto a copolymer may comprise two, three, four or more different monomer units. Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the homopolymers or copolymers described, additionally comprise one or more diolefin comonomers, preferably one or more $C_4$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methylpentene-1, 3-methylpentene-1, 3,5,5-trimethylhexene-1, cyclopentene, 4-methylcyclopentene, cyclohexene, and 4-methylcyclohexene.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methylpentene-1, 3-methylpentene-1, and 3,5,5-trimethylhexene-1.

In a preferred embodiment, the polymer produced herein is a homopolymer of norbornene or a copolymer of norbornene and a substituted norbornene, including polar functionalized norbornenes.

In a preferred embodiment the copolymers described herein comprise at least 50 mole % of a first monomer and up to 50 mole % of other monomers.

In another embodiment, the polymer comprises a first monomer present at from 40 to 95 mole %, preferably 50 to 90 mole %, preferably 60 to 80 mole %, and a comonomer present at from 5 to 60 mole %, preferably 10 to 40 mole %, more preferably 20 to 40 mole %, and a termonomer present at from 0 to 10 mole %, more preferably from 0.5 to 5 mole %, more preferably 1 to 3 mole %.

In a preferred embodiment the first monomer comprises one or more of any $C_3$ to $C_8$ linear branched or cyclic alpha-olefins, including propylene, butene, (and all isomers thereof), pentene (and all isomers thereof), hexene (and all isomers thereof), heptene (and all isomers thereof), and octene (and all isomers thereof). Preferred monomers include propylene, 1-butene, 1-hexene, 1-octene, cyclopentene, cyclohexene, cyclooctene, hexadiene, cyclohexadiene and the like.

In a preferred embodiment the comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, undecene, dodecene, hexadecene, butadiene, hexadiene, heptadiene, pentadiene, octadiene, nonadiene, decadiene, dodecadiene, styrene, 3,5,5-trimethylhexene-1, 3-methylpentene-1, 4-methylpentene-1, cyclopentadiene, and cyclohexene.

In a preferred embodiment the polymers described above further comprise one or more dienes at up to 10 wt %, preferably at 0.00001 to 1.0 wt %, preferably 0.002 to 0.5 wt %, even more preferably 0.003 to 0.2 wt %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

The catalyst compounds can be used to polymerize and/or oligomerize one or more monomers using any one or more solution, slurry, gas-phase, and high-pressure polymerization processes. The catalyst compound and optional co-catalyst(s), can be delivered as a solution or slurry, either separately to a reactor, activated in-line just prior to a reactor, or preactivated and pumped as an activated solution or slurry to a reactor. Polymerizations can be carried out in either single reactor operations, in which monomer, comonomers, catalyst/activator/co-activator, optional scavenger, and optional modifiers are added continuously to a single reactor or in series reactor operations, in which the above components are added to each of two or more reactors connected in series. The catalyst components can be added to the first reactor in the series. The catalyst component may also be added to both reactors, with one component being added to first reaction and another component to other reactors. In one preferred embodiment, the pre-catalyst is activated in the reactor in the presence of olefin.

The catalyst compositions can be used individually or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

One or more scavenging compounds can be used. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157 and 5,241,025, and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-propyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$).

In terms of polymer density, the polymers capable of production in accordance with the invention, can range from about 0.85 to about 0.95, preferably from 0.87 to 0.93, more preferably 0.89 to 0.920. Polymer molecular weights can range from about 50,000 Mn to about 2,000,000 Mn or greater. Molecular weight distributions can range from about 1.1 to about 50.0, with molecular weight distributions from 1.2 to about 5.0 being more typical. Pigments, antioxidants and other additives, as is known in the art, may be added to the polymer.

Gas Phase Polymerization

Generally, in a fluidized gas bed process for producing polymers, a gaseous stream containing one or more monomers is continuously cycled through a fluidized bed in the presence of a catalyst under reactive conditions. The gaseous stream can be withdrawn from the fluidized bed and recycled back into the reactor. Simultaneously, polymer product can be withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661, and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to about 110° C., and most preferably in the range of from about 70° C. to about 95° C. In another embodiment when high density polyethylene is desired then the reactor temperature is typically between 70° C. and 105° C.

The productivity of the catalyst or catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818, and 5,677,375, and European publications EP-A-0 794 200, EP-A-0 802 202, and EP-B-0 634 421 all of which are herein fully incorporated by reference.

In another preferred embodiment the catalyst system is in liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psig to 735 psig, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process should be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art and described in, for instance U.S. Pat. No. 3,248,179; which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484; which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 wt %, preferably from about 2 to about 7 wt %, more preferably from about 2.5 to about 6 wt %, most preferably from about 3 to about 6 wt %.

Another process of the invention is where the process, preferably a slurry or gas phase process is operated in the absence of or essentially free of any scavengers, such as triethylaluminum, trimethylaluminum, tri-iso-butylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-iso-butyl aluminum and an excess of alumoxane or modified alumoxane.

Homogeneous, Bulk or Solution Phase Polymerization

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10-30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1-16,000 MPa), most preferably from 1.0 to 500 bar (10-5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or more than one reactor operated in series or parallel. These reactors may have or may not have internal cooling and the monomer feed may or may not be refrigerated. See the general disclosure of U.S. Pat. No. 5,001,205 for general process conditions. See also, international application WO 96/33227 and WO 97/22639.

Medium and High Pressure Polymerizations

In the high pressure process for the polymerization of ethylene alone or in combination with $C_3$ to $C_{10}$ alpha-olefins and optionally other copolymerizable olefins, the temperature of the medium within which the polymerization reaction occurs is at least 120° C. and preferably above 140° C. and may range to 350° C., but below the decomposition temperature of said polymer product, typically from 310° C. to 325° C. Preferably, the polymerization is completed at a temperature within the range of 130° C. to 230° C. The polymerization is completed at a pressure above 200 bar (20 MPa), and generally at a pressure within the range of 500 bar (50 MPa) to 3500 bar (350 MPa). Preferably, the polymerization is completed at a pressure within the range from 800 bar (80 MPa) to 2500 bar (250 MPa).

For medium pressure process, the temperature within which the polymerization reaction occurs is at least 80° C. and ranges from 80° C. to 250° C., preferably from 100° C. to 220° C., and should for a given polymer in the reactor, be above the melting point of said polymer so as to maintain the fluidity of the polymer-rich phase. The pressure can be varied between 100 and 1000 bar for ethylene homopolymers and from 30 bar (3 MPa) to 1000 bar (100 MPa), especially 50 bar (5 MPa) to 500 bar (50 MPa) for processes producing ethylene copolymers containing $C_3$ to $C_{10}$ olefins and optionally other copolymerizable olefins.

More recently, polymerization conditions for high pressure and or temperature polymerizations to prepare propylene homopolymers and copolymers of propylene with $C_3$ to $C_{10}$ olefins and optionally other copolymerizable olefins have been reported. See U.S. Ser. No. 60/431,185 filed Dec. 5, 2002; U.S. Ser. No. 60/431,077, filed Dec. 5, 2002; and U.S. Ser. No. 60/412,541, filed Sep. 20, 2002.

After polymerization and deactivation of the catalyst, the polymer product can be recovered by processes well known in the art. Any excess reactants may be flashed off from the polymer and the polymer obtained extruded into water and cut into pellets or other suitable comminuted shapes. For general process conditions, see the general disclosure of U.S. Pat. Nos. 5,084,534, 5,408,017, 6,127,497, and 6,255,410, which are incorporated herein by reference.

The following paragraphs enumerated consecutively from 1 through 28 provide for various aspects of the present invention. In one embodiment, in a first paragraph (1), the present invention provides a transition metal catalyst compound represented by one of the structures:

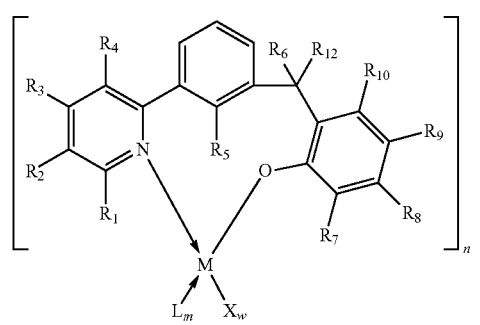

A

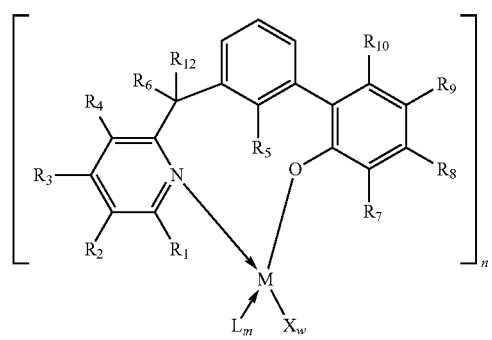

B

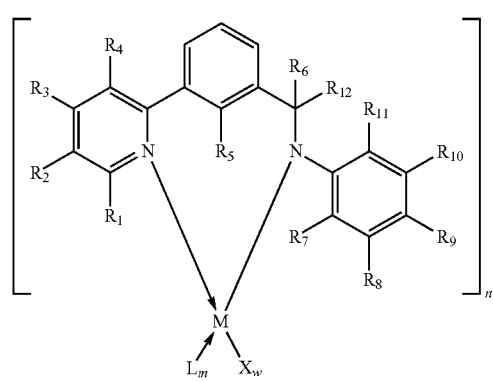

C

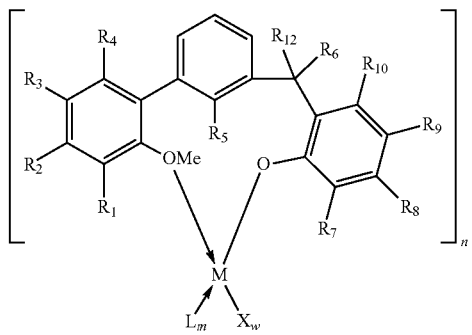

D

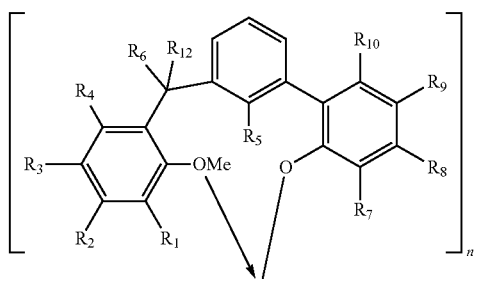

E or

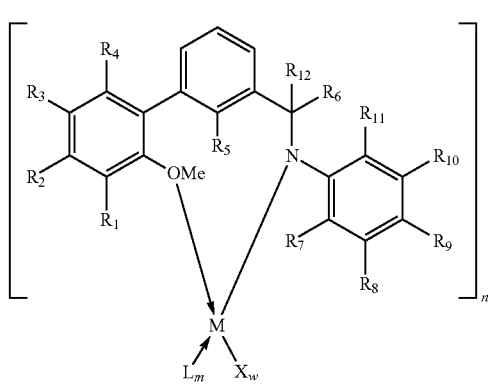

F wherein
each X is, independently, a hydride, a halogen, a hydrocarbyl, a substituted hydrocarbyl, a halocarbyl, or a substituted halocarbyl;
w is 0, 1, 2 or 3;
each $R^1$, $R^2$, $R^3$, $R^4$, $R^5$, $R^6$, $R^7$, $R^8$, $R^9$, $R^{10}$, $R^{12}$ and $R^{11}$ if present, is, independently, a hydrogen, a hydrocarbyl, a substituted hydrocarbyl, a halocarbyl, a substituted halocarbyl, a halogen, an alkoxide, a sulfide, an amide, a phosphide, a silyl or another anionic heteroatom-containing group, or independently, may join together to form a $C_4$ to $C_{62}$ cyclic or polycyclic ring structure;
L is a neutral ligand bonded to M that may include molecules such as but not limited to pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, styrene, and the like;
M is Hf, Zr or Ti;
m is 0, 1 or 2 and indicates the absence or presence of L; and
n is 1 or 2.

2. The compound according to paragraph 1, wherein the structure is C.
3. The compound according to either of paragraphs 1 or 2, wherein n is 1 and w is 2 or 3.
4. The compound according to any of paragraphs 1 through 3, wherein $R^6$ is phenyl or methyl and $R^7$ is phenyl or t-butyl.
5. The compound according to paragraph 1, wherein the structure is:

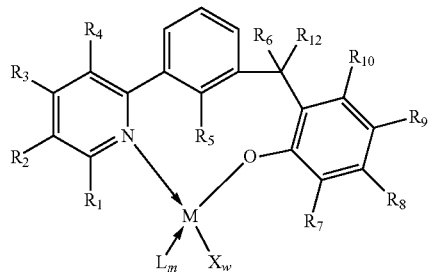

A¹

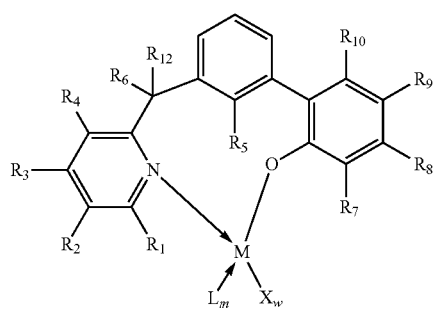

B¹

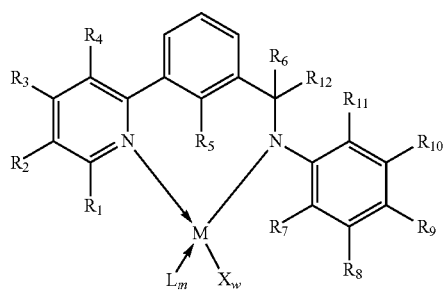

C¹

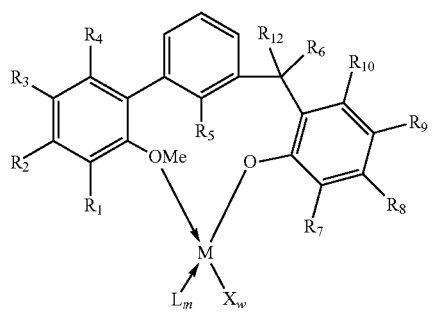

D¹

-continued

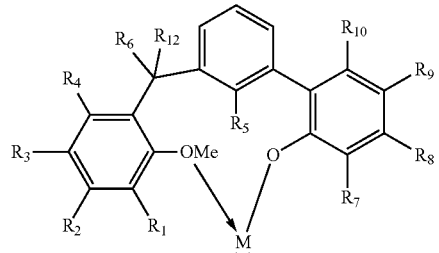

E¹ or

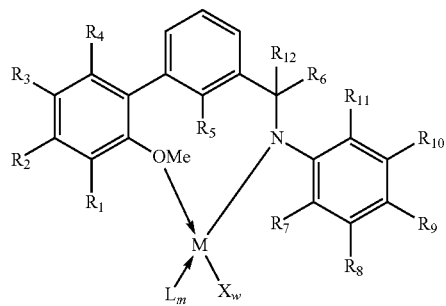

F¹ wherein n is 1 and w is 2 or 3.

6. A transition metal catalyst composition represented by one of the structures:

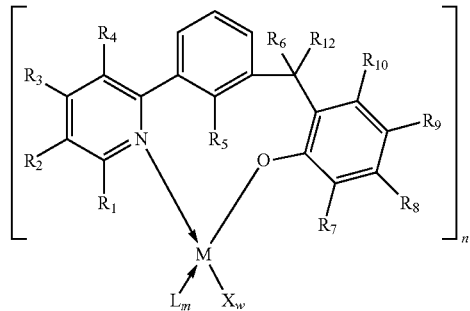

A

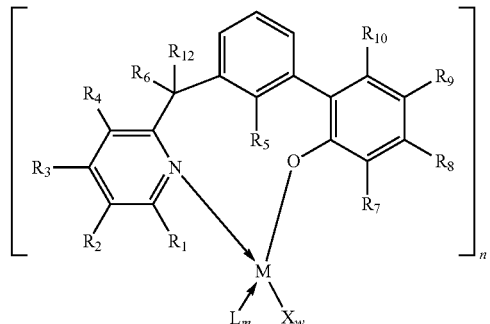

B

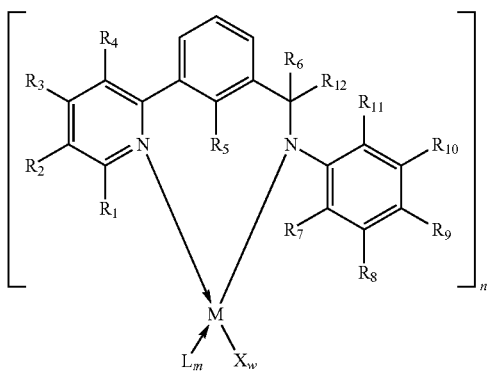

C

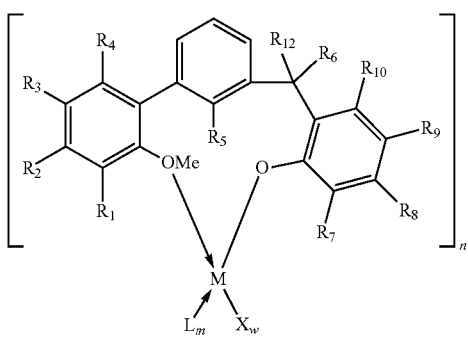

D

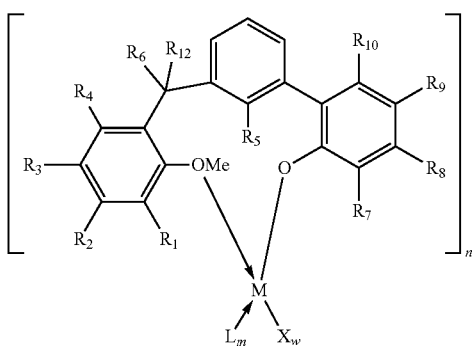

E

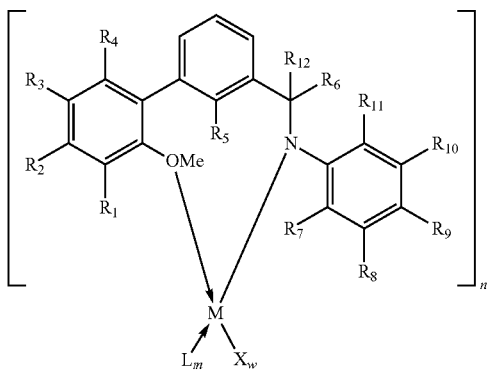

F wherein each X is, independently, a hydride, a halogen, a hydrocarbyl, a substituted hydrocarbyl, a halocarbyl, or a substituted halocarbyl;

w is 0, 1, 2 or 3;

each $R^1$, $R^2$, $R^3$, $R^4$, $R^5$, $R^6$, $R^7$, $R^8$, $R^9$, $R^{10}$, $R^{12}$ and $R^{11}$ if present, is, independently, a hydrogen, a hydrocarbyl, a substituted hydrocarbyl, a halocarbyl, a substituted halocarbyl, a halogen, an alkoxide, a sulfide, an amide, a phosphide, a silyl or another anionic heteroatom-containing group, or independently, may join together to form a $C_4$ to $C_{62}$ cyclic or polycyclic ring structure;

L is a neutral ligand bonded to M that may include molecules such as but not limited to pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, styrene, and the like;

M is Hf, Zr or Ti;

m is 0, 1 or 2 and indicates the absence or presence of L;

n is 1 or 2; and an activator.

7. The composition according to paragraph 6, wherein the structure is C.

8. The composition according to either of paragraphs 6 or 7, wherein n is 1 and w is 2 or 3.

9. The composition according to any of paragraphs 6 through 8, wherein $R^6$ is phenyl or methyl and $R^7$ is phenyl or t-butyl.

10. The composition according to paragraph 1, wherein the structure is:

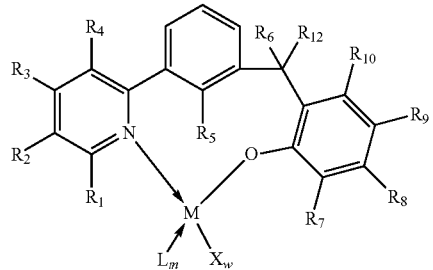

$A^1$

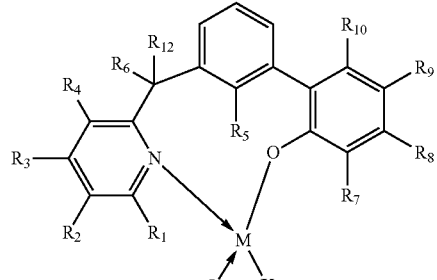

$B^1$

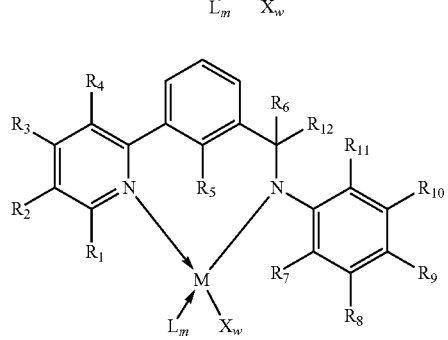

$C^1$

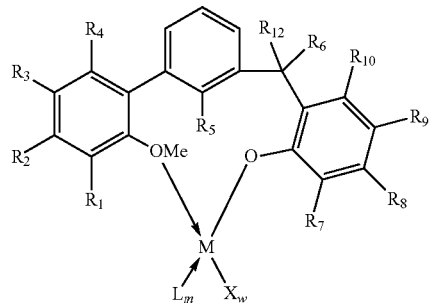
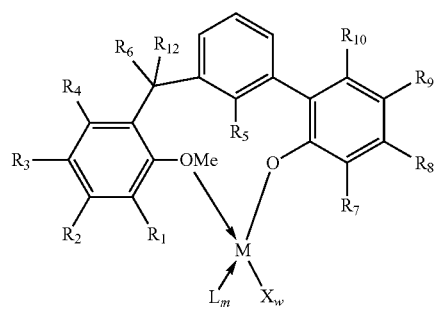
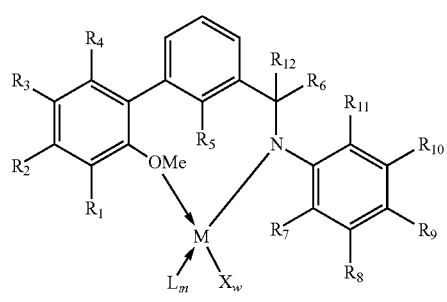
wherein n is 1 and w is 2 or 3.
11. A process for polymerization comprising:
contacting ethylene and optionally one or more unsaturated monomers with a catalyst compound represented by one of the structures:
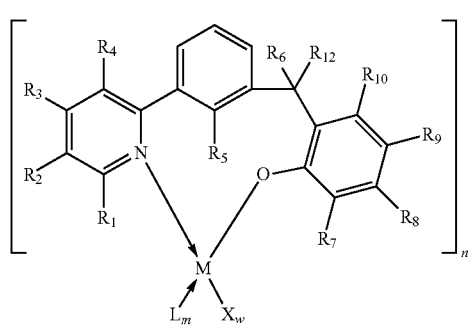
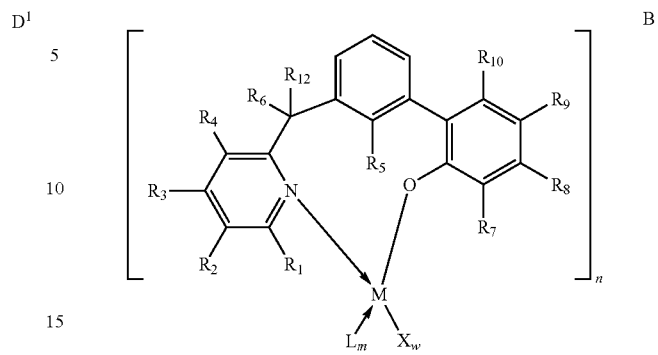
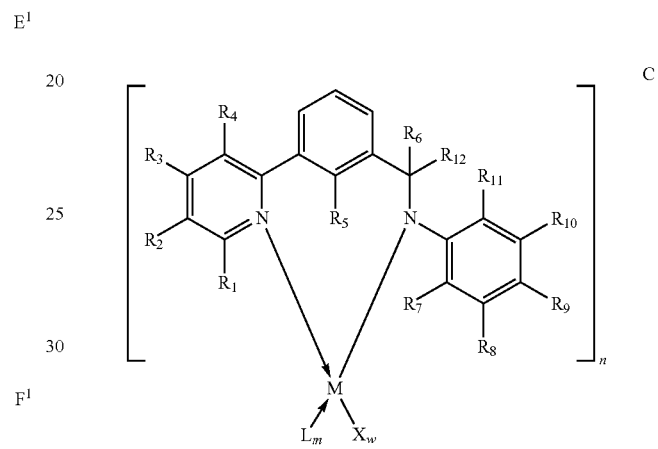
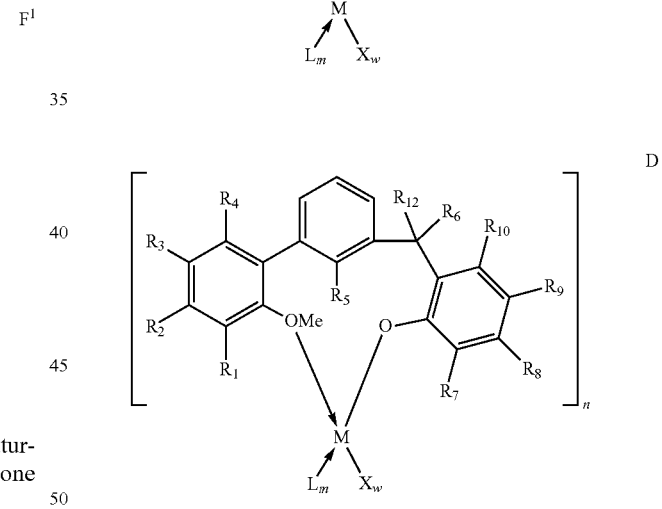
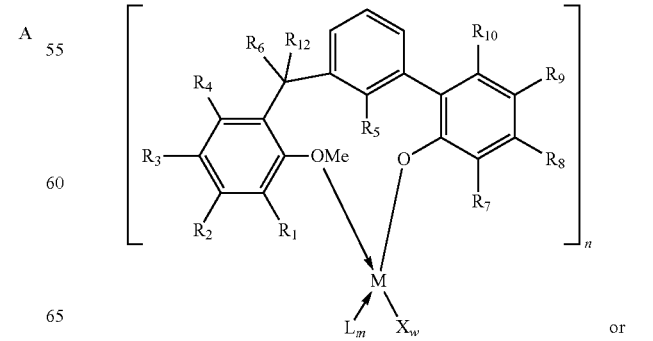
or

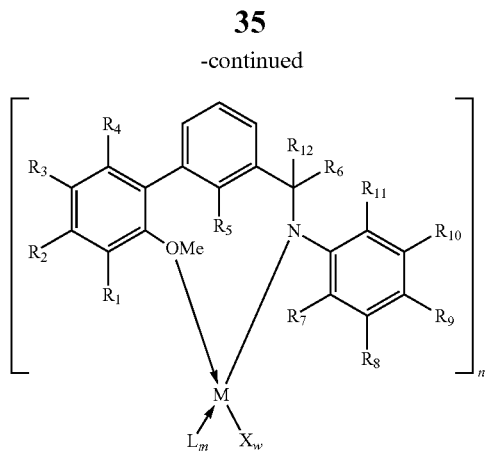

F wherein each X is, independently, a hydride, a halogen, a hydrocarbyl, a substituted hydrocarbyl, a halocarbyl, or a substituted halocarbyl;

w is 0, 1, 2 or 3;

each $R^1$, $R^2$, $R^3$, $R^4$, $R^5$, $R^6$, $R^7$, $R^8$, $R^9$, $R^{10}$, $R^{12}$ and $R^{11}$ if present, is, independently, a hydrogen, a hydrocarbyl, a substituted hydrocarbyl, a halocarbyl, a substituted halocarbyl, a halogen, an alkoxide, a sulfide, an amide, a phosphide, a silyl or another anionic heteroatom-containing group, or independently, may join together to form a $C_4$ to $C_{62}$ cyclic or polycyclic ring structure;

L is a neutral ligand bonded to M that may include molecules such as but not limited to pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, styrene, and the like;

M is Hf, Zr or Ti;

m is 0, 1 or 2 and indicates the absence or presence of L; and n is 1 or 2.

12. The process according to paragraph 11, wherein the structure is C.
13. The process according to either of paragraphs 11 or 12, wherein n is 1 and w is 2 or 3.
14. The process according to any of paragraphs 11 through 13, wherein $R^6$ is phenyl or methyl and $R^7$ is phenyl or t-butyl.
15. The process according to paragraph 11, wherein the structure is:

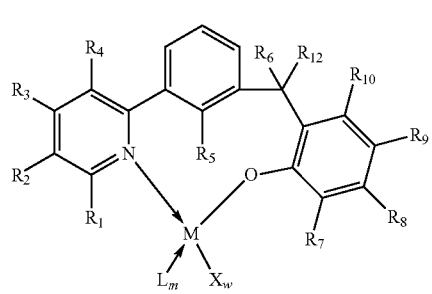

$A^1$

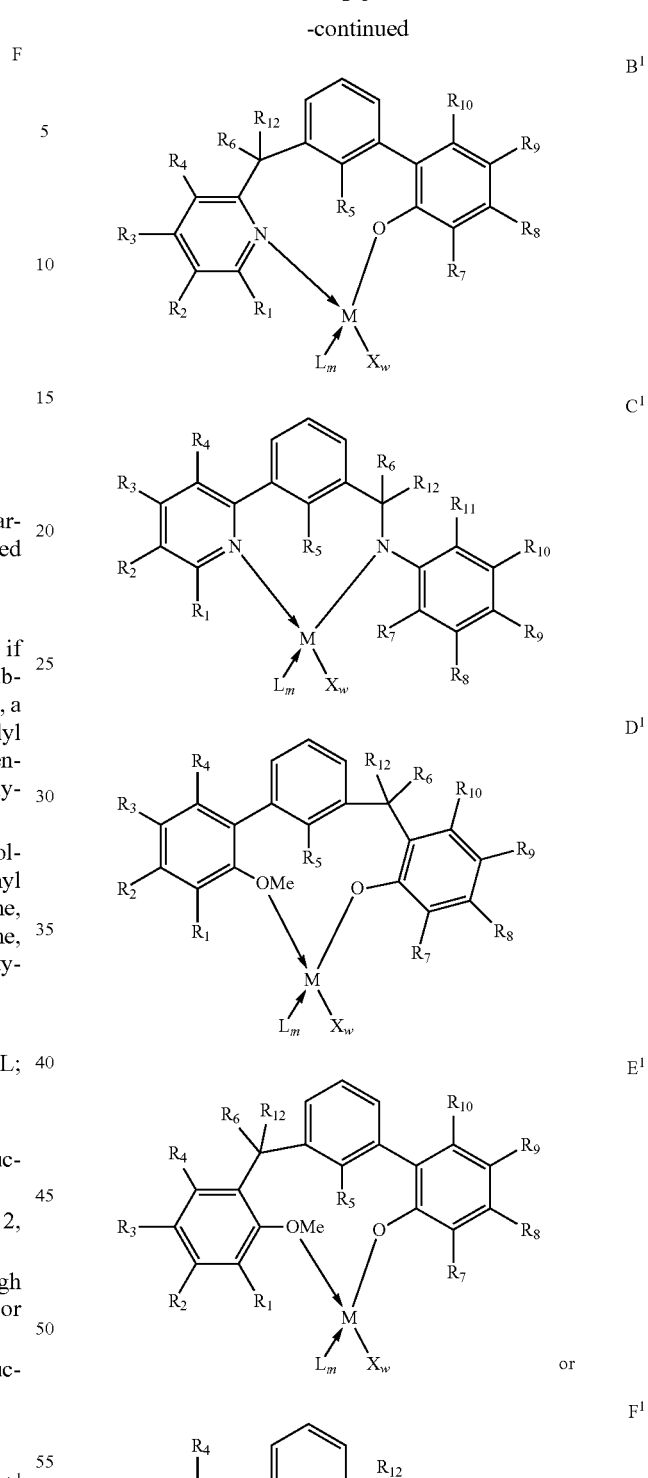

wherein n is 1 and w is 2 or 3.

16. A process for polymerization comprising:

contacting ethylene and optionally one or more unsaturated monomers with a transition metal catalyst composition represented by one of the structures:

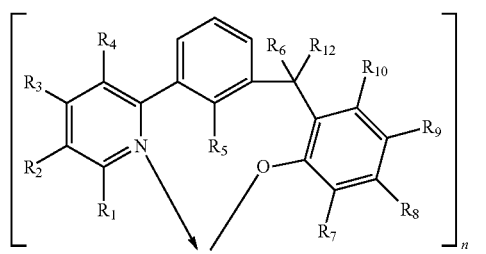

A

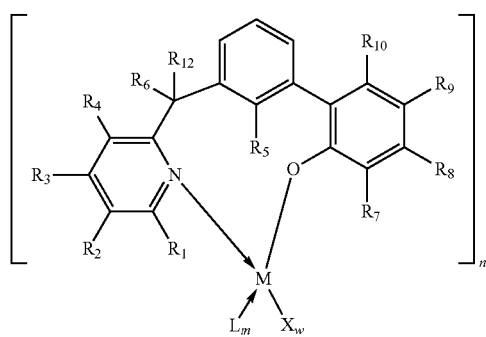

B

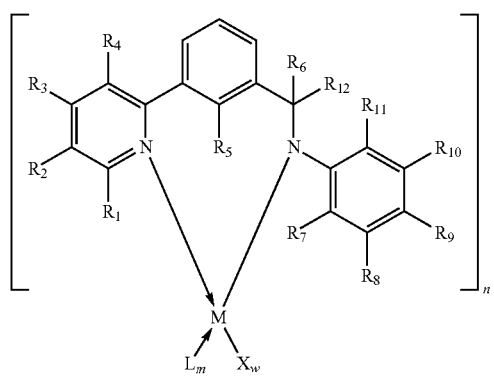

C

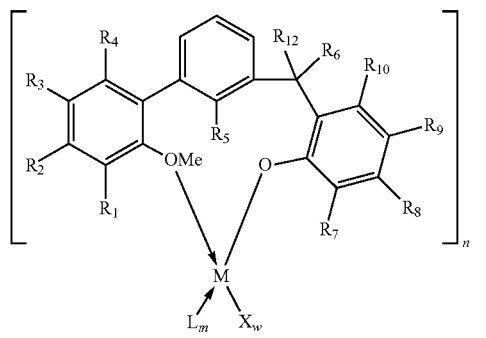

D

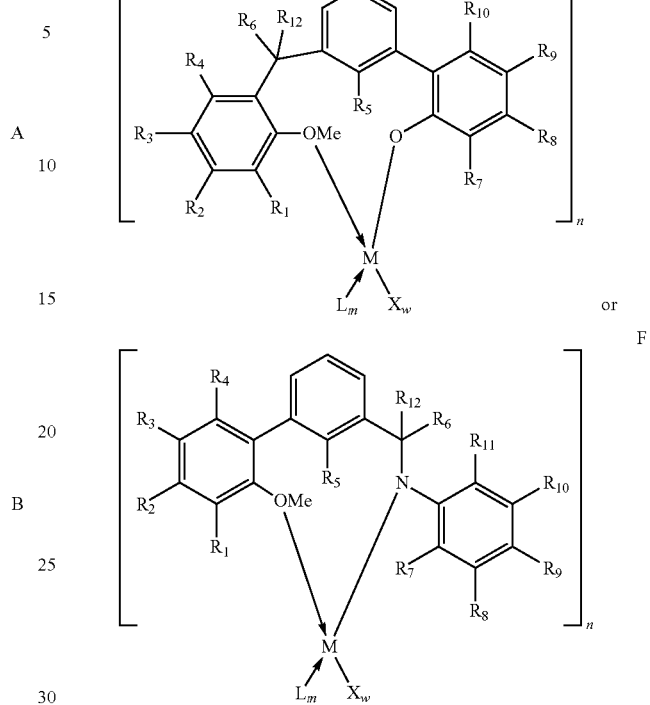

wherein each X is, independently, a hydride, a halogen, a hydrocarbyl, a substituted hydrocarbyl, a halocarbyl, or a substituted halocarbyl;

w is 0, 1, 2 or 3;

each $R^1$, $R^2$, $R^3$, $R^4$, $R^5$, $R^6$, $R^7$, $R^8$, $R^9$, $R^{10}$, $R^{12}$ and $R^{11}$ if present, is independently, a hydrogen, a hydrocarbyl, a substituted hydrocarbyl, a halocarbyl, a substituted halocarbyl, a halogen, an alkoxide, a sulfide, an amide, a phosphide, a silyl or another anionic heteroatom-containing group, or independently, may join together to form a $C_4$ to $C_{62}$ cyclic or polycyclic ring structure;

L is a neutral ligand bonded to M that may include molecules such as but not limited to pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, styrene, and the like;

M is Hf, Zr or Ti;

m is 0, 1 or 2 and indicates the absence or presence of L;

n is 1 or 2; and an activator.

17. The process according to paragraph 16, wherein the structure is C.

18. The process according to either of paragraphs 16 or 17, wherein n is 1 and w is 2 or 3.

19. The process according to any of paragraphs 16 through 18, wherein $R^6$ is phenyl or methyl and $R^7$ is phenyl or t-butyl.

20. The process according to paragraph 16, wherein the structure is:

A¹
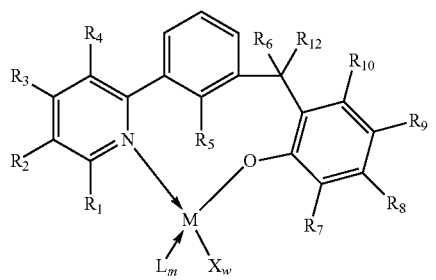
B¹
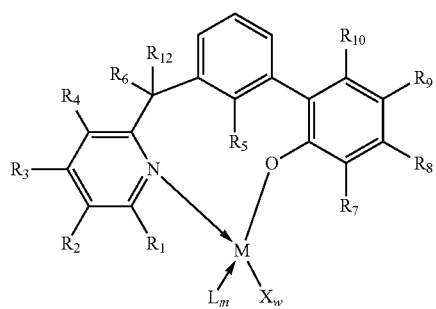
C¹
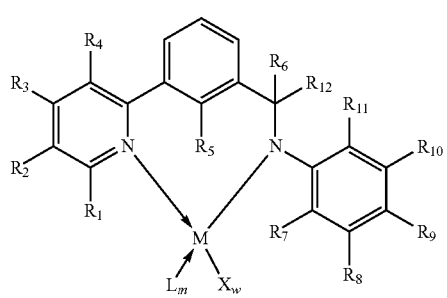
D¹
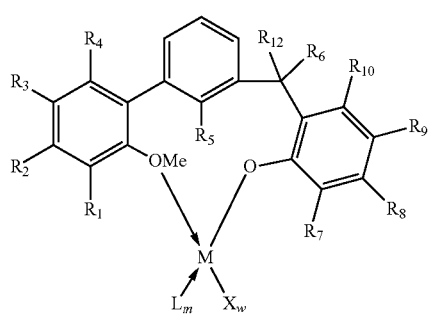
E¹
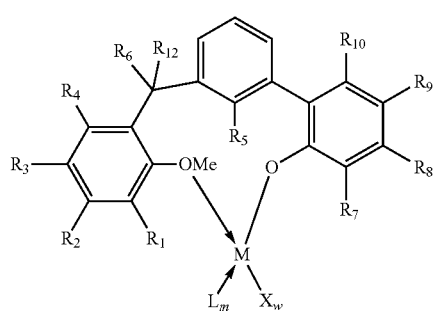
or
F¹
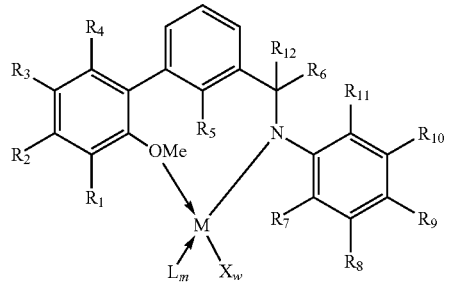
wherein n is 1 and w is 2 or 3.
21. A compound comprising a formula:
(I)
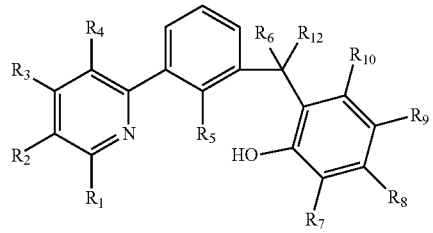
(II)
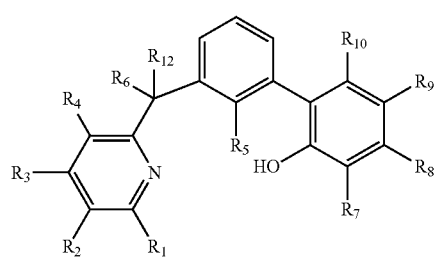
(III)
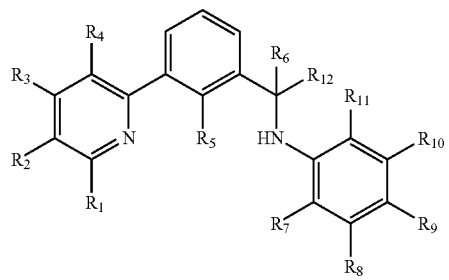
(IV)
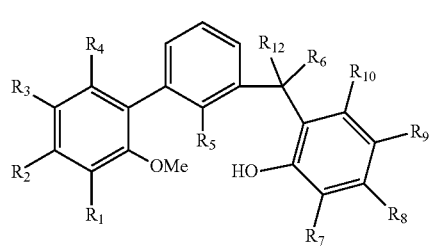

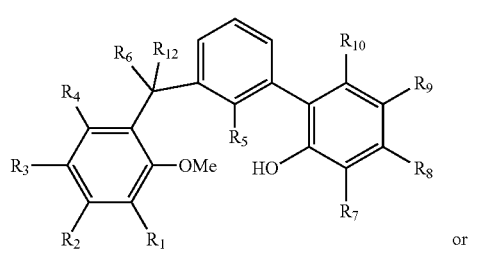

(V)

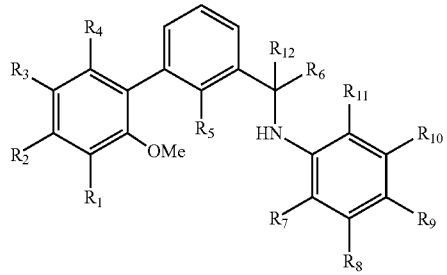

(VI)

wherein
each $R^1$, $R^2$, $R^3$, $R^4$, $R^5$, $R^6$, $R^7$, $R^8$, $R^9$, $R^{10}$, $R^{12}$ and $R^{11}$ if present, is, independently, a hydrogen, a hydrocarbyl, a substituted hydrocarbyl, a halocarbyl, a substituted halocarbyl, a halogen, an alkoxide, a sulfide, an amide, a phosphide, a silyl or another anionic heteroatom-containing group, or independently, may join together to form a $C_4$ to $C_{62}$ cyclic or polycyclic ring structure.

22. The compound according to paragraph 21, wherein $R^1$, $R^2$, $R^3$, $R^4$, $R^5$, $R^8$, $R^9$, $R^{10}$ and $R^{11}$ if present, are all hydrogen atoms and $R^6$ is phenyl, p-tolyl or methyl and $R^7$ is phenyl or t-butyl.

23. The compound according to paragraph 21, wherein $R^1$, $R^2$, $R^3$, $R^4$, $R^5$, $R^8$, $R^9$ and $R^{10}$ are all hydrogen atoms, $R^6$ is phenyl and $R^7$ is phenyl in formula (I) or $R^6$ is methyl and $R^7$ is t-butyl in formula (II) or $R^6$ is phenyl or methyl and $R^7$ is phenyl or t-butyl in formula (IV) or $R^6$ is methyl and $R^7$ is t-butyl or phenyl in formula (V).

24. The compound according to paragraph 21, wherein $R^1$, $R^2$, $R^3$, $R^4$, $R^5$, $R^8$, $R^9$ and $R^{10}$ are all hydrogen atoms, $R^6$ is methyl, p-tolyl, or phenyl, $R^7$ and $R^{11}$ are isopropyl groups in formula (III) and (VI).

25. The compound, composition or process according to any of paragraphs 1 through 24, wherein at least one of $R^6$ or $R^{12}$ is not a hydrogen atom.

26. The process according to any of paragraphs 16 through 20, wherein the polymer is homopolyethylene.

28. The compound, composition or process according to any of paragraphs 1 through 20, wherein when $R^5$ is a hydrogen atom, M may react with the $R^5$ hydrogen atom to generate HX and a bond is formed between the carbon bearing position at $R^5$ and M.

The following abbreviations are used through this specification: Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, nBu is normal butyl, TMS is trimethylsilyl, TIBA is trisobutylaluminum, MAO is methylalumoxane, pMe is para-methyl, Ar* is 2,6-diisopropylaryl, Bz is benzyl, THF is tetrahydrofuran, RT is room temperature and tol is toluene.

EXAMPLES

The foregoing discussion can be further described with reference to the following non-limiting examples. Illustrative catalyst compounds, each according to one or more embodiments described, were synthesized and used to polymerize ethylene monomer. All reactions were carried out under a purified nitrogen atmosphere using standard glovebox, high vacuum or Schlenk techniques, unless otherwise noted. All solvents used were anhydrous, de-oxygenated and purified according to known procedures. All starting materials were either purchased from Aldrich and purified prior to use or prepared according to procedures known to those skilled in the art.

Family A Synthetic Scheme

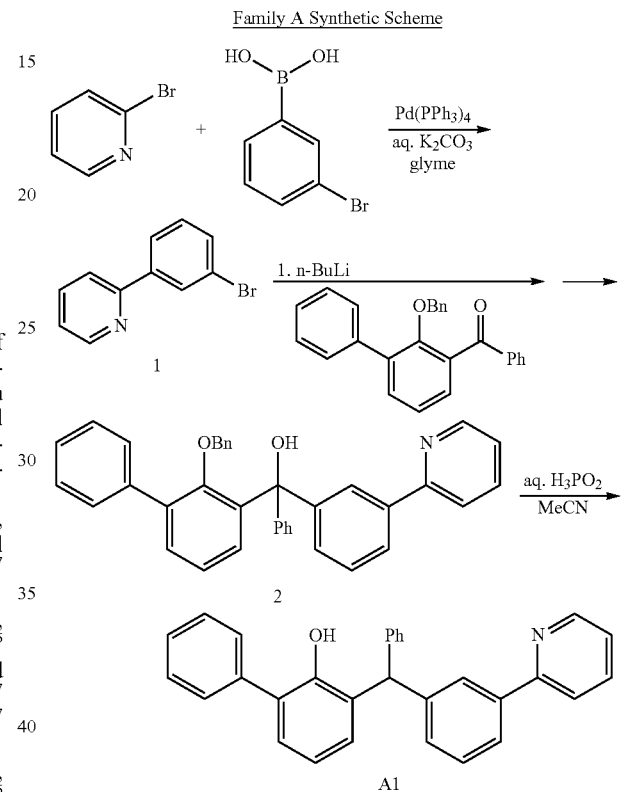

2-(3-Bromophenyl)pyridine (1): A mixture of 2-bromopyridine (4.8 g, 30.33 mmol), 3-bromophenyl boronic acid (4.06 g, 20.22 mmol), glyme (35 mL), tetrakis(triphenylphosphine)palladium(0) (0.4 g) and a solution of potassium carbonate (7.6 g, 55 mmol) in water (35 mL) was stirred well at reflux under nitrogen overnight. After cooling, the reaction mixture was diluted with ethyl acetate (600 mL) and washed with water (3×200 mL). The solvent and excess 2-bromopyridine were removed on a rotary evaporator (bath temperature=75° C.) and the crude product was purified by chromatography on silica (110 g) with 2% ethyl acetate in heptane (6 L) to produce 1 (3.55 g, 75%).

(2-(Benzyloxy)biphenyl-3-yl)(phenyl)(3-(pyridin-2-yl)phenyl)methanol (2): A solution of 1 (1.17 g, 5 mmol) in anhydrous tetrahydrofuran (15 mL) was stirred at −78° C. and 2.5M n-butyllithium in hexanes (2 mL, 5 mmol) was added at such a rate that temperature did not exceed −70° C. Stirring was continued on the cold bath for 30 min and a solution of 2-(benzyloxy)biphenyl-3-yl)(phenyl)methanone (1.82 g, 5 mmol) in tetrahydrofuran (10 mL) was added at such a rate that temperature did not exceed −65° C. Stirring was continued on the cold bath for 30 min and 2 hr at room temperature. The reaction mixture was poured on saturated ammonium chloride (150 mL) and extracted with ethyl acetate (200 mL). The organic extract was washed with water (2×100 mL) and dried over sodium sulfate. The solvent was removed on a rotary evaporator and the crude product was purified by chromatography on silica (80 g) with 3% ethyl acetate in heptane (1 L), 4% ethyl acetate in heptane (1 L) and 5% ethyl acetate in heptane (3 L) to yield 2 (1.82 g, 70%).

3-(Phenyl(3-(pyridin-2-yl)phenyl)methyl)biphenyl-2-ol (A1): A solution of 2(0.95 g, 1.83 mmol) in acetonitrile (24 mL) and 50% aqueous hypophosphorous acid (22 mL) was kept at reflux for 64 hr. The acetonitrile was removed in vacuo, the residue was diluted with ethyl acetate (200 mL) and water (100 mL). Phases were separated. The organic phase was washed with saturated sodium bicarbonate (2×80 mL) and water (2×80 mL) dried over sodium sulfate and filtered. The solvent was removed on a rotary evaporator. The crude product was purified by chromatography on silica (80 g) with 10% ethyl acetate in hexane (3 L) to yield slightly impure A1 (0.28 g, total yield: 52%).

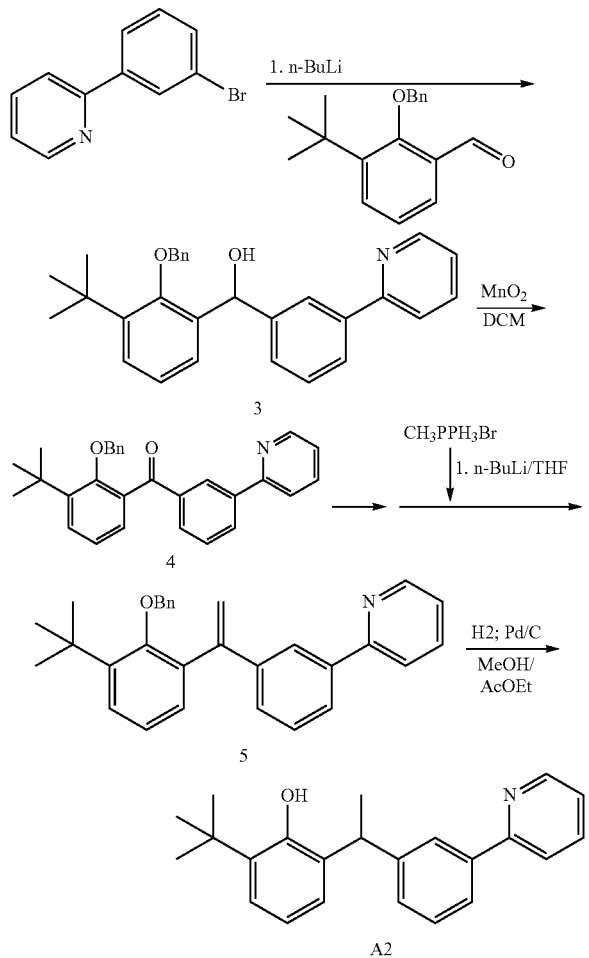

(2-(Benzyloxy)-3-tert-butylphenyl)(3-(pyridin-2-yl)phenyl)methanol (3): A solution of 2-(3-bromophenyl)pyridine (2.4 g, 10.25 mmol) in anhydrous tetrahydrofuran (25 mL) was stirred at −78° C. and 2.5M n-butyllithium in hexanes (4.1 mL, 10.25 mmol) was added at such a rate that temperature did not exceed −70° C. Stirring was continued on the cold bath for 30 min and a solution of 2-(benzyloxy)-3-tert-butylbenzaldehyde (2.75 g, 10.25 mmol) in tetrahydrofuran (12 mL) was added at such a rate that temperature did not exceed −65° C. Stirring was continued on the cold bath for 20 min and 2 hr at room temperature. The reaction mixture was poured on saturated ammonium chloride (250 mL) and extracted with ethyl acetate (350 mL). The organic extract was washed with water (2×100 mL) and dried over sodium sulfate. The solvent was removed on a rotary evaporator and the crude product was used as such in the next step.

(2-(Benzyloxy)-3-tert-butylphenyl)(3-(pyridin-2-yl)phenyl)methanone (4): A solution of crude 3 (10.25 mmol) in dichloromethane (160 mL) was treated with manganese dioxide (14 g, 15 equiv.) and this suspension was stirred under reflux for 6 hr. The reaction mixture was filtered through Celite and the filter cake was washed with ethyl acetate. The solvent was removed on a rotary evaporator and the crude product was purified by chromatography on silica (110 g) with 5% ethyl acetate in heptane (5 L) to produce 4 (2.75 g, 64% over 2 steps).

2-(3-(1-(2-(Benzyloxy)-3-tert-butylphenyl)vinyl)phenyl)pyridine (5): Methyl triphenylphosphonium bromide (2.2 g, 6.17 mmol) was suspended in anhydrous tetrahydrofuran (20 mL) and stirred under nitrogen on an ice bath. 2.5M n-Butyllithium in hexanes (2.3 mL, 5.75 mmol) was added at such a rate that temperature did not exceed 3° C. Stirring was continued at room temperature for 1 hr. The reaction mixture was cooled on an ice bath and a solution of 4 (1.3 g, 3.08 mmol) in tetrahydrofuran (8 mL) was added at such a rate that temperature did not exceed 3° C. Stirring was continued at room temperature overnight. The reaction mixture was poured on saturated ammonium chloride (150 mL) and extracted with ethyl acetate (150 mL). The organic extract was washed with water (2×80 mL) and dried over sodium sulfate. The solvent was removed on a rotary evaporator and the crude product was purified by chromatography on silica (80 g) with 2% ethyl acetate in heptane (2 L), then 4% (4 L) to produce 5 (1.18 g, 91%).

2-tert-Butyl-6-(1-(3-(pyridin-2-yl)phenyl)ethyl)phenol (A2): A solution of 5 (1.12 g, 2.67 mmol) in methanol (40 mL) and ethyl acetate (80 mL) was treated with 20% palladium on activated carbon (0.2 g, 0% wet) and hydrogenated in a Parr shaker at 10 psi for 3.5 hr. The catalyst was filtered off and washed with ethyl acetate. The solvent was removed on a rotary evaporator and the crude product was purified by chromatography on silica (80 g) with 2% ethyl acetate in hexane (1 L), then 4% (2 L) to yield pure A2 (0.75 g, 85%).

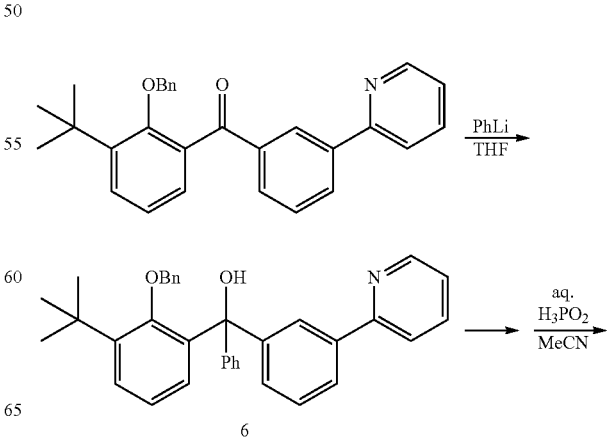

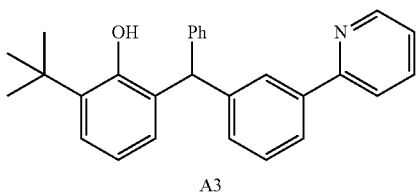

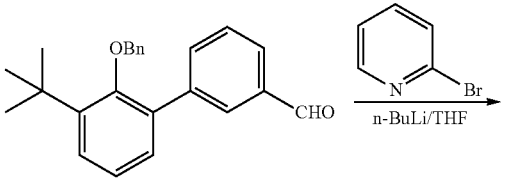

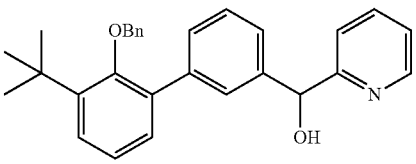

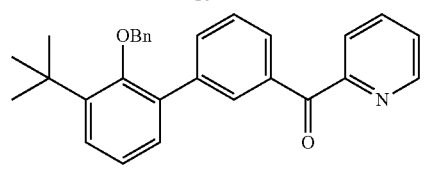

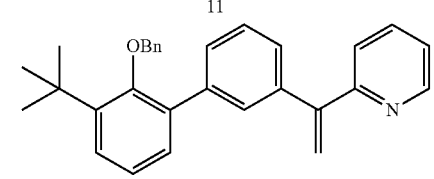

(2-(Benzyloxy)-3-tert-butylphenyl)(phenyl)(3-(pyridin-2-yl)phenyl)methanol (6): A solution of (2-(benzyloxy)-3-tert-butylphenyl)(3-(pyridin-2-yl)phenyl)methanone (0.96 g, 2.28 mmol) in anhydrous tetrahydrofuran (20 mL) was stirred at −78° C. under nitrogen and 1.8 M phenyllithium (2 mL, 3.6 mmol) was added at such a rate that the temperature did not exceed −70° C. Stirring was continued at −78° C. for 30 min for 1 hr at room temperature. The reaction mixture was poured on saturated ammonium chloride (150 mL) and extracted with ethyl acetate (150 mL). The organic extract was washed with water (2×100 mL), dried over sodium sulfate and stripped. The crude product was purified by chromatography on silica (60 g) with 5% ethyl acetate in heptane (1 L), then 7.5% (2 L) to afford 6 (1.14 g, 100%). This material contains a minor impurity and it was used as such in the next step.

2-tert-Butyl-6-(phenyl(3-(pyridin-2-yl)phenyl)methyl)phenol (A3): A solution of 6 (1.12 g, 2.24 mmol) in acetonitrile (15 mL) and 50% aqueous hypophosphorous acid (10 mL) was kept at reflux for 3 hr. The acetonitrile was removed in vacuo, the residue was diluted with water (80 mL) and extracted with ethyl acetate (150 mL). The organic phase was washed with water (100 mL), saturated sodium bicarbonate (100 mL) and water (2×100 mL), dried over sodium sulfate and filtered. The solvent was removed on a rotary evaporator. The crude product was purified by chromatography on silica (50 g) with 2% ethyl acetate in heptane (2 L) and 4% (3 L) to yield pure A3 (0.17 g).

Family B Synthetic Scheme

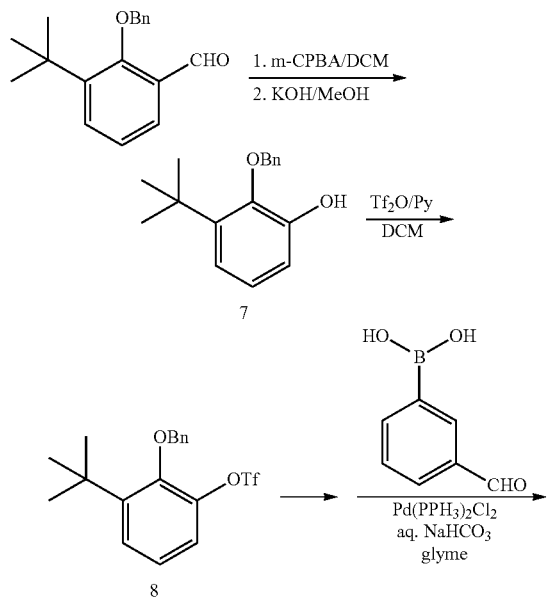

2-(Benzyloxy)-3-tert-butylphenol (7): A solution of 2-(benzyloxy)-3-tert-butylbenzaldehyde (20 g, 74.53 mmol) in dichloromethane (400 mL) was treated with m-chloroperbenzoic acid (70%, 20 g) in 3 portions at room temperature. Stirring was continued overnight. The reaction mixture was diluted with dichloromethane (to 1 L) and washed with saturated sodium bicarbonate (2×400 mL) and water (500 mL). The organic layer was dried over sodium sulfate and filtered. The solvent was removed in a rotary evaporator. The residue was taken in methanol (375 mL), potassium hydroxide (7.5 g) was added and this mixture was stirred at room temperature overnight. The solvent was removed in a rotary evaporator. The residue was taken in water (250 mL) and made acidic with 6N hydrochloric acid. The aqueous phase was extracted with ethyl acetate (800 mL). The organic extract was washed with water (300 mL), dried over sodium sulfate and the solvent was removed in a rotary evaporator. The crude product was purified by chromatography on silica (350 g) with 5% ethyl acetate in heptane (4 L) to afford pure 7 (16 g, 84%).

2-(Benzyloxy)-3-tert-butylphenyl trifluoromethanesulfonate (8): A solution of 7 (16 g, 62.42 mmol) in dichloromethane (300 mL) was stirred on an ice bath. Pyridine (8 mL, 1.4 equiv.) was added and a solution of triflic anhydride (21 g, 1.2 equiv.) in dichloromethane (20 mL) was added at such a rate that the temperature did not exceed 5° C. Stirring was continued on the cold bath for 20 min. Water (10 mL) was added and stirring was continued for 30 min. The reaction mixture was diluted with dichloromethane (to 600 mL) and washed with water (300 mL), 1N hydrochloric acid (300 mL) and water (2×300 mL). The organic layer was dried over sodium sulfate and filtered. The solvent was removed in a rotary evaporator. The crude product was purified by chromatography on silica (350 g) with heptane (7 L) to afford pure 8 (21.29 g, 88%).

2'-(Benzyloxy)-3'-tert-butylbiphenyl-3-carbaldehyde (9): A solution of 8 (3.75 g, 9.65 mmol), 3-formylphenylboronic acid (2.89 g, 19.3 mmol, 2 equiv.), bis(triphenylphosphine) palladium(II) dichloride (0.20 g), glyme (10 mL) and a solution of sodium bicarbonate (2.9 g, 34.5 mmol) in water (50 mL) was stirred well at reflux under nitrogen for 4 hr. After cooling the reaction mixture was diluted with ethyl acetate (150 mL) and washed with water (2×100 mL). The organic layer was dried over sodium sulfate and filtered. The solvent was removed in a rotary evaporator. The crude product was purified by chromatography on silica (120 g) with heptane (3 L) to afford pure 9 (3.19 g, 99%).

(2'-(Benzyloxy)-3'-tert-butylbiphenyl-3-yl)(pyridin-2-yl) methanol (10): A solution of 2-bromopyridine (1.51 g, 9.58 mmol) in dry tetrahydrofuran (20 mL) was stirred under nitrogen at −78° C. and 2.5M n-butyllithium in hexanes (3.8 mL, 9.5 mmol) was added at such a rate that the temperature did not exceed −70° C. Stirring was continued at −78° C. for 30 min. when a solution of 9 (2.1 g, 6.1 mmol) in tetrahydrofuran (15 mL) was added at such a rate that the temperature did not exceed −65° C. Stirring was continued at −78° C. for 20 min., then for 2 hr at room temperature. The reaction mixture was poured on saturated ammonium chloride (150 mL) and extracted with ethyl acetate (200 mL). The organic extract was washed with water (2×100 mL), dried over sodium sulfate and stripped. The crude 10 was used as such in the next step.

(2'-(Benzyloxy)-3'-tert-butylbiphenyl-3-yl)(pyridin-2-yl) methanone (11): A solution of crude 10 (6.1 mmol) in dichloromethane (80 mL) was treated with manganese dioxide (85%, 8 g, 15 equiv.) and this suspension was stirred at reflux for 3 hr. The solids were filtered out and washed with ethyl acetate. The solvent was removed in a rotary evaporator and the residue was purified by chromatography on silica (80 g) with 5% ethyl acetate in heptane (1 L) and 7.5% ethyl acetate in heptane (3 L) to afford pure 11 (1.64 g, 60% over 2 steps).

2-(1-(2'-(Benzyloxy)-3'-tert-butylbiphenyl-3-yl)vinyl)pyridine (12): A solution of methyltriphenylphosphonium-bromide (1.4 g, 3.9 mmol) in anhydrous tetrahydrofuran (15 mL) was stirred under nitrogen on an ice bath and 2.5 M n-butyllithium in hexanes (1.5 mL, 3.75 mmol) was slowly added. After 20 min. the cold bath was removed and stirring was continued at room temperature for 1 hr. The reaction mixture was cooled on an ice bath and a solution of 11 (0.82 g, 1.95 mmol) in tetrahydrofuran (15 mL) was added at such a rate that the temperature did not exceed 5° C. Stirring was continued overnight at room temperature. The reaction mixture was poured on saturated ammonium chloride (120 mL) and extracted with ethyl acetate (150 mL). The organic extract was washed with water (2×80 mL), dried over sodium sulfate and stripped. The residue was purified by chromatography on silica (50 g) with 5% ethyl acetate in heptane (3 L) to produce pure 12 (0.13 g, 16%).

3-tert-Butyl-3'-(1-(pyridin-2-yl)ethyl)biphenyl-2-ol (B1): A solution of 12 (0.13 g, 0.31 mmol) in methanol (10 mL) and ethyl acetate (30 mL) was treated with 20% palladium on activated carbon (50% wet, 0.05 g) and was hydrogenated at 10 psi in a Parr shaker for 2 hr. The catalyst was filtered out and washed with ethyl acetate. The solvent was removed in a rotary evaporator and the crude product was purified by chromatography on silica (25 g) with 5% ethyl acetate in hexane (3 L). Pure B1 (0.08 g, 80%) was isolated.

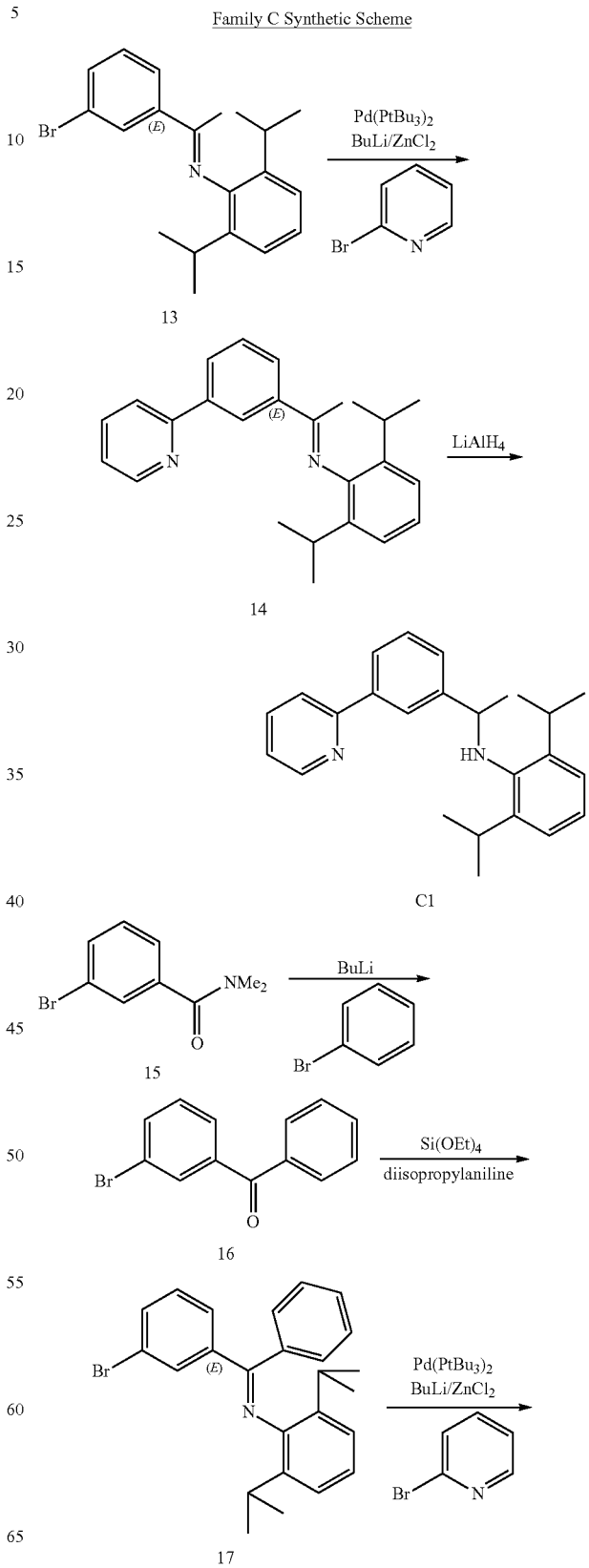

Family C Synthetic Scheme

-continued

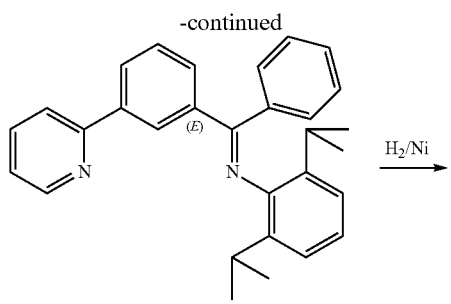

18

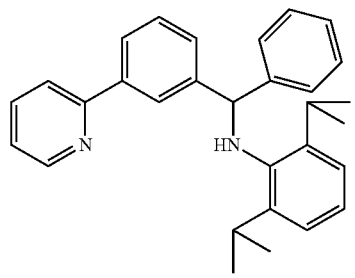

C2

(2,6-Diisopropylphenyl)[(1Z)-1-(3-pyridin-2-ylphenyl) ethylidene]amine (14): To a solution of 11.1 g (31.0 mmol) of (13) in 110 mL of THF, 12.4 mL (31.0 mmol) of 2.5 M $^n$BuLi in hexanes was added at −100° C. This mixture was stirred for 1 hr at −70° C., cooled to −100° C., and 33.4 mL (33.4 mmol) of 1.0 M ZnCl$_2$ in THF was added. The resulting mixture was slowly warmed to room temperature, stirred for 12 hr at this temperature, and then 4.94 g (31.0 mmol) of 2-bromopyridine and 340 mg (0.62 mmol) of Pd(P$^t$Bu$_3$)$_2$ were added. This mixture was refluxed for 3 hr, 20 mL of water was added, and the resulting mixture was passed through a short layer of silica gel 60 (40-63 um). The silica gel layer was additionally washed with 150 mL of dichloromethane. The combined organic elute was evaporated to dryness, and the product was isolated from the residue by flash chromatography on silica gel 60 (40-63 um, eluent: from hexanes to hexanes-diethyl ether=1:1, vol.). This procedure gave 9.28 g (84%) of the title product.

(2,6-Diisopropylphenyl)[1-(3-pyridin-2-ylphenyl)ethyl] amine (C1): To a suspension of 2.70 g (71.0 mmol) of LiAlH$_4$ in 250 mL of THF, 8.03 g (22.6 mmol) of 14 was added. This mixture was refluxed for 3 hr, and then saturated aqueous Na$_2$SO$_4$ was added. The organic layer was separated, and the aqueous layer was additionally washed with 2×100 ml, of diethyl ether. The combined organic extract was evaporated to dryness, and the product was isolated using flash chromatography on silica gel 60 (40-63 um, eluent: hexanes-diethyl ether from 100:1 to 10:1, vol.) to yield 7.37 g (91%) of C1.

(3-Bromophenyl)(phenyl)methanone (16): To a solution of 8.25 g (52.5 mmol) of bromobenzene in 100 mL of THF, 70 mL (105 mmol) of 2.5 M $^t$BuLi in pentane was added dropwise with vigorous stirring for 2 h at −80° C. This mixture was slowly warmed to room temperature and then stirred for 30 min at this temperature. 11.4 g (50 mmol) of 3-bromo-N,N-dimethylbenzamide was added at 0° C., and the resulting mixture was stirred for 12 hr at room temperature. 150 mL of water was added, the organic solvent was evaporated using a rotary evaporator, and the product was extracted with 2×100 mL of dichloromethane. The combined extracts were dried over K$_2$CO$_3$ and then evaporated to dryness. This procedure gave 12.2 g (89%) of 16 which was further used without an additional purification.

N-[(3-Bromophenyl)(phenyl)methylene]-2,6-diisopropylaniline (17): In 25 mL Claisens flask in an argon atmosphere, a mixture of 5.22 g (20.0 mmol) of 16, 5.00 g (24.0 mmol) of Si(OEt)$_4$, and 3.90 g (22.0 mmol) of 2,6-diisopropylaniline was heated to 170° C., and then 0.13 mL of 96% H$_2$SO$_4$ was added. This mixture was stirred at this temperature for 50 hr, and the formed ethanol was slowly distilled off. Later, 300 mL of cold water was added, and the product was extracted with 2×70 mL of diethyl ether. The combined extract was dried over K$_2$CO$_3$ and then evaporated to dryness. The product was isolated by flash-chromatography on silica gel 60 (40-63 um, eluent: from hexanes to hexanes-diethyl ether, 100:1, vol.). This procedure gave 7.06 g (84%) of the title product 17.

(2,6-Diisopropylphenyl)[phenyl(3-pyridin-2-ylphenyl) methylene]amine (18): To a solution of 1.26 g (3.00 mmol) of 17 in 10 mL of THF, 1.20 mL (3.00 mmol) of 2.5 M $^n$BuLi in hexanes was added at −100° C. This reaction mixture was stirred for 1 hr at −70° C., then cooled to −100° C., and 3.20 mL (3.20 mmol) of 1.0 M ZnCl$_2$ in THF was added. The resulting mixture was slowly warmed to room temperature, stirred for 12 hr at this temperature, and then 0.474 g (3.00 mmol) of 2-bromopyridine and 30 mg (0.06 mmol) of Pd(P$^t$Bu$_3$)$_2$ were added. The resulting mixture was refluxed for 3 hr, and 2 mL of water was added. This mixture was passed through short layer of silica gel 60 (40-63 um), and the silica gel layer was additionally washed with 30 mL of dichloromethane. The combined organic elute was evaporated to dryness, and the product was isolated from the residue by flash chromatography on silica gel 60 (40-63 um, eluent: from hexanes to hexanes-diethyl ether=10:1, vol.) to generate 1.10 g (88%) of the product.

(2,6-Diisopropylphenyl)[phenyl(3-pyridin-2-ylphenyl) methyl]amine (C2): A mixture of 4.15 g (9.90 mmol) of 18 in 150 mL of THF and fresh Ni-Raney obtained from 2.00 g of 50% alloy of Ni with Al was hydrogenated in a stainless steel autoclave at 70 atm of hydrogen for 4 hr at 65° C. The reaction mixture was filtered through glass frit, and the filtrate was evaporated to dryness. The product was isolated by flash chromatography on silica gel 60 (40-63 um, eluent: hexanes-ethyl acetate from 40:1 to 10:1, vol.) to give 3.75 g (90%) of C2.

Synthesis of (C1)HfMe$_2$, (C1)HfBz$_2$, (C1)HfCl$_2$, (C1)ZrMe$_2$, (C2)ZrMe$_2$ and (C2)HfMe$_2$

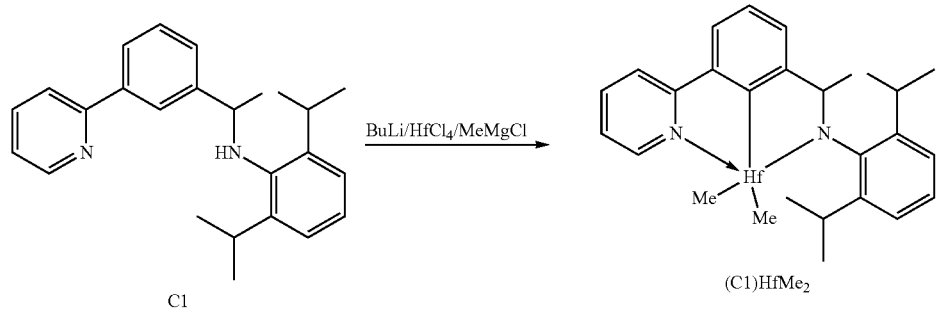

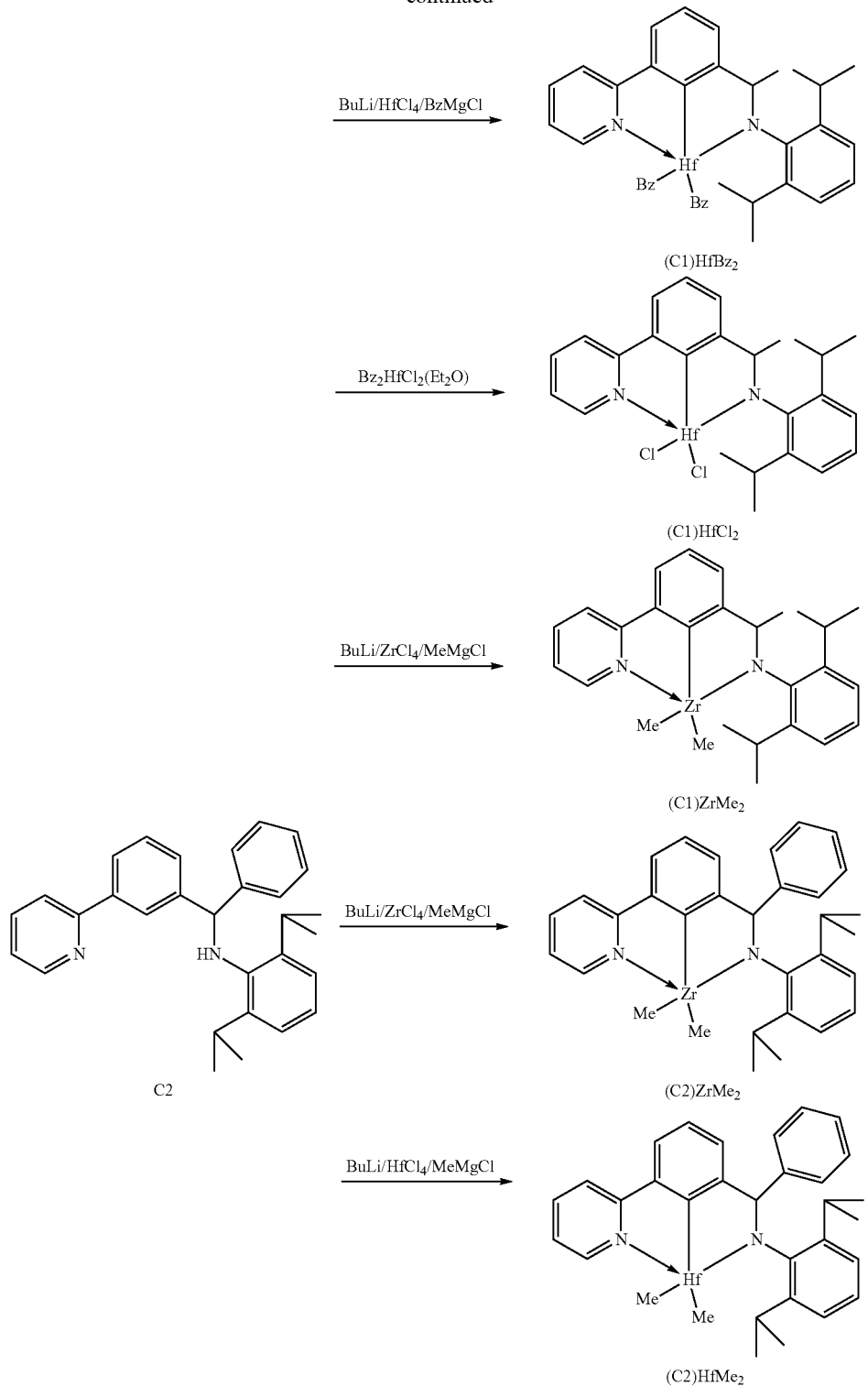

[(2,6-Diisopropylphenyl)[1-(3-pyridin-2-ylphenyl)ethyl]amido]hafnium(IV)-dimethyl ((C1)HfMe₂): To a solution of 1.08 g (3.00 mmol) of C1 in 20 mL of toluene, 1.20 mL (3.00 mmol) of 2.5 M ⁿBuLi in hexanes was added at room temperature. This mixture was stirred for 1 hr at this temperature, and then 0.96 g (3.00 mmol) of HfCl₄ was added. The resulting mixture was stirred for 1 hr at 120° C., cooled to room temperature, and then 3.70 mL (10.5 mmol) of 2.86 M MeMgCl in diethyl ether was added. This reaction mixture was stirred for 12 hr at room temperature and then evaporated to dryness. To the residue (preliminary dried in vacuum) 20 mL of toluene was added. The obtained suspension was filtered through glass frit. The filtrate was evaporated to dryness, and the residue was dried in vacuum. Yield 0.53 g (31%) of the title product as yellowish solid.

[(2,6-Diisopropylphenyl)[1-(3-pyridin-2-ylphenyl)ethyl] amido]hafnium(IV)-dibenzyl ((C1)HfBz$_2$): To a solution of 1.39 g (3.88 mmol) of C1 in 26 mL of toluene, 1.55 mL (3.88 mmol) of 2.5 M "BuLi in hexanes was added at room temperature. This mixture was stirred for 1 hr at this temperature, and then 1.24 g (3.88 mmol) of HfCl$_4$ was added. The resulting mixture was stirred for 1 hr at 120° C., cooled to room temperature, and then 14.8 mL (13.6 mmol) of 0.92 M BnMgCl in diethyl ether was added. This reaction mixture was stirred for 72 hr at room temperature and then evaporated to dryness. To the residue (preliminary dried in vacuum) 50 mL of toluene was added. The obtained suspension was filtered through glass frit. The precipitate was additionally washed with 100 mL of toluene. The filtrate was evaporated to dryness, and the residue was dried in vacuum. The product was extracted with 3×80 mL of hexanes. The obtained suspension was filtered through glass frit, the filtrate was evaporated to dryness, and the residue was dried in vacuum to yield 1.37 g of a ca. 3 to 1 mixture of bibenzyl and the title product. Thus yield of (C1)HfBz$_2$ was 28%.

[(2,6-Diisopropylphenyl)[1-(3-pyridin-2-ylphenyl)ethyl] amido]hafnium(IV)-dichloride ((C1)HfCl$_2$): To a solution of 1.17 g (3.25 mmol) of (2,6-diisopropylphenyl)[1-(3-pyridin-2-ylphenyl)ethyl]amine in 20 mL of toluene, 1.64 g (3.25 mmol) of Bn$_2$HfCl$_2$(Et$_2$O) was added at −30° C. This mixture was slowly warmed to room temperature, stirred for 16 hr at this temperature and then evaporated to dryness. The residue was dried in vacuum to give 0.93 g (47%) of the title material.

[(2,6-Diisopropylphenyl)[1-(3-pyridin-2-ylphenyl)ethyl] amido]zirconium(IV)-dimethyl ((C1)ZrMe$_2$): To a solution of 1.80 g (5.00 mmol) of C1 in 35 mL of toluene, 2.00 mL (5.00 mmol) of 2.5 M "BuLi in hexanes was added at room temperature. This mixture was stirred for 1 hr at this temperature, and then 1.17 g (5.00 mmol) of ZrCl$_4$ was added. The resulting mixture was stirred for 2 hr at 100° C., cooled to room temperature, and then 6.13 mL (17.5 mmol) of 2.86 M MeMgCl in diethyl ether was added. This reaction mixture was stirred for 12 hr at room temperature and then evaporated to dryness. To the residue (preliminary dried in vacuum) 20 mL of toluene was added. The obtained suspension was filtered through glass frit. The filtrate was evaporated to dryness, and the residue was dried in vacuum. Yield 0.17 g (7%) of the title product as yellowish solid.

[(2,6-Diisopropylphenyl)[1-(3-pyridin-2-ylphenyl)methylphenyl]amido]-zirconium(IV)dimethyl ((C2)ZrMe$_2$): To a solution of 2.10 g (5.00 mmol) of C2 in 35 mL of toluene, 2.00 mL (5.00 mmol) of 2.5 M "BuLi in hexanes was added at room temperature. This mixture was stirred for 1 hr at this temperature, and then 1.17 g (5.00 mmol) of ZrCl$_4$ was added. The resulting mixture was stirred for 2 hr at 100° C., cooled to room temperature, and then 6.13 ml, (17.5 mmol) of 2.86 M MeMgCl in ether was added. This reaction mixture was stirred for 12 hr at room temperature and then evaporated to dryness. To the residue (preliminary dried in vacuum) 20 mL of toluene was added. The obtained suspension was filtered through glass frit. The filtrate was evaporated to dryness, and the residue was dried in vacuum. Yield 0.49 g (18%) of the title product as yellowish solid.

[(2,6-Diisopropylphenyl)[1-(3-pyridin-2-ylphenyl)methylphenyl]amido]hafnium-(IV)dimethyl ((C2)HfMe$_2$): To a solution of 2.10 g (5.00 mmol) of C2 in 35 mL of toluene, 2.00 mL (5.00 mmol) of 2.5 M "BuLi in hexanes was added at room temperature. This mixture was stirred for 1 hr at this temperature, and then 1.60 g (5.00 mmol) of HfCl$_4$ was added. The resulting mixture was stirred for 2 hr at 100° C., cooled to room temperature, and then 7.45 mL (17.5 mmol) of 2.35 M MeMgCl in diethyl ether was added. This reaction mixture was stirred for 12 hr at room temperature and then evaporated to dryness. To the residue (preliminary dried in vacuum) 20 mL of toluene was added. The obtained suspension was filtered through glass frit. The filtrate was evaporated to dryness, and the residue was dried in vacuum to generate 1.32 g (42%) of (C2)HfMe$_2$.

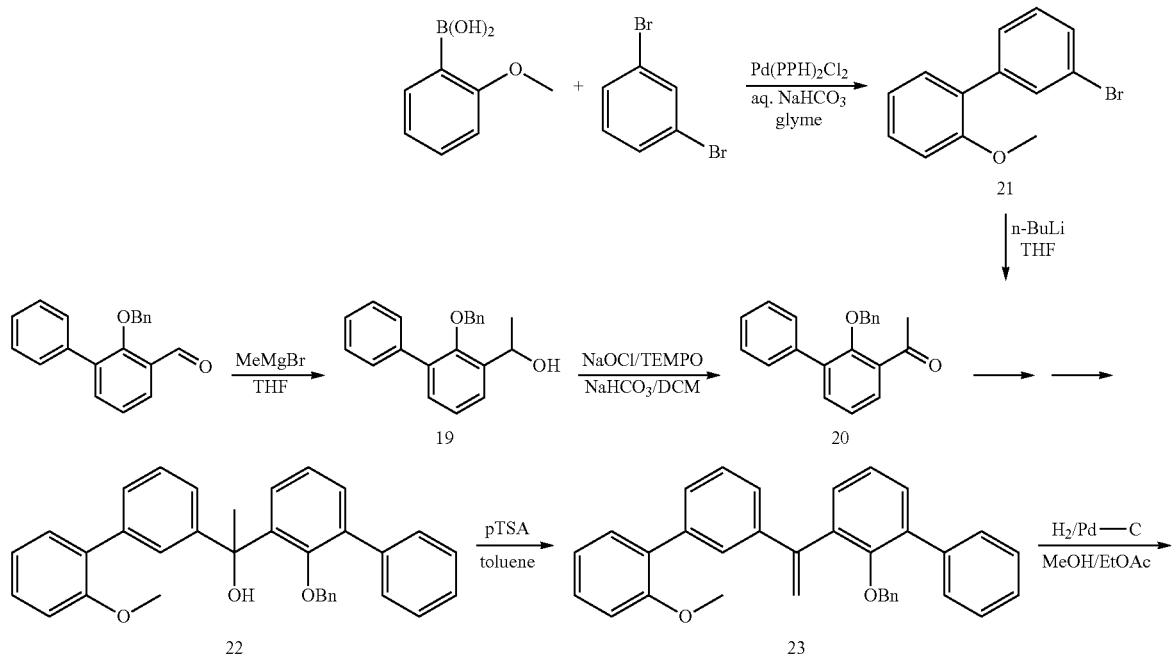

Family D Synthetic Scheme

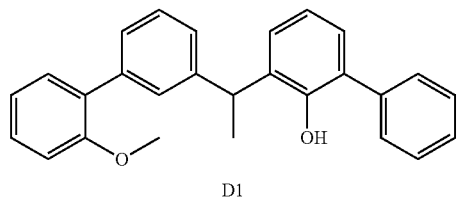

D1

1-(2-(Benzyloxy)biphenyl-3-yl)ethanol (19): A solution of 2-(benzyloxy)biphenyl-3-carbaldehyde (5.55 g, 20 mmol) in anhydrous tetrahydrofuran (100 mL) was stirred under nitrogen on an water bath at room temperature and 3M methyl magnesium bromide in tetrahydrofuran (10 mL, 30 mmol, 1.5 equiv.) was added. Stirring was continued at room temperature for 40 min. The reaction mixture was poured onto saturated ammonium chloride (200 mL) and extracted with ethyl acetate (2×200 mL). The organic extract was washed with water (100 mL), dried over sodium sulfate and stripped to afford pure 1 (6 g, 98%).

1-(2-(Benzyloxy)biphenyl-3-yl)ethanone (20): To a solution of 1 (6 g, 19.7 mmol) in dichloromethane (30 mL) a solution of potassium bromide (0.7 g) in water (4 mL) was added. This mixture was stirred on an ice bath. TEMPO (45 mg) was added and a solution of 37% sodium hypochlorite (19 mL), sodium bicarbonate (2 g) and water (to 40 mL) was added in portions at such a rate as to maintain the temperature below 5° C. When the dark color of oxidized TEMPO persisted the addition was stopped. Phases were separated. The aqueous phase was extracted with dichloromethane (25 mL). The combined organic extracts were washed with water (80 mL), 1N hydrochloric acid (80 mL) and water (80 mL), dried over sodium sulfate and stripped. Almost pure 20 (5.95 g, 100%) was obtained.

3'-Bromo-2-methoxybiphenyl (21): A mixture of 2-methoxyphenylboronic acid (4.3 g, 28.3 mmol), 3,5-dibromobenzene (20 g, 85.5 mmol, 3 equiv.) and bis(triphenylphosphine)palladium(II) dichloride (100 mg) in ethyleneglycol dimethylether (25 mL) and a solution of sodium bicarbonate (8.2 g, 0.098 mol) in water (140 mL) were kept at reflux under nitrogen with good stirring overnight. After cooling, the reaction mixture was partitioned between ethyl acetate (600 mL) and water (300 mL). The organic phase was washed with water (2×300 mL), dried over sodium sulfate and filtered. The solvent was removed in vacuo and the crude product was purified by chromatography on silica (150 g) with heptane (6 L) to afford pure 21 (14.2 g, 58%).

1-(2-(Benzyloxy)biphenyl-3-yl)-1-(2'-methoxybiphenyl-3-yl)ethanol (22): A solution of 21 (0.7 g, 2.66 mmol) in anhydrous tetrahydrofuran (15 mL) was stirred under nitrogen at −78° C. and 2.5M n-butyllithium in hexanes (1.1 mL, 2.75 mmol) was added at such a rate that the temperature did not exceed −70° C. Stirring was continued at −78° C. for 1 hr when a solution of 20 (0.8 g, 2.66 mmol) in tetrahydrofuran (5 mL) was added at such a rate that the temperature did not exceed −65° C. Stirring was continued at −78° C. for 30 min., then for 2 hrs at room temperature. The reaction mixture was poured onto saturated ammonium chloride (120 mL) and extracted with ethyl acetate (150 mL). The organic extract was washed with water (2×80 mL), dried over sodium sulfate and stripped. The crude 22 was used as such in the next step.

3'-(1-(2-(Benzyloxy)biphenyl-3-yl)vinyl)-2-methoxybiphenyl (23): A solution of crude 22 (2.66 mmol) in toluene (60 mL) was treated with para-toluenesulfonic acid (20 mg) and refluxed under a Dean-Stark trap for 1.5 hrs. After cooling, the reaction mixture was diluted with ethyl acetate (100 mL) and washed with saturated sodium bicarbonate (100 mL) and water (100 mL). The solvent was removed in a rotary evaporator and the crude product was purified by chromatography on silica (40 g) with hexane (2 L) and 1% ethyl acetate in hexane (2 L) to afford pure 23 (0.12 g) and impure 23 (0.50 g).

3-(1-(2'-Methoxybiphenyl-3-yl)ethyl)biphenyl-2-ol (D1): A solution of impure 23 (0.5 g, 1.06 mmol) in methanol (20 mL) and ethyl acetate (40 mL) was treated with 20% palladium on activated carbon (50% wet, 0.05 g) and was hydrogenated at 40 psi in a Parr shaker for 3 hr. The catalyst was filtered out and washed with ethyl acetate. The filtrate was stripped and the crude product was purified by chromatography on silica (45 g) with 2% ethyl acetate in hexane (3 L) to afford pure D1 (0.33 g, 82%).

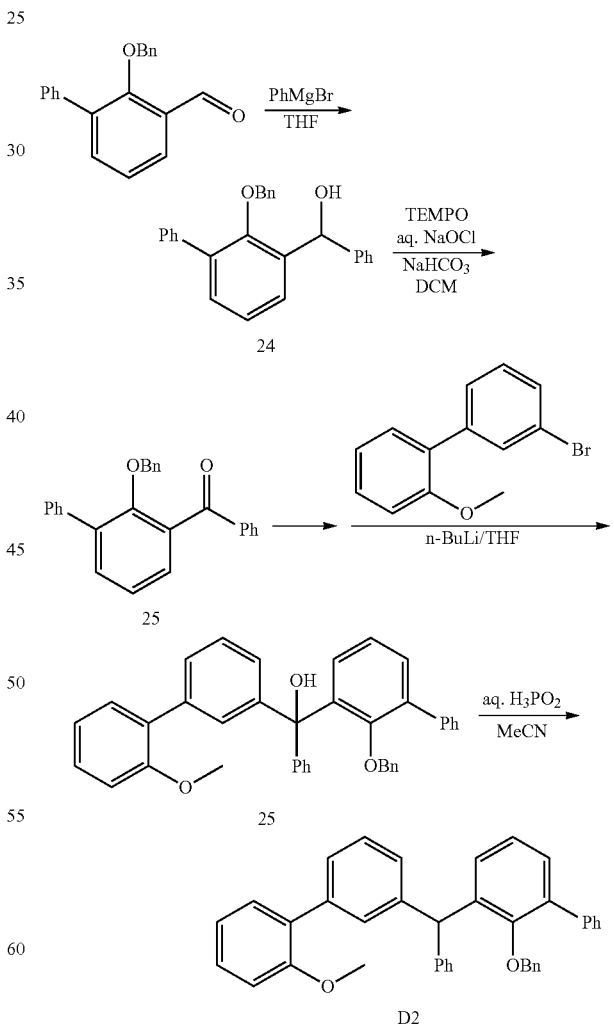

(2-(Benzyloxy)biphenyl-3-yl)(phenyl)methanol (24): A solution of 2-(benzyloxy)biphenyl-3-carbaldehyde (14.4 g, 50 mmol) in anhydrous tetrahydrofuran (180 mL) was stirred on an ice bath under nitrogen and 1M phenylmagnesium bromide in tetrahydrofuran (60 mL, 60 mmol, 1.2 equiv.) was added over 20 min. Stirring was continued for 3 hr at room temperature. The reaction mixture was poured on saturated ammonium chloride (600 mL) and extracted with ethyl acetate (800 mL). The organic extract was washed with water (2×400 mL). The organic layer was dried over sodium sulfate, filtered and the solvent was removed on a rotary evaporator. Crude 24 (19.2 g, 105%) was used in the next step without purification.

(2-(Benzyloxy)biphenyl-3-yl)(phenyl)methanone (25): A solution of crude 24 (50 mmol) in dichloromethane (200 mL) and a solution of potassium bromide (0.7 g) in water (10 mL) were mixed together and stirred in an ice bath. TEMPO (120 mg) was added and a solution of 37% aqueous sodium hypochlorite (48 mL), sodium bicarbonate (5 g) and water (to 100 mL) was added in portions at such a rate that the temperature did not exceed 5° C. Stirring was continued on the ice bath for 20 min. The reaction mixture was diluted with dichloromethane (200 mL) and washed with water (300 mL), 1N hydrochloric acid (300 mL), water (300 mL) and brine (300 mL). The organic layer was dried over sodium sulfate, filtered and the solvent was removed on a rotary evaporator. The crude product (19 g) was purified by chromatography on silica (350 g) with 2% ethyl acetate in heptane (7 L). Pure 25 (16.1 g, 88%) was isolated.

(2-(Benzyloxy)biphenyl-3-yl)(2'-methoxybiphenyl-3-yl)(phenyl)methanol (26): A solution of 3'-bromo-2-methoxybiphenyl (1.08 g, 4.1 mmol) in anhydrous tetrahydrofuran (10 mL) was stirred at −78° C. and 2.5M n-butyllithium in hexanes (1.64 mL, 4.1 mmol) was added at such a rate that the temperature did nor exceed −70° C. Stirring was continued at −78° C. for 1 hr. A solution of 25 (1.5 g, 4.1 mmol) in tetrahydrofuran (6 mL) was added at such a rate that the temperature did not exceed −65° C. Stirring was continued at −78° C. for 20 min and at room temperature for 2 hr. The reaction mixture was poured onto saturated ammonium chloride (150 mL) and extracted with ethyl acetate (150 mL). The organic extract was washed with water (2×80 mL). The organic layer was dried over sodium sulfate, filtered and the solvent was removed on a rotary evaporator. The crude product was purified by chromatography on silica (80 g) with 2% ethyl acetate in heptane (4 L). Pure 26 (0.87 g) and slightly impure 26 (0.38 g) were isolated (total yield 55%).

3'-((2-(Benzyloxy)biphenyl-3-yl)(phenyl)methyl)-2-methoxybiphenyl (D2): A solution of 26 (0.85 g, 1.55 mmol) in acetonitrile (50 mL) and 50% aqueous hypophosphorous acid (21 mL) was kept at reflux for 3.5 hr. The acetonitrile was removed in vacuo, the residue was diluted with ethyl acetate (150 mL) and water (80 mL). Phases were separated. The organic phase was washed with saturated sodium bicarbonate (2×80 mL) and water (2×80 mL) dried over sodium sulfate and filtered. The solvent was removed on a rotary evaporator. The crude product was purified by chromatography on silica (45 g) with 2% ethyl acetate in heptane (4 L) to yield pure D2 (0.42 g, 69%).

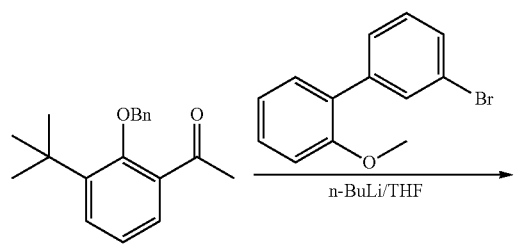

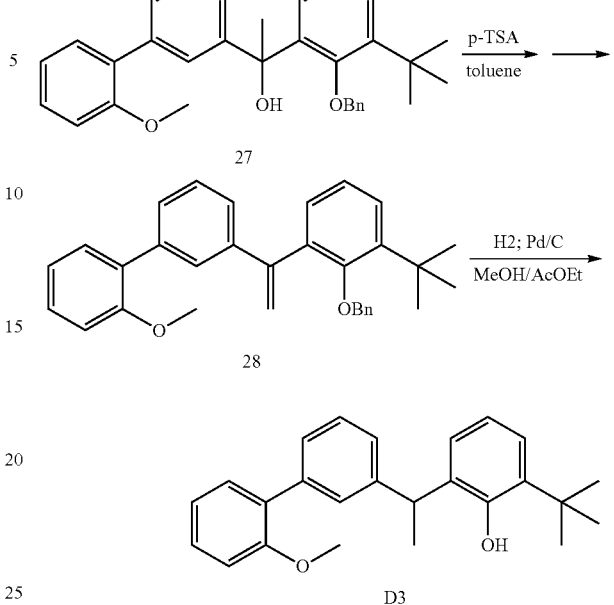

1-(2-(Benzyloxy)-3-tert-butylphenyl)-1-(2'-methoxybiphenyl-3-yl)ethanol (27): A solution of 3'-bromo-2-methoxybiphenyl (1.31 g, 5 mmol) in anhydrous tetrahydrofuran (20 mL) was stirred at −78° C. and 2.5M n-butyllithium in hexanes (2 mL, 5 mmol) was added at such a rate that the temperature did not exceed −70° C. Stirring was continued at −78° C. for 1 hr. A solution of 1-(2-(benzyloxy)-3-tert-butylphenyl)ethanone (1.41 g, 5 mmol) in tetrahydrofuran (8 mL) was added at such a rate that the temperature did not exceed −65° C. Stirring was continued at −78° C. for 20 min and at room temperature for 2 hr. The reaction mixture was poured onto saturated ammonium chloride (80 mL) and extracted with ethyl acetate (150 mL). The organic extract was washed with water (2×80 mL). The organic layer was dried over sodium sulfate, filtered and the solvent was removed on a rotary evaporator. The crude product 27 was used as such in the next step.

3'-(1-(2-(Benzyloxy)-3-tert-butylphenyl)vinyl)-2-methoxybiphenyl (28): A solution of crude 27 (5 mmol) in toluene (120 mL) was treated with p-toluene sulfonic acid (0.2 g) and refluxed under a Dean-Stark trap for 2 hr. After cooling the reaction mixture was diluted with ethyl acetate (100 mL) and washed with saturated sodium bicarbonate (80 mL) and water (2×80 mL). The organic layer was dried over sodium sulfate, filtered and the solvent was removed on a rotary evaporator. The crude product was purified by chromatography on silica (80 g) with hexane (4 L). Pure 28 (1.3 g, 58% over 2 steps) was isolated.

2-tert-Butyl-6-(1-(2'-methoxybiphenyl-3-yl)ethyl)phenol (D3): A solution of 28 (1.3 g, 2.9 mmol) in methanol (20 mL) and ethyl acetate (30 mL) was treated with 20% palladium on activated carbon (50% wet, 0.10 g) and was hydrogenated at 40 psi in a Parr shaker for 3 hr. The catalyst was filtered out and washed with ethyl acetate. The filtrate was stripped and the crude product was purified by chromatography on silica (60 g) with 2% ethyl acetate in hexane (3 L) to afford pure D3 (0.62 g, 59%).

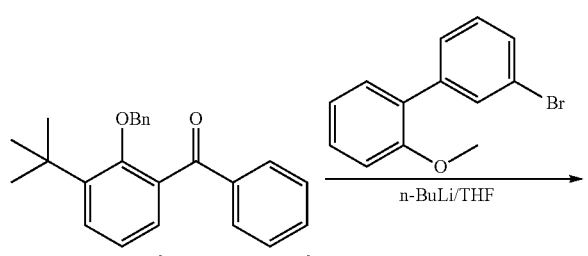

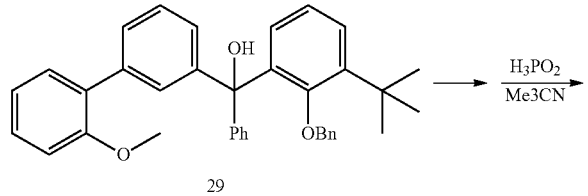

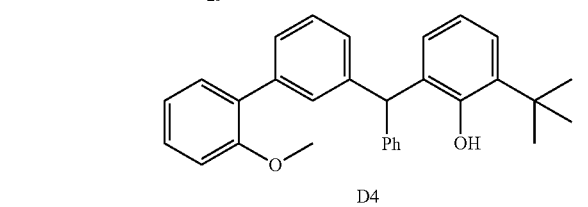

(2-(Benzyloxy)-3-tert-butylphenyl)(2'-methoxybiphenyl-3-yl)(phenyl)methanol (29): A solution of 3'-bromo-2-methoxybiphenyl (1 g, 3.8 mmol) in anhydrous tetrahydrofuran (15 mL) was stirred at −78° C. and 2.5M n-butyllithium in hexanes (1.6 mL, 4 mmol) was added at such a rate that the temperature did not exceed −70° C. Stirring was continued at −78° C. for 1 hr. A solution of (2-(benzyloxy)-3-tert-butylphenyl)(phenyl)methanone (1.3 g, 3.8 mmol) in tetrahydrofuran (5 mL) was added at such a rate that the temperature did not exceed −65° C. The reaction mixture was allowed to reach room temperature slowly and was poured onto saturated ammonium chloride (100 mL) and extracted with ethyl acetate (150 mL). The organic extract was washed with water (2×80 mL). The organic layer was dried over sodium sulfate, filtered and the solvent was removed on a rotary evaporator. The crude product was purified by chromatography on silica (80 g) with 2% ethyl acetate in heptane (3.5 L). Pure 29 (1.2 g, 60%) was isolated.

2-tert-Butyl-6-((2'-methoxybiphenyl-3-yl)(phenyl)methyl)phenol (D4): A solution of 29 (1.2 g, 2.27 mmol) in acetonitrile (70 mL) and 50% aqueous hypophosphorous acid (30 mL) was kept at reflux for 3.5 hr. The acetonitrile was removed in vacuo, the residue was diluted with ethyl acetate (150 mL) and water (100 mL). Phases were separated. The organic phase was washed with saturated sodium bicarbonate (2×100 mL) and water (100 mL), dried over sodium sulfate and filtered. The solvent was removed on a rotary evaporator. The crude product was purified by chromatography on silica (45 g) with hexane (2 L) to yield pure D4 (0.92 g, 96%).

Family E Synthetic Scheme

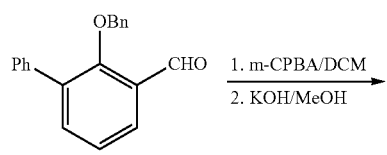

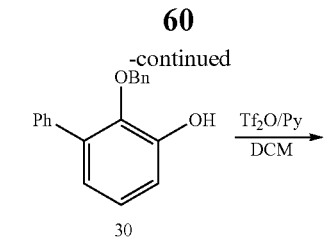

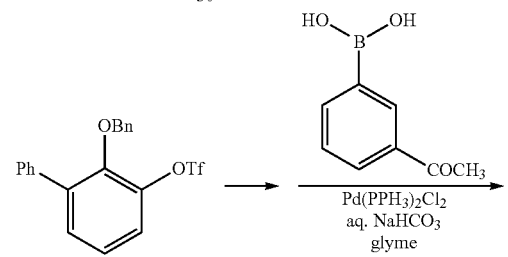

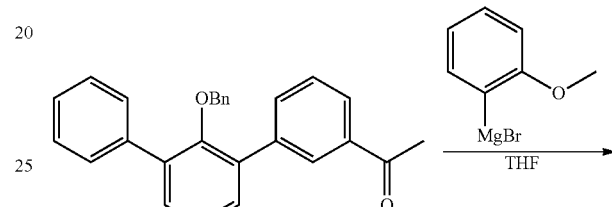

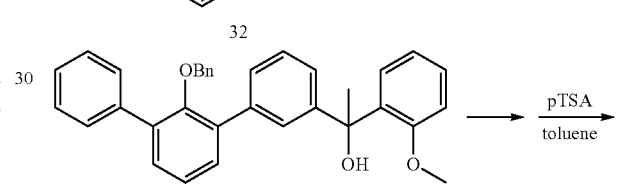

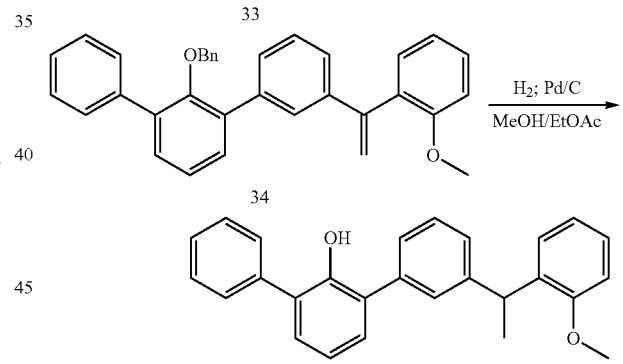

2-(Benzyloxy)biphenyl-3-ol (30): A solution of 2-(benzyloxy)biphenyl-3-carbaldehyde (14.4 g, 50 mmol) in dichloromethane (250 mL) was stirred on an ice bath and m-chloroperbenzoic acid (70%, 13 g) was added in portions over 20 min. Stirring was continued overnight at room temperature. The reaction mixture was diluted with dichloromethane (to 600 mL) and washed with saturated sodium bicarbonate (2×300 mL) and water (300 mL). The organic layer was dried over sodium sulfate and filtered. The solvent was removed in a rotary evaporator. The residue was taken in methanol (250 mL), potassium hydroxide (5 g) was added and this mixture was stirred at room temperature for 2 hr. The solvent was removed in a rotary evaporator. The residue was taken in water (200 mL) and made acidic with 6N hydrochloric acid. The aqueous phase was extracted with ethyl acetate (450 mL). The organic extract was washed with water (100 mL), dried over sodium sulfate and the solvent was removed in a rotary evaporator. The crude product was purified by chromatography on silica (360 g) with 10% ethyl acetate in heptane (4 L) to afford 30 (12 g, 87%).

2-(Benzyloxy)biphenyl-3-yl trifluoromethanesulfonate (31): A solution of 30 (12 g, 43.43 mmol) in dichloromethane (200 mL) was stirred on an ice bath. Pyridine (5.3 mL, 5.42 g, 68.5 mmol, 1.57 equiv.) was added and a solution of triflic anhydride (14.7 g, 52.1 mmol, 1.2 equiv.) in dichloromethane (20 mL) was added at such a rate that the temperature did not exceed 5° C. Stirring was continued on the cold bath for 20 min. Water (10 mL) was added and stirring was continued for 30 min. The reaction mixture was diluted with dichloromethane (to 400 mL) and washed with water (200 mL), 1N hydrochloric acid (200 mL), saturated sodium bicarbonate (200 mL) and water (200 mL). The organic layer was dried over sodium sulfate and filtered. The solvent was removed in a rotary evaporator leaving 31 (17.23 g, 97%).

1-(2'-(Benzyloxy)-3'-phenylbiphenyl-3-yl)ethanone (32): A mixture of 31 (3.18 g, 7.8 mmol), 3-acetylphenylboronic acid (1.6 g, 9.76 mmol, 1.25 equiv.), glyme (5 mL), bis(triphenylphosphine)palladium(II) dichloride (25 mg) and sodium bicarbonate (2.1 g) in water (40 mL) was kept at reflux under nitrogen for 11 hr with additional palladium catalyst (2×30 mg) added after 3 and 7 hr. After cooling, the reaction mixture was diluted with ethyl acetate (200 mL) and washed with water (2×800 mL). The organic layer was dried over sodium sulfate and filtered. The solvent was removed in a rotary evaporator and the crude product was purified by chromatography on silica (120 g) with 2% ethyl acetate in heptane (4 L) to afford 32 (2.9 g, 100%).

1-(2'-(Benzyloxy)-3'-phenybiphenyl-3-yl)-1-(2-methoxyphenyl)ethanol (33): A solution of 32 (1.5 g, 3.96 mmol) in anhydrous tetrahydrofuran (16 mL) was stirred under nitrogen at room temperature and 1M ortho-methoxyphenyl magnesium bromide in tetrahydrofuran (6 mL, 1.5 equiv.) was slowly added. Stirring was continued at room temperature for 30 min and at 60° C. for 3 hr. After cooling, the reaction mixture was poured on saturated ammonium chloride (100 mL) and extracted with ethyl acetate (150 mL). The organic extract was washed with water (2×100 mL), dried over sodium sulfate and filtered. The solvent was removed in a rotary evaporator and the crude 33 thus obtained was used in the next step without further purification.

2-(Benzyloxy)-3-phenyl-3'-(1-(2-methoxyphenyl)vinyl)biphenyl (34): A solution of crude 33 (3.96 mol) in toluene (150 mL) was treated with p-toluenesulfonic acid (100 mg) and refluxed under a Dean-Stark trap for 3 hr. After cooling, the reaction mixture was diluted with ethyl acetate (80 mL) and washed with saturated sodium bicarbonate (80 mL) and water (2×80 mL). The organic extract was dried over sodium sulfate and filtered. The solvent was removed in a rotary evaporator and the crude product was purified by chromatography on silica (80 g) with 2% ethyl acetate in heptane (2 L) to afford 34 (1.15 g, 62%).

3-Phenyl-3'-(1-(2-methoxyphenyl)ethyl)biphenyl-2-ol (E1): A solution of 34 (1.1 g, 2.35 mmol) in methanol (15 mL) and ethyl acetate (30 mL) was treated with 20% palladium on activated carbon (50% wet, 0.05 g) and was hydrogenated at 40 psi in a Parr shaker for 3 hr. The catalyst was filtered out and washed with ethyl acetate. The filtrate was stripped and the crude product was purified by chromatography on silica (50 g) 2% ethyl acetate in hexane (3 L) to afford pure E1 (0.85 g, 95%).

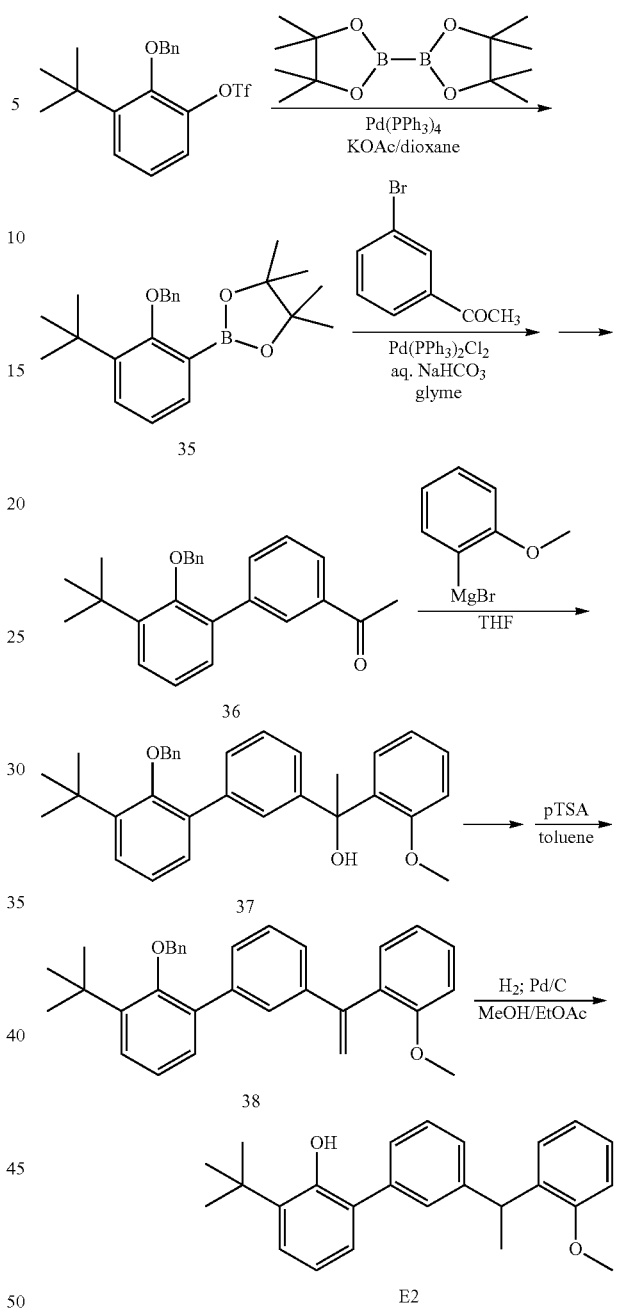

(2-(Benzyloxy)-3-tert-butylphenyl)-4,4,5,5-tetramethyl-1,3,2-dioxaborolane (35): A mixture of 2-(benzyloxy)-3-tert-butylphenyl trifluoromethanesulfonate (7.8 g, 20 mmol), potassium acetate (5.9 g, 60 mmol, 3 equiv.), bis-pinacolato diboron (6.1 g, 24 mmol, 1.2 equiv.) and tetrakis(triphenylphosphine)palladium(0) in dioxane (120 mL) was kept at reflux under nitrogen overnight. After cooling, the reaction mixture was diluted with ethyl acetate (100 mL), the solids were filtered out and the solvent was removed in a rotary evaporator. The residue was taken in toluene (500 mL) and washed with warm water (3×400 mL). The solvent was removed in a rotary evaporator. The residue was taken up in heptane (400 mL), treated with activated carbon and filtered. The solvent was removed in a rotary evaporator and the crude 35 was used as such in the next step.

1-(2'-(Benzyloxy)-3'-tert-butylbiphenyl-3-yl)ethanone (36): A mixture of crude 35 (3.88 g, 10 mmol), 3-acetylphenyl boronic acid (1.8 g, 11 mmol, 1.1 equiv.), bis(triphenylphosphine)palladium(II) dichloride (20 mg), glyme (5.5 mL) and sodium bicarbonate (2.7 g) in water (55 mL) was kept at reflux under nitrogen for 2 hr. Additional palladium catalyst (20 mg) was added and reflux continued for 3 hr. After cooling the reaction mixture was diluted with ethyl acetate (150 mL) and washed with saturated sodium bicarbonate (100 mL) and water (2×100 mL). The organic extract was dried over sodium sulfate and filtered. The solvent was removed in a rotary evaporator and the crude product was purified by chromatography on silica (80 g) with 2% ethyl acetate in heptane (4 L) to afford 36 (3.12 g, 87%).

1-(2'-(Benzyloxy)-3'-tert-butylbiphenyl-3-yl)-1-(2-methoxyphenyl)ethanol (37): A solution of 36 (0.8 g, 2.23 mmol) in anhydrous tetrahydrofuran (8 mL) was stirred under nitrogen at room temperature and 1M ortho-methoxyphenyl magnesium bromide in tetrahydrofuran (3 mL, 1.35 equiv.) was slowly added. Stirring was continued at room temperature for 30 min and at 60° C. for 3 hr. After cooling, the reaction mixture was poured on saturated ammonium chloride (120 mL) and extracted with ethyl acetate (150 mL). The organic extract was washed with water (2×50 mL), dried over sodium sulfate and filtered. The solvent was removed in a rotary evaporator and the crude 37 thus obtained was used in the next step without further purification.

2-(Benzyloxy)-3-tert-butyl-3'-(1-(2-methoxyphenyl)vinyl)biphenyl (38): A solution of crude 37 (2.23 mmol) in toluene (80 mL) was treated with p-toluenesulfonic acid (100 mg) and refluxed under a Dean-Stark trap for 3 hr. After cooling, the reaction mixture was diluted with ethyl acetate (150 mL) and washed with saturated sodium bicarbonate (150 mL) and water (2×100 mL). The organic extract was dried over sodium sulfate and filtered. The solvent was removed in a rotary evaporator and the crude product was purified by chromatography on silica (75 g) with 2% ethyl acetate in heptane (4 L) to afford 38 (0.78 g, 78%).

3-tert-Butyl-3'-(1-(2-methoxyphenyl)ethyl)biphenyl-2-ol (E2): A solution of 38 (0.7 g, 1.56 mmol) in methanol (40 mL) and ethyl acetate (60 mL) was treated with 20% palladium on activated carbon (50% wet, 0.100 g) and was hydrogenated at 40 psi in a Parr shaker for 4 hr. The catalyst was filtered out and washed with ethyl acetate. The filtrate was stripped and the crude product was purified by chromatography on silica (40 g) hexane (3 L) to afford pure E2 (0.54 g, 96%).

Family F Synthetic Scheme

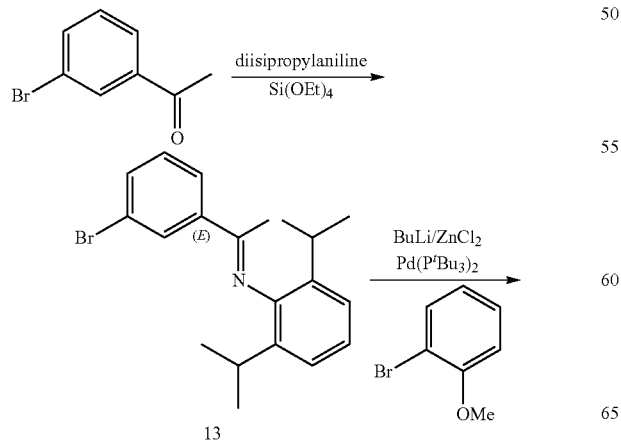

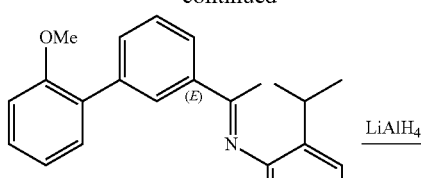

39

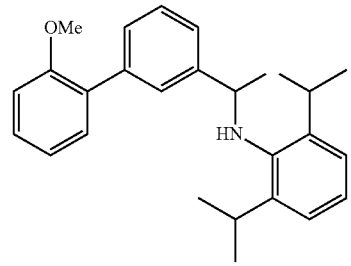

F1

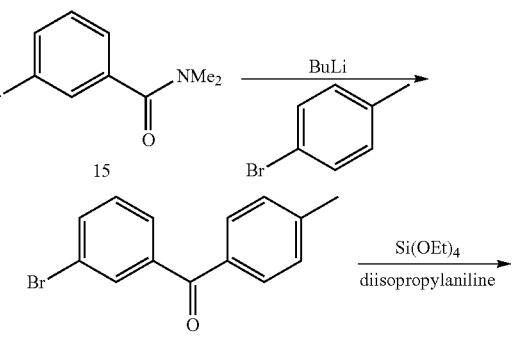

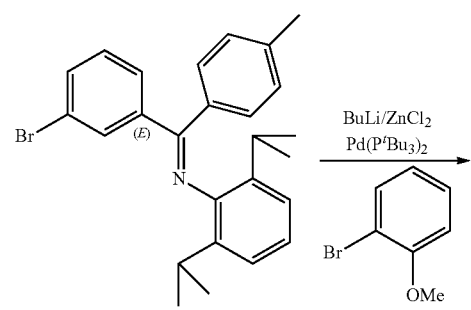

41

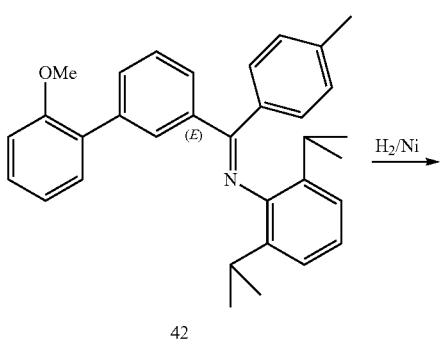

42

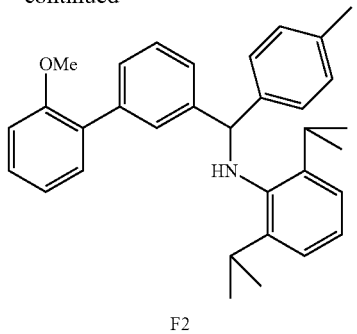

F2

N-[1-(3-Bromophenyl)ethylidene]-2,6-diisopropylaniline (13): In 25 mL Claisens flask in an argon atmosphere, a mixture of 3.98 g (20.0 mmol) of 3-bromoacetophenone, 5.00 g (24.0 mmol) of Si(OEt)$_4$, and 3.90 g (22.0 mmol) of 2,6-diisopropylaniline was heated to 170° C., and then 0.20 mL of 96% H$_2$SO$_4$ was added. This mixture was stirred at this temperature for 1 hr, and the formed ethanol was slowly distilled off. Later, 300 mL of cold water was added, and the product was extracted with 2×70 mL of diethyl ether. The combined extract was dried over K$_2$CO$_3$ and then evaporated to dryness. The product was isolated by flash-chromatography on silica gel 60 (40-63 um, eluent: from hexanes to hexanes-diethyl ether, 50:1, vol.). This procedure gave 6.30 g (88%) of 13.

(2,6-Diisopropylphenyl)[1-(2'-methoxybiphenyl-3-yl)ethylidene]amine (39): To a solution of 2.78 g (7.75 mmol) of 13 in 30 mL of THF, 3.10 mL (7.75 mmol) of 2.5 M "BuLi in hexanes was added at −100° C. The reaction mixture was stirred for 1 hr at −70° C., then cooled to −100° C., and 8.35 mL (8.35 mmol) of 1M ZnCl$_2$ in THF was added. The resulting mixture was slowly warmed to room temperature, stirred for 12 hr at this temperature, and then 1.45 g (7.75 mmol) of 2-bromoanisole and 85 mg (0.15 mmol) of Pd(P$^t$Bu$_3$)$_2$ were added. The resulting mixture was refluxed for 3 hr, and then 5 mL of water was added. This mixture was passed through short layer of silica gel 60 (40-63 um) which was then additionally washed with 30 mL of dichloromethane. The combined organic filtrate was evaporated to dryness, and the product was isolated by flash chromatography on silica gel 60(40-63 um, eluent: from hexanes to hexanes-diethyl ether=20:1, vol.). This procedure gave 2.36 g (79%) of the title product.

(2,6-Diisopropylphenyl)[1-(2'-methoxybiphenyl-3-yl)ethyl]amine (F1): To a suspension of 0.70 g (18.4 mmol) of LiAlH$_4$ in 60 mL of THF, 2.25 g (5.84 mmol) of 39 was added. This reaction mixture was refluxed for 2 hr, and then saturated aqueous Na$_2$SO$_4$ was added. The organic layer was separated, and the aqueous layer was extracted with 2×50 mL of diethyl ether. The combined organic extract was evaporated to dryness, and the product was isolated by flash chromatography on silica gel 60 (40-63 um, eluent: hexanes-diethyl ether from 100:1 to 20:1, vol.) to yield 1.45 g (64%) of Fl.

(3-Bromophenyl)(4-methylphenyl)methanone (40): To a solution of 38.5 g (0.225 mol) of 4-bromotoluene in 450 mL of THF, 300 mL (0.450 mol) of 1.5 M $^t$BuLi in pentane was added dropwise with vigorous stirring for 2 hr at −80° C. This mixture was slowly warmed to room temperature and additionally stirred at this temperature for 30 min. To this mixture 52.0 g (0.23 mol) of 3-bromo-N,N-dimethylbenzamide was added at 0° C., and then this mixture was stirred for 12 hr at room temperature. Later, 300 mL of water was added, organic solvent was evaporated using a rotary evaporator. The product was extracted with 2×200 mL of dichloromethane. The combined organic extracts were evaporated to dryness, and the residue was dried in vacuum. This procedure gave 51.3 g (83%) of 40 which was further used without additional purification.

N-[(3-Bromophenyl)(4-methylphenyl)methylene]-2,6-diisopropylaniline (41): In 50 mL Claisens flask in an argon atmosphere, a mixture of 9.63 g (35.0 mmol) of 40, 8.75 g (42.0 mmol) of Si(OEt)$_4$, and 6.83 g (38.5 mmol) of 2,6-diisopropylaniline was heated to 170° C., and then 0.23 mL of 96% H$_2$SO$_4$ was added. This mixture was stirred at this temperature for 55 hr, and the formed ethanol was slowly distilled off. Further on, 300 mL of cold water was added, and the product was extracted with 2×100 mL of diethyl ether. The combined extract was dried over K$_2$CO$_3$ and then evaporated to dryness. The product was isolated by flash-chromatography on silica gel 60 (40-63 um, eluent: from hexanes to hexanes-diethyl ether, 100:1, vol.) to give 12.7 g (84%) of the title product.

(2,6-Diisopropylphenyl)[(2'-methoxybiphenyl-3-yl)(4-methylphenyl)methylenel]-amine (42): To a solution of 10.0 g (23.0 mmol) of 41 in 120 mL of THF, 9.30 mL (23.0 mmol) of 2.5 M "BuLi in hexanes was added at −100° C. The reaction mixture was stirred for 1 hr at −70° C., then cooled to −100° C., and 24.8 mL (24.8 mmol) of 1.0 M ZnCl$_2$ in THF was added. The resulting mixture was slowly warmed to room temperature, stirred for 12 hr at this temperature, and then 4.30 g (23.0 mmol) of 2-bromoanisole and 250 mg (0.50 mmol) of Pd(P$^t$Bu$_3$)$_2$ were added. The resulting mixture was refluxed for 3 hr, and 10 mL of water was added. Later, this mixture was passed through short layer of silica gel 60 (40-63 um). This silica gel layer was additionally washed with 100 mL of dichloromethane. The combined organic elute was evaporated to dryness. The product was isolated from the residue using flash chromatography on silica gel 60 (40-63 um, eluent: hexanes and then hexanes-diethyl ether=20:1, vol.). This procedure gave 9.10 g (86%) of 42.

(2,6-Diisopropylphenyl)[(2'-methoxybiphenyl-3-yl)(4-methylphenyl)methyl]-amine (F2): A mixture of 9.10 g (19.7 mmol) of 42 in 180 mL of THF and fresh Ni-Raney obtained from 4.32 g of 50% alloy of Ni with Al was hydrogenated in a stainless steel autoclave at 70 atm of hydrogen for 4 hr at 70° C. Then, the reaction mixture was filtered through glass frit, and the filtrate was evaporated to dryness. The product was isolated by flash chromatography on silica gel 60 (40-63 um, eluent: hexanes-ethyl acetate=100:1, vol. and then 10:1, vol.) to generate 6.94 g (76%) of F2.

Polymerization Process
Metal-Ligand Solution Procedures

To a 2 mL glass vial, 25 μmol of ligand was added with a spinbar and sealed. Toluene solvent was added to the reaction vial, typically between 0.30-0.70 mL, and stirred for 30-60 minutes at room temperature. An equimolar amount of transition metal precursor was then added to the reaction vial via syringe to form the metal-ligand solution: Method A) 0.50 mL of 0.05 mol/L tetrabenzylzirconium or tetrabenzylhathium (obtained from Strem Chemical, used as received) was added and the resulting metal-ligand solution was stirred at temperatures between 20° C.-100° C. for predetermined reaction times, typically between 10-15 hr, after which the vessel was cooled to room temperature and an additional 0.50 mL toluene was added to the reaction vial. Method B) Metal precursor was added, 0.50 mL of 0.05 mol/L tetrakis(dimethylamino)zirconium or tetrakis(dimethylamino)hafnium (obtained from Strem Chemical, used as received), and the metal-ligand solution was stirred at temperatures between 20° C.-100° C. for predetermined reaction times, typically between 10-15 hr. The glass vial was cooled to room temperature and 0.50 mL of an 0.50 mol/L solution of trialkylaluminum, typically triethylaluminum (TEAl) or tri-i-butylaluminum (TiBAl), was added to the metal-ligand solution and stirred for typically 0.5-1.5 hr. Subsequently an aliquot of the metal-ligand solution was removed, typically between 0.10-0.15 mL, and diluted to final volume of 3.50 mL to afford a final metal-ligand solution, typically between 0.30-1.00 mmol/L. A small aliquot of the resulting metal-ligand solution was injected into the PPR reactor, typically between 0.025-0.100 μmol, and reaction progress monitored as described below.

Ethylene/1-octene copolymerization were carried out in a parallel pressure reactor, which is described in U.S. Pat. Nos. 6,306,658, 6,455,316, and 6,489,168, WO 00/09255, and Murphy et al., J. Am. Chem. Soc., 2003, 125, 4306-4317, each of which is incorporated herein by reference. A pre-weighed glass vial insert and disposable stirring paddle were fitted to each reaction vessel of the reactor, which contains 48 individual reaction vessels. The reactor was then closed and each vessel was individually heated to a set temperature (usually between 50° C. and 100° C.) and pressurized to a pre-determined pressure of ethylene (generally between 75 and 350 psi). 100 μL of 1-octene (637 umol) was injected into each reaction vessel through a valve, followed by 500 μL of hexane. A solution of tri-n-octylaluminum was then added to act as a co-catalyst/scavenger, typically 100 μl of 10 mmol/L in hexane (1.0 μmol). The contents of the vessel were then stirred at 800 rpm. An activator solution (usually N,N'-dimethylanilinium tetrakis(pentafluorophenyl)borate in toluene, 0.40 mmol/L, ~1.1 equiv) was then injected into the reaction vessel along with 500 μL hexane. A toluene solution of catalyst was injected (0.020-0.120 μmol) or an aliquot of catalyst premix solution (0.020-0.120 μmol), followed by an aliquot of hexane (500 μL). All runs were performed in duplicate. The reaction was then allowed to proceed until a set time limit (usually 30 min) or until a set amount of ethylene had been taken up by the reaction (ethylene pressure was maintained in each reaction vessel at the pre-set level by computer control). At this point, the reaction was quenched by exposure to air. After the polymerization reaction, the glass vial insert containing the polymer product and solvent was removed from the pressure cell and the inert atmosphere glovebox and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine comonomer incorporation, and by DSC (see below) to determine melting point.

For discreet metal complexes (C1)HfMe$_2$ and (C1)HfBz$_2$, the following changes to the screening protocol were made: each vessel was individually heated to a set temperature (usually 50° C. and 80° C.) and pressurized to a pre-determined pressure of ethylene (generally between 75 and 350 psi). 100 uL of 1-octene (637 umol) was injected into each reaction vessel through a valve, followed by 500 uL of hexane. 100 uL of tri-n-octylaluminum solution (10 mmol/L in hexane, 1 umol) was then added to act as a co-catalyst/scavenger. The contents of the vessel were then stirred at 800 rpm. An activator solution (usually N,N'-dimethylanilinium tetrakis(pentafluorophenyl)borate in toluene, 0.40 mmol/L, ~1 equiv) was then injected into the reaction vessel along with 500 uL hexane, followed by a toluene solution of catalyst (0.40 mmol/L, 20-120 nmol) and another aliquot of hexane (500 uL). In a typical run, reaction conditions were varied such that two temperatures, three pressures and four catalyst concentrations were investigated. All runs were performed in duplicate.

High temperature size exclusion chromatography was performed using an automated "Rapid GPC" system as described in U.S. Pat. Nos. 6,491,816, 6,491,823, 6,475,391, 6,461,515, 6,436,292, 6,406,632, 6,175,409, 6,454,947, 6,260,407, and 6,294,388 each of which is incorporated herein by reference. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/min and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution were injected into the system. The concentration of the polymer in the eluent was monitored using an evaporative light scattering detector. The molecular weights obtained are relative to linear polystyrene standards.

Differential Scanning calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./min and then cooled at a rate of 50° C./min. Melting points were collected during the heating period. The ratio of 1-octene to ethylene incorporated in the polymers (weight %) was determined by rapid FT-IR spectroscopy on a Bruker Equinox 55+ IR in reflection mode. Samples were prepared in a thin film format by evaporative deposition techniques. Weight % 1-octene was obtained from the ratio of peak heights at 1378 and 4322 cm$^{-1}$. This method was calibrated using a set of ethylene/1-octene copolymers with a range of known wt % 1-octene content.

Polymerization data shown in Tables 1 and 2 is intended to be representative of the catalytic behavior of compounds described herein and not comprehensive.

TABLE 1

Selected High Throughput Polymerization Results for the Discrete Metal Complexes (C1)HfMe$_2$ and (C1)HfBz$_2$

| Example | Catalyst | Amount (nmol) | Temp (° C.) | Pressure (psi) | Time (sec) | Yield (mg) | Activity (g/mmol h bar) | Mw (kDa) | MWD (Mw/Mn) | Tm (° C.) |
|---|---|---|---|---|---|---|---|---|---|---|
| 1 | (C1)HfMe$_2$ | 20 | 50 | 200 | 1800 | 4 | 26 | ND | ND | ND |
| 2 | (C1)HfMe$_2$ | 20 | 50 | 200 | 1800 | 6 | 40 | ND | ND | ND |
| 3 | (C1)HfMe$_2$ | 20 | 50 | 350 | 1800 | 5 | 20 | ND | ND | ND |
| 4 | (C1)HfMe$_2$ | 20 | 50 | 350 | 1800 | 5 | 19 | ND | ND | ND |
| 5 | (C1)HfMe$_2$ | 20 | 80 | 200 | 1800 | 6 | 47 | ND | ND | ND |
| 6 | (C1)HfMe$_2$ | 20 | 80 | 200 | 1800 | 29 | 211 | 3062 | 1.6 | 133 |
| 7 | (C1)HfMe$_2$ | 20 | 80 | 350 | 1800 | 16 | 67 | 4020 | 1.5 | 134 |
| 8 | (C1)HfMe$_2$ | 20 | 80 | 350 | 1800 | 9 | 38 | ND | ND | ND |

TABLE 1-continued

Selected High Throughput Polymerization Results for the Discrete Metal Complexes (C1)HfMe$_2$ and (C1)HfBz$_2$

| Example | Catalyst | Amount (nmol) | Temp (° C.) | Pressure (psi) | Time (sec) | Yield (mg) | Activity (g/mmol h bar) | Mw (kDa) | MWD (Mw/Mn) | Tm (° C.) |
|---|---|---|---|---|---|---|---|---|---|---|
| 9 | (C1)HfMe$_2$ | 40 | 50 | 75 | 1800 | 14 | 138 | 3329 | 1.6 | 133 |
| 10 | (C1)HfMe$_2$ | 40 | 50 | 75 | 1800 | 6 | 63 | ND | ND | ND |
| 11 | (C1)HfMe$_2$ | 40 | 50 | 200 | 1800 | 16 | 59 | 3994 | 1.4 | 133 |
| 12 | (C1)HfMe$_2$ | 40 | 50 | 200 | 1800 | 16 | 47 | 4085 | 1.5 | 134 |
| 13 | (C1)HfMe$_2$ | 40 | 50 | 350 | 1800 | 16 | 33 | 4464 | 1.4 | 133 |
| 14 | (C1)HfMe$_2$ | 40 | 50 | 350 | 1800 | 16 | 33 | 4586 | 1.3 | 133 |
| 15 | (C1)HfMe$_2$ | 40 | 80 | 75 | 1800 | 81 | 784 | 1613 | 2.0 | 133 |
| 16 | (C1)HfMe$_2$ | 40 | 80 | 75 | 1800 | 65 | 630 | 1865 | 1.8 | 133 |
| 17 | (C1)HfMe$_2$ | 40 | 80 | 200 | 1317 | 93 | 464 | 2808 | 1.6 | 134 |
| 18 | (C1)HfMe$_2$ | 40 | 80 | 200 | 1575 | 87 | 362 | 2375 | 1.6 | 133 |
| 19 | (C1)HfMe$_2$ | 40 | 80 | 350 | 1800 | 38 | 79 | 4090 | 1.4 | 133 |
| 20 | (C1)HfMe$_2$ | 40 | 80 | 350 | 1800 | 38 | 79 | 4365 | 1.4 | 134 |
| 21 | (C1)HfMe$_2$ | 80 | 50 | 75 | 1800 | 28 | 136 | 3448 | 1.6 | 133 |
| 22 | (C1)HfMe$_2$ | 80 | 50 | 75 | 1800 | 25 | 169 | 3430 | 1.7 | 133 |
| 23 | (C1)HfMe$_2$ | 80 | 50 | 200 | 1800 | 37 | 67 | 4080 | 1.5 | 134 |
| 24 | (C1)HfMe$_2$ | 80 | 50 | 200 | 1800 | 34 | 63 | 4090 | 1.5 | 134 |
| 25 | (C1)HfMe$_2$ | 80 | 50 | 350 | 1800 | 41 | 43 | 4098 | 1.4 | 135 |
| 26 | (C1)HfMe$_2$ | 80 | 50 | 350 | 1800 | 38 | 39 | 4223 | 1.5 | 134 |
| 27 | (C1)HfMe$_2$ | 80 | 80 | 75 | 1185 | 113 | 838 | 1718 | 2.4 | 131 |
| 28 | (C1)HfMe$_2$ | 80 | 80 | 75 | 1297 | 108 | 729 | 1725 | 2.4 | 132 |
| 29 | (C1)HfMe$_2$ | 80 | 80 | 200 | 721 | 147 | 668 | 2378 | 1.9 | 133 |
| 30 | (C1)HfMe$_2$ | 80 | 80 | 200 | 608 | 119 | 640 | 2644 | 1.8 | 133 |
| 31 | (C1)HfMe$_2$ | 80 | 80 | 350 | 698 | 93 | 250 | 3481 | 1.6 | 132 |
| 32 | (C1)HfMe$_2$ | 80 | 80 | 350 | 1663 | 88 | 99 | 4113 | 1.6 | 132 |
| 33 | (C1)HfMe$_2$ | 120 | 50 | 75 | 1800 | 60 | 193 | 3413 | 1.7 | 132 |
| 34 | (C1)HfMe$_2$ | 120 | 50 | 75 | 1800 | 55 | 178 | 3593 | 1.7 | 132 |
| 35 | (C1)HfMe$_2$ | 120 | 50 | 200 | 1800 | 59 | 71 | 3873 | 1.5 | 133 |
| 36 | (C1)HfMe$_2$ | 120 | 50 | 200 | 1800 | 60 | 72 | 4233 | 1.5 | 133 |
| 37 | (C1)HfMe$_2$ | 120 | 50 | 350 | 1680 | 62 | 45 | 3859 | 1.7 | 134 |
| 38 | (C1)HfMe$_2$ | 120 | 50 | 350 | 1800 | 57 | 39 | 4037 | 1.6 | 133 |
| 39 | (C1)HfMe$_2$ | 120 | 80 | 75 | 668 | 94 | 819 | 1581 | 2.7 | 132 |
| 40 | (C1)HfMe$_2$ | 120 | 80 | 75 | 675 | 96 | 832 | 1778 | 2.3 | 132 |
| 41 | (C1)HfMe$_2$ | 120 | 80 | 200 | 387 | 139 | 781 | 2522 | 1.8 | 134 |
| 42 | (C1)HfMe$_2$ | 120 | 80 | 200 | 348 | 121 | 759 | 2451 | 1.9 | 135 |
| 43 | (C1)HfMe$_2$ | 120 | 80 | 350 | 405 | 118 | 363 | 3337 | 1.7 | 133 |
| 44 | (C1)HfMe$_2$ | 120 | 80 | 350 | 577 | 102 | 219 | 4243 | 1.4 | 132 |
| 45 | (C1)HfBz$_2$ | 20 | 50 | 200 | 1800 | 3 | 18 | ND | ND | ND |
| 46 | C1)HfBz$_2$ | 20 | 50 | 200 | 1800 | 5 | 34 | ND | ND | ND |
| 47 | C1)HfBz$_2$ | 20 | 50 | 350 | 1800 | 3 | 11 | ND | ND | ND |
| 48 | C1)HfBz$_2$ | 20 | 50 | 350 | 1800 | 5 | 18 | ND | ND | ND |
| 49 | C1)HfBz$_2$ | 20 | 80 | 200 | 1800 | 2 | 13 | ND | ND | ND |
| 50 | C1)HfBz$_2$ | 20 | 80 | 200 | 1800 | 22 | 158 | 2694 | 2.3 | 132 |
| 51 | C1)HfBz$_2$ | 20 | 80 | 350 | 1800 | 1 | 2 | ND | ND | ND |
| 52 | C1)HfBz$_2$ | 20 | 80 | 350 | 1800 | 12 | 48 | 3300 | 2.0 | 132 |
| 53 | C1)HfBz$_2$ | 40 | 50 | 75 | 1800 | 18 | 175 | 2920 | 2.0 | 132 |
| 54 | C1)HfBz$_2$ | 40 | 50 | 75 | 1800 | 9 | 86 | ND | ND | ND |
| 55 | C1)HfBz$_2$ | 40 | 50 | 200 | 1800 | 13 | 47 | 3690 | 1.6 | 133 |
| 56 | C1)HfBz$_2$ | 40 | 50 | 200 | 1800 | 13 | 46 | 3548 | 1.7 | 133 |
| 57 | C1)HfBz$_2$ | 40 | 50 | 350 | 1800 | 13 | 26 | 3483 | 1.5 | 134 |
| 58 | C1)HfBz$_2$ | 40 | 50 | 350 | 1800 | 11 | 22 | 4006 | 1.5 | 134 |
| 59 | C1)HfBz$_2$ | 40 | 80 | 75 | 1800 | 42 | 405 | 1534 | 2.8 | 133 |
| 60 | C1)HfBz$_2$ | 40 | 80 | 75 | 1800 | 63 | 611 | 1538 | 3.0 | 132 |
| 61 | C1)HfBz$_2$ | 40 | 80 | 200 | 1800 | 68 | 246 | 2784 | 1.9 | 132 |
| 62 | C1)HfBz$_2$ | 40 | 80 | 200 | 1800 | 61 | 221 | 2942 | 1.8 | 132 |
| 63 | C1)HfBz$_2$ | 40 | 80 | 350 | 1800 | 36 | 75 | 3480 | 1.8 | 133 |
| 64 | C1)HfBz$_2$ | 40 | 80 | 350 | 1800 | 36 | 73 | 3290 | 2.1 | 132 |
| 65 | C1)HfBz$_2$ | 80 | 50 | 75 | 1800 | 19 | 91 | 3096 | 2.2 | 132 |
| 66 | C1)HfBz$_2$ | 80 | 50 | 75 | 1800 | 58 | 283 | 3378 | 2.0 | 130 |
| 67 | C1)HfBz$_2$ | 80 | 50 | 200 | 1800 | 29 | 52 | 3666 | 1.6 | 134 |
| 68 | C1)HfBz$_2$ | 80 | 50 | 200 | 1800 | 33 | 60 | 3602 | 1.6 | 130 |
| 69 | C1)HfBz$_2$ | 80 | 50 | 350 | 1800 | 34 | 32 | 3912 | 1.5 | 135 |
| 70 | C1)HfBz$_2$ | 80 | 50 | 350 | 1800 | 28 | 29 | 3478 | 3.9 | 135 |
| 71 | C1)HfBz$_2$ | 80 | 80 | 75 | 558 | 104 | 1628 | 1200 | 2.7 | 130 |
| 72 | C1)HfBz$_2$ | 80 | 80 | 75 | 859 | 104 | 1071 | 1338 | 2.7 | 129 |
| 73 | C1)HfBz$_2$ | 80 | 80 | 200 | 443 | 118 | 870 | 2323 | 1.9 | 131 |
| 74 | C1)HfBz$_2$ | 80 | 80 | 200 | 735 | 131 | 582 | 2481 | 1.9 | 132 |
| 75 | C1)HfBz$_2$ | 80 | 80 | 350 | 1294 | 83 | 119 | 3533 | 1.6 | 133 |
| 76 | C1)HfBz$_2$ | 80 | 80 | 350 | 1149 | 85 | 137 | 3482 | 1.6 | 131 |
| 77 | C1)HfBz$_2$ | 120 | 50 | 75 | 1164 | 84 | 417 | 3185 | 2.1 | 132 |
| 78 | C1)HfBz$_2$ | 120 | 50 | 75 | 1299 | 84 | 377 | 3175 | 2.2 | 131 |
| 79 | C1)HfBz$_2$ | 120 | 50 | 200 | 1800 | 45 | 55 | 3969 | 1.5 | 134 |
| 80 | C1)HfBz$_2$ | 120 | 50 | 200 | 1800 | 50 | 62 | 3987 | 1.5 | 133 |
| 81 | C1)HfBz$_2$ | 120 | 50 | 350 | 1800 | 44 | 30 | 4256 | 1.5 | 134 |
| 82 | C1)HfBz$_2$ | 120 | 50 | 350 | 1800 | 49 | 34 | 4294 | 1.4 | 134 |

TABLE 1-continued

Selected High Throughput Polymerization Results for the Discrete Metal Complexes (C1)HfMe₂ and (C1)HfBz₂

| Example | Catalyst | Amount (nmol) | Temp (° C.) | Pressure (psi) | Time (sec) | Yield (mg) | Activity (g/mmol h bar) | Mw (kDa) | MWD (Mw/Mn) | Tm (° C.) |
|---|---|---|---|---|---|---|---|---|---|---|
| 83 | C1)HfBz₂ | 120 | 80 | 75 | 463 | 104 | 1310 | 1008 | 2.5 | 126 |
| 84 | C1)HfBz₂ | 120 | 80 | 75 | 541 | 113 | 1215 | 1181 | 2.6 | 131 |
| 85 | C1)HfBz₂ | 120 | 80 | 200 | 415 | 152 | 797 | 2472 | 1.9 | 132 |
| 86 | C1)HfBz₂ | 120 | 80 | 200 | 456 | 149 | 712 | 2450 | 1.8 | 134 |
| 87 | C1)HfBz₂ | 120 | 80 | 350 | 483 | 122 | 314 | 3157 | 1.7 | 133 |
| 88 | C1)HfBz₂ | 120 | 80 | 350 | 618 | 99 | 199 | 3812 | 1.5 | 135 |

TABLE 2

Selected High Throughput Polymerization Results for In Situ Complexations

| Example | Ligand | Ligand amount (nmol) | Metal Source | Metal amount (nmol) | Temp (° C.) | Pressure (psi) | Time (sec) | Yield (mg) | Activity (g/mmol h bar) | Mw (kDa) | MWD (Mw/Mn) | Comonomer (wt %) |
|---|---|---|---|---|---|---|---|---|---|---|---|---|
| 89 | A1 | 80 | ZrBz4 | 78 | 80 | 75 | 1800 | 7 | 32 | 175 | 1.5 | |
| 90 | A1 | 99 | Zr(NR2)4 | 98 | 80 | 75 | 1800 | 13 | 51 | 429 | 18.1 | |
| 91 | B1 | 80 | ZrBz4 | 78 | 80 | 75 | 1800 | 20 | 98 | 1265 | 9.4 | 5.18 |
| 92 | B1 | 99 | HfBz4 | 98 | 80 | 75 | 1800 | 6 | 24 | ND | ND | |
| 93 | B1 | 99 | Zr(NR2)4 | 98 | 80 | 75 | 1800 | 53 | 209 | 756 | 23.1 | |
| 94 | D2 | 99 | Zr(NR2)4 | 98 | 80 | 75 | 1800 | 16 | 61 | 630 | 15.5 | |
| 95 | D3 | 99 | Zr(NR2)4 | 98 | 80 | 75 | 1800 | 13 | 50 | 273 | 3.0 | |
| 96 | E2 | 99 | Zr(NR2)4 | 98 | 80 | 75 | 1800 | 20 | 76 | 686 | 20.6 | |
| 97 | F2 | 80 | ZrBz4 | 78 | 80 | 75 | 1800 | 16 | 78 | 137 | 3.5 | |
| 98 | F2 | 60 | Zr(NR2)4 | 59 | 80 | 75 | 1800 | 8 | 53 | 157 | 1.9 | |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A transition metal catalyst compound represented by one of the structures:

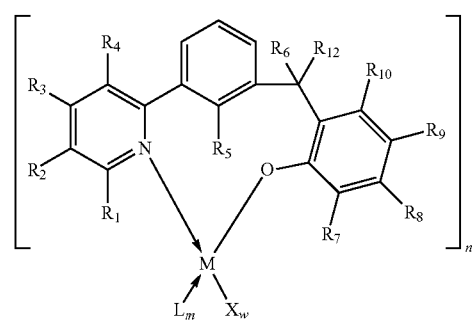

A

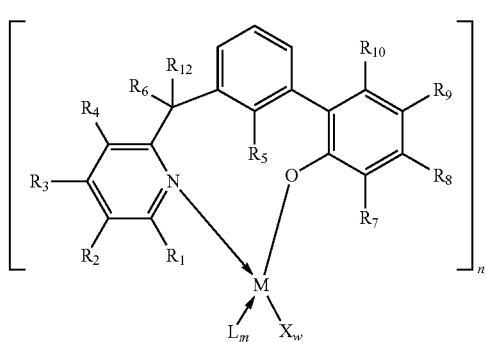

B

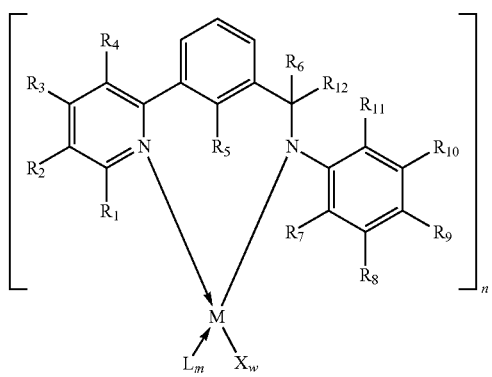

C

-continued

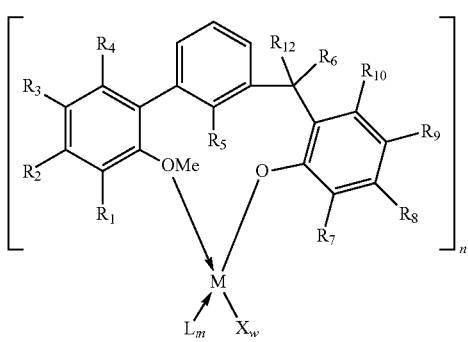
D

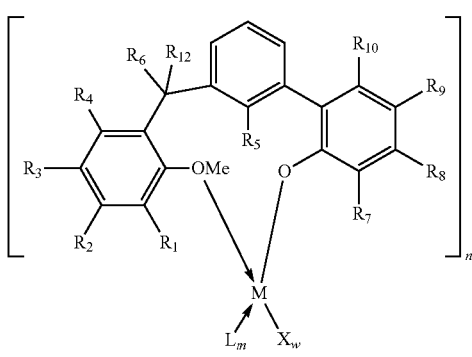
E

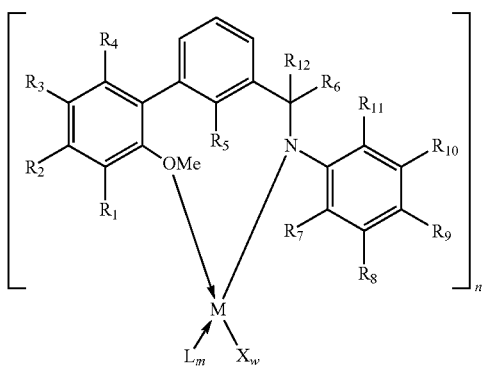
F wherein
each X is, independently, a hydride, a halogen, a hydrocarbyl, a substituted hydrocarbyl, a halocarbyl, or a substituted halocarbyl;
w is 0, 1, 2 or 3;
each $R^1$, $R^2$, $R^{3,4}$ $R^5$, $R^6$ $R^7$ $R^8$ $R^9$ $R^{10}$ $R^{12}$ and R11, is, independently, a hydrogen, a hydrocarbyl, a substituted hydrocarbyl, a halocarbyl, a substituted halocarbyl, a halogen, an alkoxide, a sulfide, an amide, a phosphide, a silyl or an anionic heteroatom-containing group, or independently, may join together to form a $C_4$ to $C_{62}$ cyclic or polycyclic ring structure;
L is a neutral ligand bonded to M;
M is Hf, Zr or Ti;
m is 0, 1 or 2 and indicates the absence or presence of L; and
n is 1 or 2.

2. The compound according to claim 1, wherein the structure is C.

3. The compound of claim 1, wherein n is 1 and w is 2 or 3.

4. The compound of claim 1, wherein $R^6$ is phenyl or methyl and $R^7$ is phenyl or t-butyl.

5. The compound according to claim 1 wherein n is 1 and the structure is:

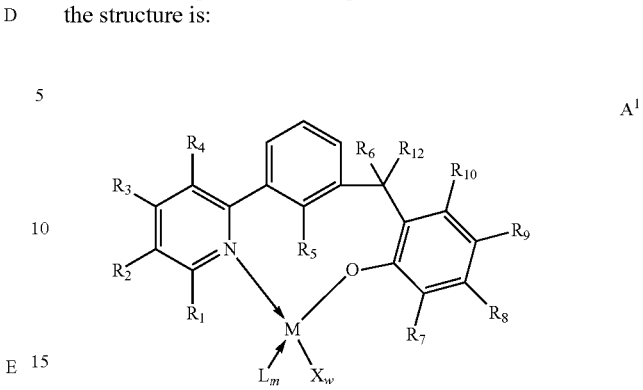
A¹

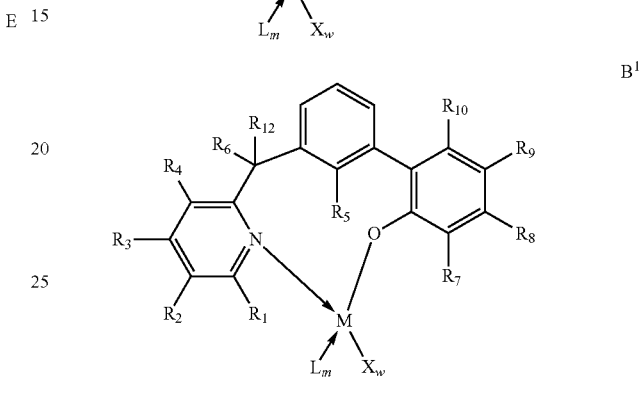
B¹

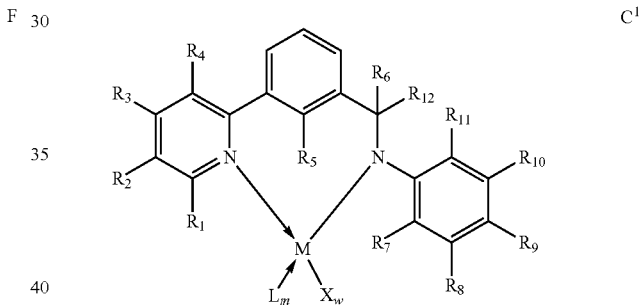
C¹

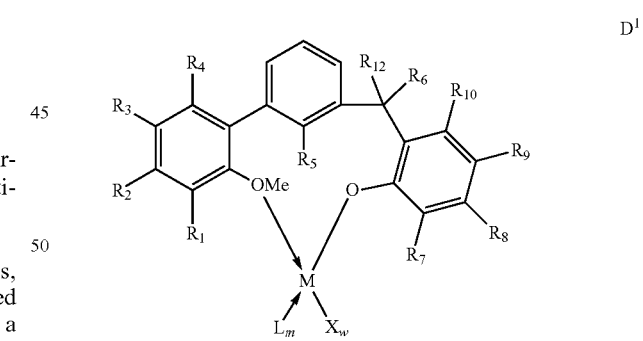
D¹

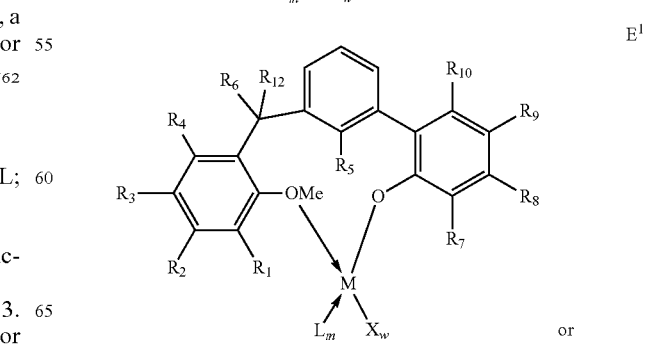
E¹ or

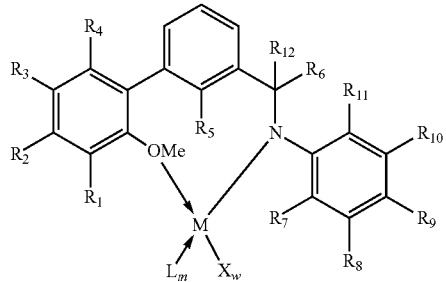

wherein w is 2 or 3.

6. The compound of claim 1, wherein at least one of $R^6$ or $R^{12}$ is not a hydrogen atom.

7. The compound of claim 1, wherein when $R^5$ is a hydrogen atom, M may react with the $R^5$ hydrogen atom to generate HX and a bond is formed between the carbon bearing position at $R^5$ and M.

8. The compound of claim 1 wherein the neutral ligand L includes molecules of pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, or styrene.

9. The compound of claim 1, wherein the structure is D.

10. The compound of claim 1 wherein the structure is D and $R^5$ is a hydrogen, a hydrocarbyl, a halocarbyl, a halogen, a sulfide, an amide, a phosphide, or a silyl.

11. The compound of claim 1 wherein the structure is D and $R^5$ is a substituted hydrocarbyl.

12. A transition metal catalyst composition represented by one of the structures:

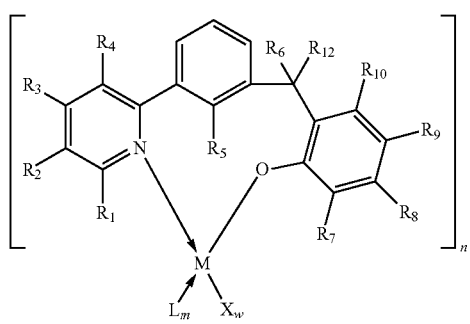

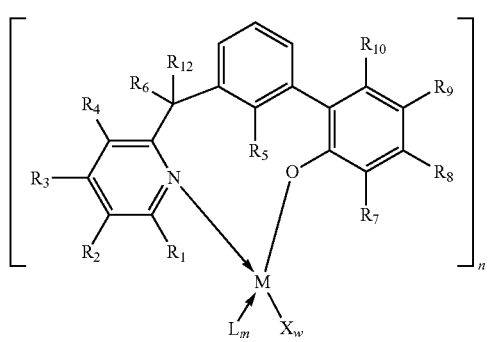

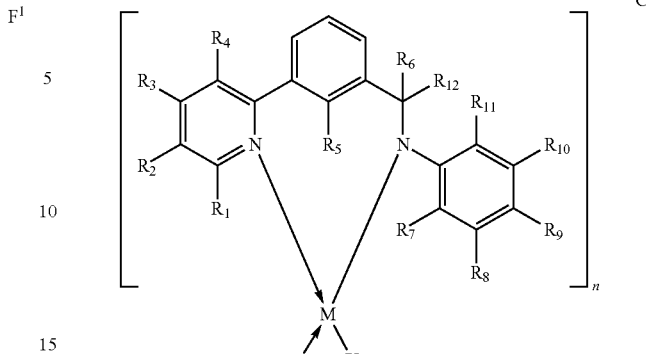

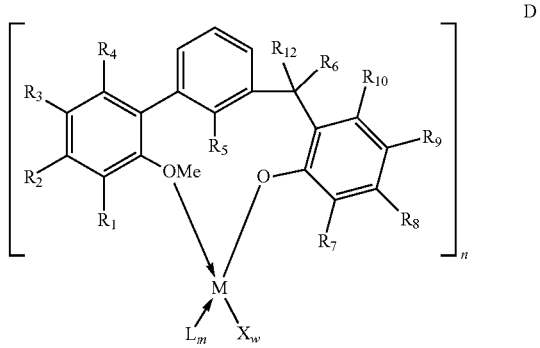

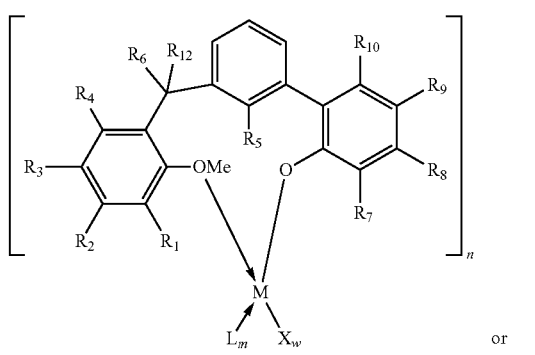

or

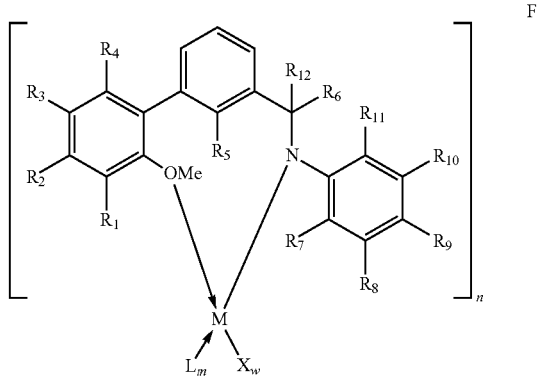

wherein
each X is, independently, a hydride, a halogen, a hydrocarbyl, a substituted hydrocarbyl, a halocarbyl, or a substituted halocarbyl;
w is 0, 1, 2 or 3;
each $R^1$, $R^2$, $R^3$, $R^4$, $R^5$, $R^6$, $R^7$, $R^8$, $R^9$, R10, R12 and R11, is, independently, a hydrogen, a hydrocarbyl, a substituted hydrocarbyl, a halocarbyl, a substituted halocarbyl, a halogen, an alkoxide, a sulfide, an amide, a phosphide, a silyl or an anionic heteroatom-containing group, or independently, may join together to form a $C_4$ to $C_{62}$ cyclic or polycyclic ring structure;

L is a neutral ligand bonded to M;

M is Hf, Zr or Ti;

m is 0, 1 or 2 and indicates the absence or presence of L;

n is 1 or 2; and an activator.

13. The composition according to claim 12, wherein the structure is C.

14. The composition of claim 12, wherein n is 1 and w is 2 or 3.

15. The composition of claim 12, wherein $R^6$ is phenyl or methyl and $R^7$ is phenyl or t-butyl.

16. The composition according to claim 12 wherein n is 1 and the structure is:

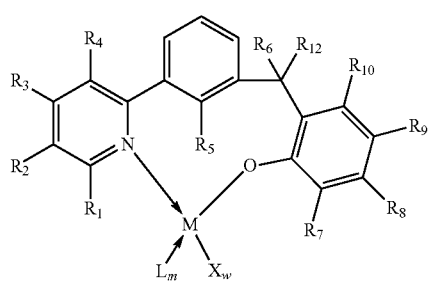

A¹

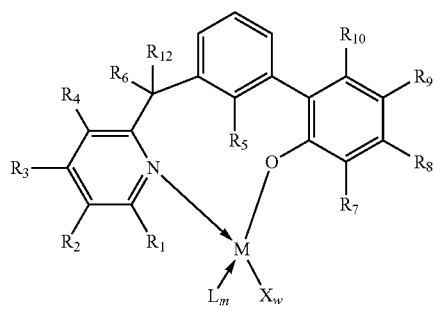

B¹

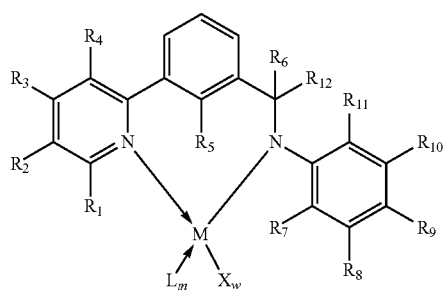

C¹

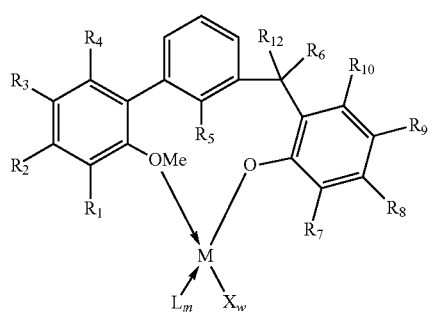

D¹

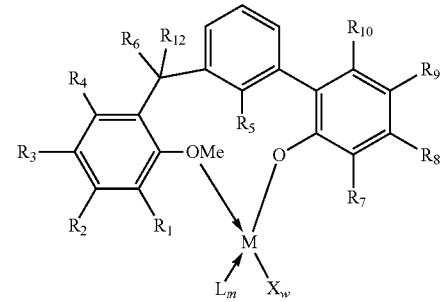

E¹ or

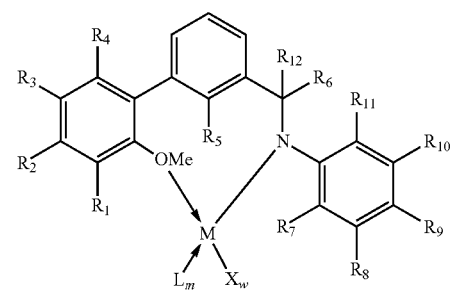

F¹ wherein w is 2 or 3.

17. The composition of claim 12, wherein at least one of $R^6$ or $R^{12}$ is not a hydrogen atom.

18. The composition of claim 12, wherein the neutral ligand L includes molecules of pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, or styrene.

19. The composition of claim 12, wherein the structure is D.

20. The composition of claim 12 wherein the structure is D and $R^5$ is a hydrogen, a hydrocarbyl, a halocarbyl, a halogen, a sulfide, an amide, a phosphide, or a silyl.

21. The composition of claim 12 wherein the structure is D and $R^5$ is a substituted hydrocarbyl.

22. A process for polymerization comprising:

contacting ethylene and, optionally, one or more unsaturated monomers with a transition metal catalyst compound represented by one of the structures:

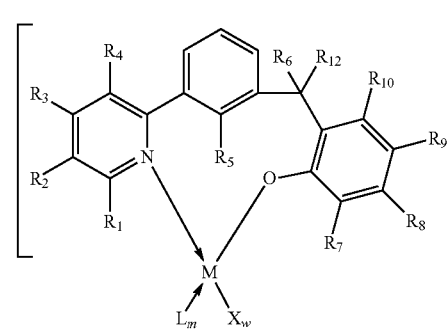

A

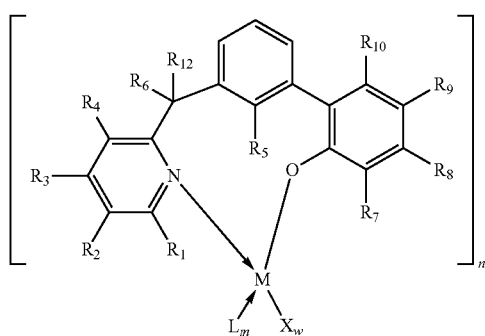

B

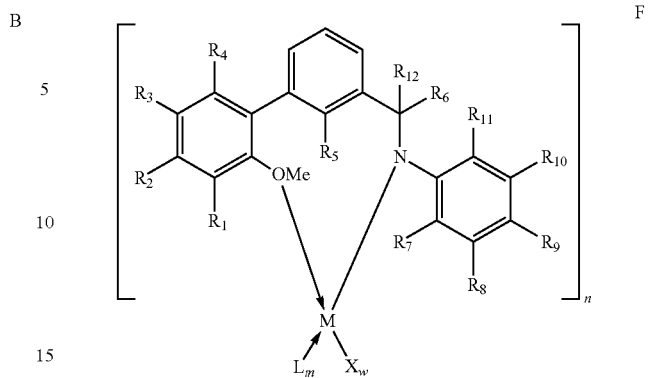

F

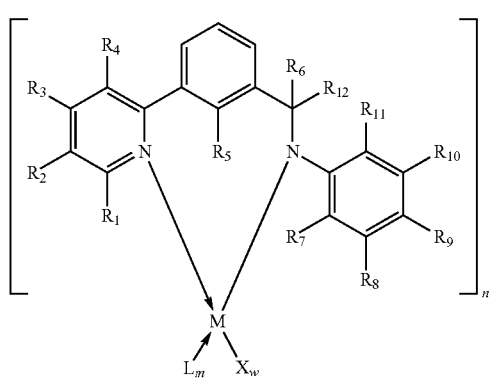

C wherein
each X is, independently, a hydride, a halogen, a hydrocarbyl, a substituted hydrocarbyl, a halocarbyl, or a substituted halocarbyl;
w is 0, 1, 2 or 3;
each $R^1$, $R^2$, $R^3$, $^4$ $R^5$, $R^6$ $R_7$ $R^8 R^9$ $R^{10} R^{12}$ and R11, is, independently, a hydrogen, a hydrocarbyl, a substituted hydrocarbyl, a halocarbyl, a substituted halocarbyl, a halogen, an alkoxide, a sulfide, an amide, a phosphide, a silyl or an anionic heteroatom-containing group, or independently, may join together to form a $C_4$ to $C_{62}$ cyclic or polycyclic ring structure;
L is a neutral ligand bonded to M;
M is Hf, Zr or Ti;
m is 0, 1 or 2 and indicates the absence or presence of L; and
n is 1 or 2.

23. The process of claim 22, wherein the structure is C.

D

24. The process of claim 22, wherein n is 1 and w is 2 or 3.

25. The process of claim 22, wherein $R^6$ is phenyl or methyl and $R^7$ is phenyl or t-butyl.

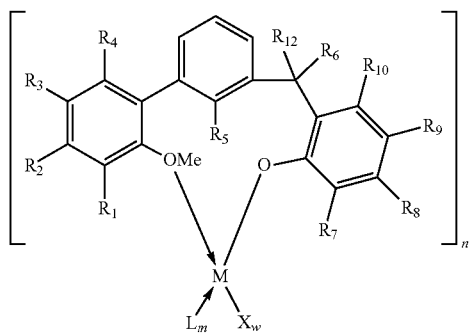

26. The process according to claim 22, wherein n is 1 and the structure is:

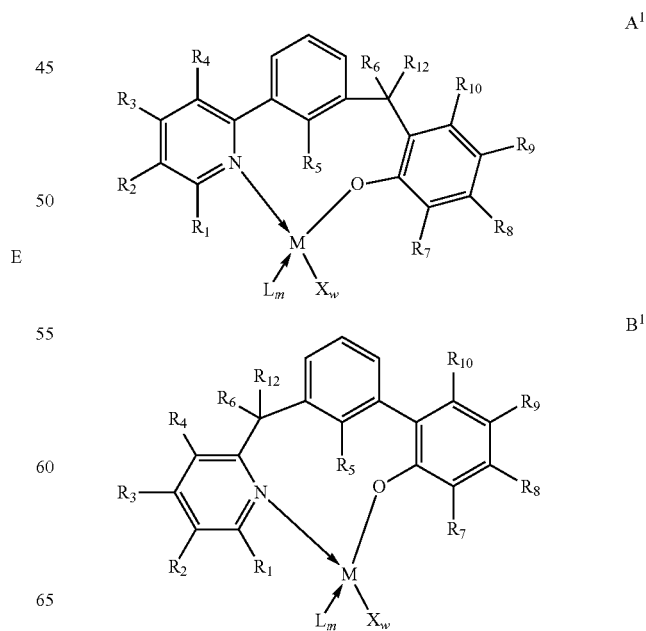

A¹

B¹

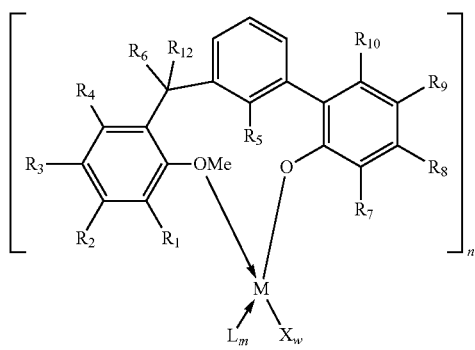

or

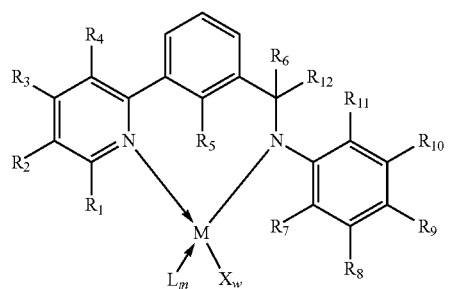

C¹

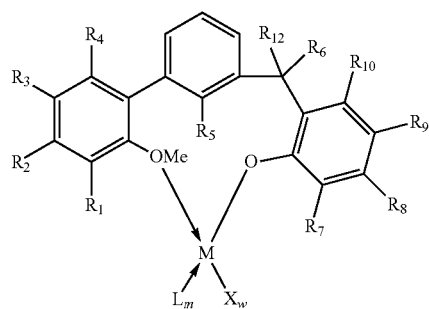

D¹

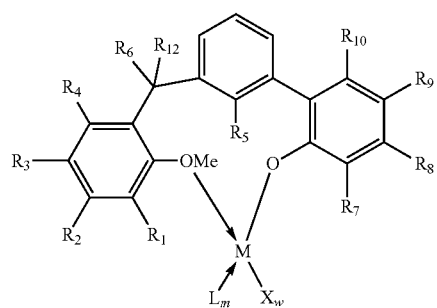

E¹ or

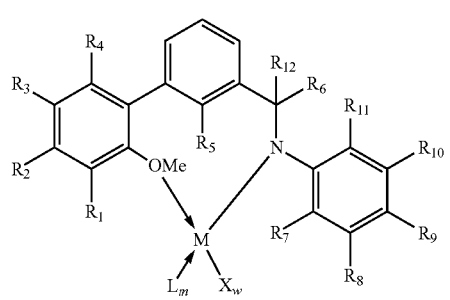

F¹ wherein w is 2 or 3.

27. The process of claim 22, wherein the neutral ligand L includes molecules of pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, or styrene.

28. The process of claim 22, wherein the structure is D.

29. The process of claim 22 wherein the structure is D and $R^5$ is a hydrogen, a hydrocarbyl, a halocarbyl, a halogen, a sulfide, an amide, a phosphide, or a silyl.

30. The process of claim 22 wherein the structure is D and $R^5$ is a substituted hydrocarbyl.

31. A process for polymerization comprising:
contacting ethylene and, optionally, one or more unsaturated monomers with a transition metal catalyst composition represented by one of the structures:

E

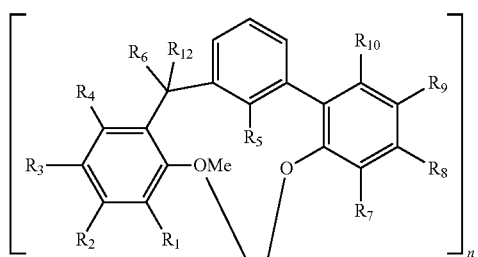

or

F

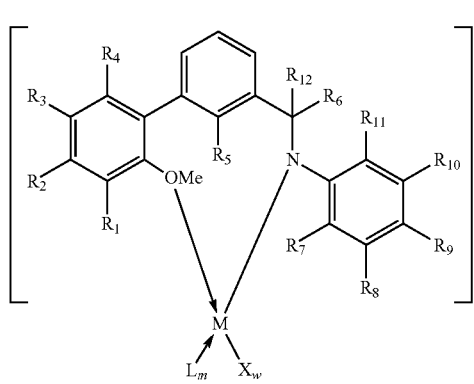

wherein
each X is, independently, a hydride, a halogen, a hydrocarbyl, a substituted hydrocarbyl, a halocarbyl, or a substituted halocarbyl;
w is 0, 1, 2 or 3;
each $R^1$, $R^2$, $R^3$, $R^4$, $R^5$, $R^6$, $R^7$, $R^8$, $R^9$, $R^{10}$, $R^{12}$ and $R^{11}$, is, independently, a hydrogen, a hydrocarbyl, a substituted hydrocarbyl, a halocarbyl, a substituted halocarbyl, a halogen, an alkoxide, a sulfide, an amide, a phosphide, a silyl or an anionic heteroatom-containing group, or independently, may join together to form a $C_4$ to $C_{62}$ cyclic or polycyclic ring structure;
L is a neutral ligand bonded to M;
M is Hf, Zr or Ti;
m is 0, 1 or 2 and indicates the absence or presence of L;
n is 1 or 2; and
an activator.

32. The process of claim 31, wherein the structure is C.

33. The process of claim 31, wherein n is 1 and w is 2 or 3.

34. The process of claim 31, wherein $R^6$ is phenyl or methyl and $R^7$ is phenyl or t-butyl.

35. The process according to claim 31, wherein n is 1 and the structure is:

$A^1$

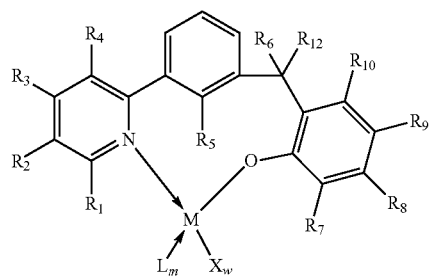

$B^1$

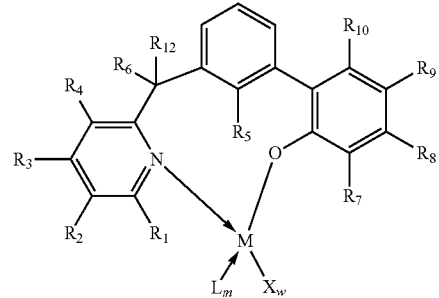

$C^1$

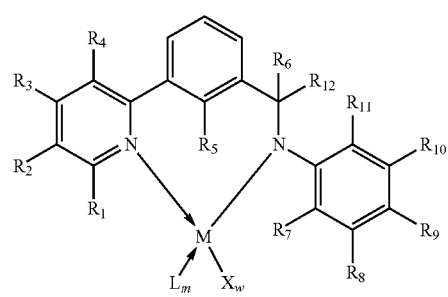

$D^1$

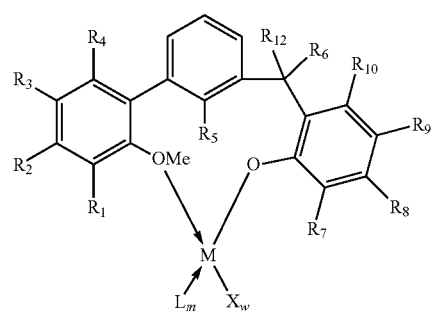

$E^1$

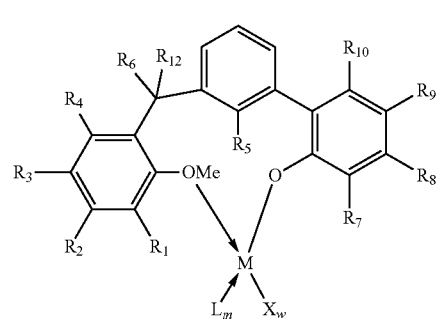

or $F^1$

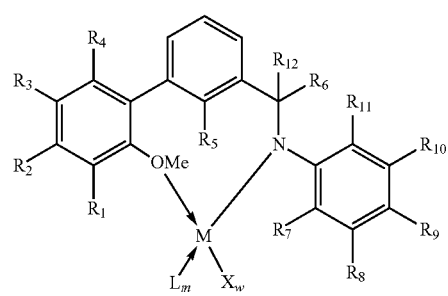

wherein w is 2 or 3.

36. The process of claim 31, wherein the neutral ligand L includes molecules of pyridine, acetonitrile, diethyl ether, tetrahydrofuran, dimethylaniline, trimethylamine, tributylamine, trimethylphosphine, triphenylphosphine, lithium chloride, ethylene, propylene, butene, octene, or styrene.

37. The process of claim 31, wherein the structure is D.

38. The process of claim 31 wherein the structure is D and $R^5$ is a hydrogen, a hydrocarbyl, a halocarbyl, a halogen, a sulfide, an amide, a phosphide, or a silyl.

39. The process of claim 31 wherein the structure is D and $R^5$ is a substituted hydrocarbyl.

40. The process of claim 31, wherein the product of the polymerization is homopolyethylene.

* * * * *